US008828939B2

(12) United States Patent
Weimer et al.

(10) Patent No.: US 8,828,939 B2
(45) Date of Patent: Sep. 9, 2014

(54) MODIFIED VITAMIN K DEPENDENT POLYPEPTIDES

(75) Inventors: Thomas Weimer, Gladenbach (DE); Stefan Schulte, Marburg (DE); Kay Hofmann, Köln (DE); Hans-Peter Hauser, Marburg (DE)

(73) Assignee: CSL Behring GmbH, Marburg (DE)

( * ) Notice: Subject to any disclaimer, the term of this patent is extended or adjusted under 35 U.S.C. 154(b) by 938 days.

(21) Appl. No.: 11/632,552

(22) PCT Filed: Aug. 10, 2005

(86) PCT No.: PCT/EP2005/008678
§ 371 (c)(1),
(2), (4) Date: Jan. 17, 2007

(87) PCT Pub. No.: WO2006/018204
PCT Pub. Date: Feb. 23, 2006

(65) Prior Publication Data
US 2009/0130060 A1 May 21, 2009

(30) Foreign Application Priority Data
Aug. 17, 2004 (EP) .................................. 04019485

(51) Int. Cl.
 *A61K 38/36* (2006.01)
 *C07K 14/745* (2006.01)
 *C12N 15/62* (2006.01)
 *C12N 9/64* (2006.01)

(52) U.S. Cl.
 CPC .............. *C12N 15/62* (2013.01); *C12N 9/6424* (2013.01)
 USPC .......................................... 514/13.7; 530/380

(58) Field of Classification Search
 None
 See application file for complete search history.

(56) References Cited

U.S. PATENT DOCUMENTS

| 4,784,950 | A | | 11/1988 | Hagen et al. | |
|---|---|---|---|---|---|
| 5,358,932 | A | * | 10/1994 | Foster et al. ..................... | 514/12 |
| 5,580,560 | A | | 12/1996 | Nicolaisen et al. | |
| 6,277,618 | B1 | | 8/2001 | Kopetzki et al. | |
| 6,531,298 | B2 | * | 3/2003 | Stafford et al. ............... | 435/69.6 |
| 2002/0137673 | A1 | | 9/2002 | Pingel et al. | |
| 2002/0151471 | A1 | | 10/2002 | Pingel et al. | |
| 2003/0096338 | A1 | | 5/2003 | Pedersen et al. | |
| 2003/0100075 | A1 | * | 5/2003 | Persson et al. ................ | 435/69.6 |
| 2003/0100506 | A1 | * | 5/2003 | Nelsestuen ..................... | 514/12 |
| 2003/0100740 | A1 | | 5/2003 | Persson et al. | |
| 2003/0104978 | A1 | | 6/2003 | Persson et al. | |
| 2003/0130191 | A1 | | 7/2003 | Persson et al. | |
| 2003/0170863 | A1 | | 9/2003 | Persson et al. | |
| 2003/0181381 | A1 | | 9/2003 | Himmelspach et al. | |
| 2009/0275123 | A1 | | 11/2009 | Nelsestuen | |

FOREIGN PATENT DOCUMENTS

| EP | 0 770 625 B1 | 9/1996 |
|---|---|---|
| EP | 1177304 | 6/2009 |
| JP | 2001061479 | 3/2001 |
| WO | WO 88/10295 | 12/1988 |
| WO | WO 91/09960 | 7/1991 |
| WO | WO 99/29767 | 6/1999 |
| WO | WO 00/66753 | 11/2000 |
| WO | WO 01/10896 | 2/2001 |
| WO | WO 01/10896 A2 | 2/2001 |
| WO | WO 02/38162 A1 | 5/2002 |
| WO | WO 02/077218 A1 | 10/2002 |
| WO | WO 03/035861 | 5/2003 |
| WO | WO 03/035861 A2 | 5/2003 |
| WO | WO 03/093465 A1 | 11/2003 |
| WO | WO 2004/011675 A2 | 2/2004 |
| WO | WO 2004/029090 A1 | 4/2004 |
| WO | WO 2004/029091 A2 | 4/2004 |
| WO | WO 2004/083361 A2 | 9/2004 |
| WO | WO 2004/108763 A2 | 12/2004 |
| WO | WO 2004/111242 A1 | 12/2004 |
| WO | WO 2005/032581 A3 | 4/2005 |

OTHER PUBLICATIONS

Kappel et al., Covalent modification of the solubilized rat liver vitamin K-dependent carboxylase with pyridoxal-5'-phosphate, Arch Biochem Biophys. 235(2):521-8, 1984.*
Toomey et al. (1991) J. Biol. Chem. 266: 19198-19202.*
International Searching Authority, Notification of Transmittal of the International Search Report and the Written Opinion dated Dec. 20, 2005 (14 pages).
Search Report, issued by European Patent Office dated Jan. 17, 2005 (5 pages).
Mollerup et al., "The Use of RP-HPLC for Measuring Activation and Cleavage of rFVIIa During Purification," Biotechnology and Bioengineering 48:501-05 (1995).
Bharadwaj et al., "A Novel Mutation in the Catalytic Domain that Reduces Tissue Factor Binding, Impairs Activation by Factor XA, and Abolishes Amidolytic and Coagulant Activity," The Journal of Biological Chemistry 271(48):30685-91(1996).
Dickinson et al., "Identification of Surface Residues Mediating Tissue Factor Binding and Catalytic Function of the Serine Protease Factor VIIa," Proc. Natl. Acad. Sci. 93:14379-84 (1996).
Kornfelt et al., "Oxidation of Methionine Residues in Coagulation Factor VIIa," Archives of Biochemistry and Biophysics 363(1):43-54 (1999).
Kemball-Cook et al., "Coagulation Factor VII Gln$^{100}$ → Arg Amino Acid Substitution at the Epidermal Growth Factor 2-Protease Domain Interface Results in Severely Reduced Tissue Factor Binding and Procoagulant Function," The Journal of Biological Chemistry 273(14):8516-21 (1998).

(Continued)

*Primary Examiner* — Michael Pak
(74) *Attorney, Agent, or Firm* — Finnegan, Henderson, Farabow, Garrett & Dunner, LLP

(57) ABSTRACT

The present invention relates to modified cDNA sequences coding for vitamin K-dependent polypeptides, in particular human Factor VII, human Factor VIIa, human Factor IX and human protein C and their derivatives with improved stability and extended plasma half life, recombinant expression vectors containing such cDNA sequences, host cells transformed with such recombinant expression vectors, recombinant polypeptides and derivatives which do have biological activities of the unmodified wild type protein but having improved stability and processes for the manufacture of such recombinant proteins and their derivatives. The invention also covers a transfer vector for use in human gene therapy, which comprises such modified DNA sequences.

19 Claims, 3 Drawing Sheets

(56) References Cited

OTHER PUBLICATIONS

Iino et al., "Functional Consequences of Mutations in Ser-52 and Ser-60 in Human Blood Coagulation Factor VII," Archives of Biochemistry and Biophysics 352(2):182-92 (1998).

Ruf et al., "Importance of Factor VIIa Gla-Domain Residue Arg-36 for Recognition of the Macromolecular Substrate Factor X Gla-Domain," Biochemistry 38:1957-66 (1999).

Mizuguchi et al., "Structural Element of Factor VIIa Required for Active Site Formation," Thromb. Haemost. Suppl.:466, abstract 1474 (Aug. 1999).

Maun et al., "Disulfide Locked Variants of Factor VIIa with a Restricted β-strand Conformation Have Enhanced Enzymatic Activity," Protein Science 14:1171-80 (2005).

Lindley et al., "Pharmacokinetics and Pharmacodynamics of Recombinant Factor VIIa," Clin. Pharmacol. Ther. 55(6):638-48 (1994).

Shah et al., "Manipulation of the Membrane Binding Site of Vitamin K-dependent Proteins: Enhanced Biological Function of Human Factor VII," Proc. Natl. Acad. Sci. 95:4229-34 (1994).

Gabriel et al., "Monitoring Coagulation and the Clinical Effects of Recombinant Factor VIIa," Seminars in Hematology 41(1)(Suppl. 1):20-24 (2004).

Erhardtsen, E., "To General Haemostasis—The Evidence-Based Route," Pathophysiol. Haemost. Thromb. 32(Suppl. 1):47-52 (2002).

First Examination Report for Indian Patent Application No. 690/CHENP/2007 dated Jul. 26, 2010, 3 pages.

* cited by examiner

Fig.1b

MODIFIED VITAMIN K DEPENDENT POLYPEPTIDES

This application is the U.S. National Stage of International Application No. PCT/EP2005/008678, filed Aug. 10, 2005, and also claims priority to European Application No.04019485.4, filed Aug. 17, 2004, both of which are incorporated herein by reference.

FIELD OF THE INVENTION

The present invention relates to modified cDNA sequences coding for vitamin K-dependent polypeptides, in particular human Factor VII, human Factor VIIa, human Factor IX and human protein C and their derivatives with improved stability and extended plasma half-life, recombinant expression vectors containing such cDNA sequences, host cells transformed with such recombinant expression vectors, recombinant polypeptides and derivatives which do have biological activities of the unmodified wild type protein but having improved stability and processes for the manufacture of such recombinant proteins and their derivatives. The invention also covers a transfer vector for use in human gene therapy, which comprises such modified DNA sequences.

BACKGROUND OF THE INVENTION

Vitamin K-dependent proteins are used to treat certain types of hemophilia. Classic hemophilia or hemophilia A is an inherited bleeding disorder. It results from a chromosome X-linked deficiency of blood coagulation Factor VIII, and affects almost exclusively males with an incidence between one and two individuals per 10.000. The X-chromosome defect is transmitted by female carriers who are not themselves hemophiliacs. The clinical manifestation of hemophilia A is an increased bleeding tendency. Before treatment with Factor VII concentrates was introduced the mean life span for a person with severe hemophilia was less than 20 years. The use of concentrates of Factor VIII from plasma and later on that of recombinant forms of FVIII has considerably improved the situation for the hemophilia patients increasing the mean life span extensively, giving most of them the possibility to live a more or less normal life. Hemophilia B being 5 times less prevalent than hemophilia A is caused by non-functional or missing FIX and is treated with FIX concentrates from plasma or a recombinant form of FIX. In both hemophilia A and in hemophilia B the most serious medical problem in treating the disease is the generation of alloantibodies against the replacement factors. Up to 30% of all hemophilia A patients develop antibodies to FVIII. Antibodies to FIX occur to a lesser extent but with more severe consequences, as they are less susceptible to immune tolerance induction therapy.

The current model of coagulation states that the physiological trigger of coagulation is the formation of a complex between tissue factor (TF) and Factor VIIa (FVIIa) on the surface of TF expressing cells which are normally located outside the vasculature. This leads to the activation of FIX and FX ultimately generating some thrombin. In a positive feedback loop thrombin activates FVIII and FIX, the so-called "intrinsic" arm of the blood coagulation cascade, thus amplifying the generation of FXa, which is necessary for the generation of the full thrombin burst to achieve complete hemostasis. It was shown that by administering supraphysiological concentrations of FVIIa hemostasis is achieved bypassing the need for FVIIa and FIXa. The cloning of the cDNA for FVII (U.S. Pat. No. 4,784,950) made it possible to develop a recombinant replacement of that plasma derived coagulation factor. This FVIIa was successfully administered for the first time in 1988 to a patient with a high titer of inhibitory antibodies to FVIII. Ever since the number of indications of FVIIa has grown steadily showing a potential to become a universal hemostatic agent (Erhardtsen, 2002).

FVII is a single-chain glycoprotein with a molecular weight of 50 kDa, which is secreted by liver cells into the blood stream as an inactive zymogen of 406 amino acids. It contains 10 γ-carboxy-glutamic acid residues (positions 6, 7, 14, 16, 19, 20, 25, 26, 29, and 35) localized in the Gla-domain of the protein. The Gla residues require vitamin K for their biosynthesis. Located C-terminal to the Gla domain are two epidermal growth factor domains followed by a trypsin-type serine protease domain. Further posttranslational modifications of FVII encompass hydroxylation (Asp 63), N-(Asn145 and Asn322) as well as O-type glycosylation (Ser52 and Ser60).

FVII is converted to its active form FVIIa by proteolysis of the single peptide bond at Arg152-Ile153 leading to the formation of two polypeptide chains, a N-terminal light chain (17 kDa) and a C-terminal heavy chain (28 kDa) which are held together by one disulfide bridge. In contrast to other vitamin K-dependent polypeptides no activation peptide which is cleaved off during activation has been described for FVII. The Arg152-Ile153 cleavage site corresponds by homology comparison to the C-terminal activation cleavage site of other vitamin K-dependent polypeptides. However as Arg144 might also constitute a protease cleavage site it cannot be excluded that FVII in contrast to current thinking possesses an activation peptide of 8 amino acids between Arg144 and Arg152.

Essential for attaining the active conformation of FVIIa is the formation of a salt bridge after activation cleavage between Ile153 and Asp343. Activation of FVII can be achieved in vitro by FXa, FXIIa, FIXa, FVIIa, FSAP and thrombin. Mollerup et al. (Biotechnol. Bioeng. (1995) 48: 501-505) reported that some cleavage also occurs in the heavy chain at Arg290 and or Arg315.

FVII is present in plasma in a concentration of 500 ng/ml. 1%, e.g. 5 ng/ml of FVII is present as FVIIa. Plasma half-life of FVII was found to be about 4 hours and that of FVIa about 2 hours. Although the half-life of FVIIa of 2 hours is comparatively long for an activated coagulation factor, which is, otherwise more in the order of minutes due to the irreversible inhibition by Serpins like antithrombin III, this nevertheless constitutes a severe drawback for the therapeutic use of FVIIa, as it leads to the need of multiple i.v. injections or continuous infusion to achieve hemostasis resulting in very high cost of treatment and inconvenience for the patient. As on the other hand FVIIa has the potential to be used as a universal hemostatic agent there is a high medical need to develop forms of FVIIa which have a longer functional half-life.

Several attempts have been made to modify FVII:

Nicolaisen et al. (WO 88/10295, Jun. 25, 1987) suggest that by deleting or modifying the following amino acids FVII will be stabilized against proteolytic degradation: Lys32, Lys38, Lys143, Arg290, Arg315, Lys316, Lys341, Arg392, Arg 396, Arg 402, Ile42 and Tyr44.

Nicolaison (U.S. Pat. No. 5,580,560, Nov. 13, 1989) extends WO 88/10295 to include also mutations or deletions in Arg304, Phe278 and Tyr332 to render FVII/FVIIa less susceptible to proteolysis.

Bharadwaj et al. (JBC (1996), 48 pp. 30685-30691) expressed the FVII mutant Phe328Ser that failed to activate FX and showed no detectable amidolytic activity. Dickinson et al. (PNAS (1996) 93, 14379-14384) proposed FVIIa variants in which Lys157, Val158, Glu296, Met298, Asp334, Ser336 or Lys337 have been replaced by Ala.

Nelsestuen (WO 99/29767 Oct. 23, 1997) modified the Gla domain by introducing point mutations in a way to enhance its affinity to phospholipid membranes thereby resulting into a modified FVIIa with enhanced specific activity. Proposed point mutations are at Pro10, Gly11, Arg28 and Lys32.

Nelsestuen (WO 00/66753, Apr. 29, 1999) modified the Gla domain by introducing point mutations in a way to enhance its affinity to phospholipid membranes thereby resulting into a modified FVIIa with enhanced specific activity. Proposed point mutations are at 5, 9, 11, 12, 29, 33, 34, 35 and/or 36.

Kornfelt et al. (Archiv. Biochem. and Biophys., 363, pp 43-54) showed that the oxidation of Met298 and Met306 leads to a 30% higher dissociation rate of FVIIa-ox from TF and a 20% lower FX activation as compared to wild type FVIIa.

Kemball-Cook et al. (JBC (1998), 14 pp. 8516-8521) expressed the FVII mutant Gln100Arg and showed that it had no detectable clotting activity though having amidolytic activity comparable to wild type FVIIa and speculate that this might be due to impaired association with TF.

Iino et al. Arch. Biochem. Biophys. (1998) 352:182-192 showed that mutating the O-glycosylation sites Ser-52 and Ser-60 decreases the coagulatory activity of FVIIa possibly interfering with the interaction with TF.

Ruf et al. (Biochemistry (1999) 16, pp. 1957-66) showed that the mutation Arg36Ala leads to decreased rate of FX activation.

Iwanaga et al. (Thromb. Haemost. (supplement August 1999), 466 abstract 1474) refer to a FVII variant in which residues 316-320 are deleted or residues 311-322 are replaced with the corresponding residues from trypsin.

Soeiima Kenji et al. (JP2001061479, Aug. 24, 1999) created a modified FVIIa with enhanced specific activity by cleaving the disulfide group between Cys159 and Cys164 or by substituting, adding or deleting at least a part of the loop structure from Thr233 to Asp244 or by substituting, adding, or deleting at least a part of the intervening sequence between Arg304 and Cys329.

Pedersen et al. (US 2003/0096338 Feb. 11, 2000) claim conjugates of FVII and FVIIa with non-polypeptidic moieties including also sugars with the aim to prolong FVIIa half-life. The claims also encompass the introduction of novel N- and/or O-type glycosylation sites or the introduction of novel combined with the removal of a preexisting N- and/or O-type glycosylation sites to obtain in vivo glycoconjugates.

Persson and Olsen (US 2003/0170863, May 3, 2000) taught modified FVIIa in which Leu305 or Phe374 have been replaced by another amino acid. At most 20 amino acids in the protease domain (153-406) have been replaced in combination with the above mentioned mutations. Other modified FVII molecules are disclosed which have optionally other amino acids replaced in positions 274, 300-304 and 306-312 in combination with Leu305 and Phe374. These modifications have the effect that FVIIa will spontaneously attain a more active conformation that normally has to be induced by TF.

Persson and Olsen (US 2003/0104978 and 2003/0100740, Sep. 29, 2000) further taught other modified FVIIa molecules with point mutations other than Ala substitutions at positions Lys157, Lys337, Asp334, Ser336, Val158, Glu296 and Met298.

Pingel and Klausen (US 2002/0151471 and US 2002/0137673, Oct. 2, 2000) claim a preparation comprising a plurality of FVII or related polypeptides, which comprise certain ratios of different N-type glycosylations.

Ruf et al. (WO 02/38162, Nov. 9, 2000) claimed FVII/FVIIa variants with the modifications Met298Gln, Glu296Ile and Val158Asn or combinations thereof leading to a higher amidolytic activity in the absence of TF and a higher affinity to TF. The factor was further modified to increase its stability in modifying the trypsin-like cleavage sites at Lys32, Lys38, Arg290, Arg304, Arg315 and Lys341 and the chymotrypsin-like sites at Ile42, Tyr44, Phe278 and Tyr332.

Persson (WO 02/077218, Mar. 22, 2001) teaches FVII/FVIIa mutants in which amino acids 247-260, 393-405 and Pro406 are mutated, more specifically R396, Q250 and Pro406, preferably an amino acid to which a chemical group can be attached with the goal of increasing the half life of FVII/FVIIa. This can be combined with mutations which increase the activity of FVII/FVIIa at K157, V158, E296, M298, L305, D334, S336, K337 and F374.

Persson and Olsen (US 2003/0100075, Sep. 27, 2001) teach that Leu305 is located at the end of an α-Helix found in the TF complexed form of FVIIa, which is believed to be important for the activity. In free FVIIa this helix is distorted and thus possibly unstable. Replacing Leu305 with other amino acids leads according to this invention to variants which attain the active conformation which otherwise is induced by TF. The amino acids Lys157, Lys337, Asp334, Ser336, Val 158, Glu296 and Met298 are located in areas which affect the formation of the salt bridge between Ile153 and Asp343. Replacing these amino acids leads according to this invention to the facilitation of the insertion of the N-terminus of the protease e.g. the generation of the salt bridge essential for activity.

Persson and Olsen (US 2003/0130191, Nov. 2, 2001) teach further modified FVII/VIIa mutants with increased specific activity which are substituted with other amino acids in positions: 313-329, 364, 366, 373 and 376 as well as in positions 330-339.

Haaning et al. (WO 03/093465, Apr. 30, 2002) extend the teaching of Nelsestuen (modification of the Gla Domain to enhance phospholipid binding), namely a substitution at Pro10 preferably Gln, Lys32 preferably Glu, Asp33 preferably a hydrophobic amino acid preferably Phe, Ala34 preferably a negatively charged amino acid preferably Glu and an insertion of an amino acid after Ala3 preferably Tyr with the introduction of further N-glycosylation sites.

Foncuberta et al. (WO 2004/011675, Jul. 25, 2002) describe naturally occurring allelic variants of FVII which could theoretically lead to higher expression levels and improved function of FVIIa. No data for such improved properties are shown. Two variants out of 49 were found in exons and lead to a substitution of amino acids: A294V and R353Q.

Persson and Olsen (WO 2004/029090, Sep. 25, 2002) showed that mutating Phe374 in combination with some other amino acids leads to an increase of TF independent activity of FVIIa. namely L305V, S314E, K337A and F374Y led to an increase of the TF amidolytic activity.

Haaning et al. (WO 2004/029091, Sep. 30, 2002) modified FVII at L39, I42, S43, K62, L65, F71, E82 and F275 in the TF binding site of FVII/FVIIa increasing the affinity to TF.

Andersen et al. (WO 2004/083361, Mar. 20, 2003) modified FVII/FVIIa in positions 196 (D196N/K), 237 (G237L or insertions GM GAAA or GAAA) and 341 (K341N/Q) to increase affinity to TF.

Blaichman et al. (WO 2004/108763, Jun. 5, 2003) modified FVII/FVIIa within the EGF domain based on an analysis of differences between the human and rabbit EGF domain as rabbit Factor VIIa has higher affinity to human TF as human Factor VIIa. Mutants in position 53, 62, 74, 75 and 83 are claimed and shown to have higher affinity to human TF and increased hemostatic potential.

Haaning et al (WO 2004/111242, Jun. 19, 2003) modified FVII/FVIIa at: positions 4, 10, 28, 32, 33, 34, 36, 74, 77, 116 preferably A3Y, P10Q, R28F, K32E, D33F, A34L, R36E, K38E, P74S, E77A, E116D. The R36E mutation causes reduced binding to TF and reduced thrombin generation in TF-dependent assays while maintaining in PL-dependent assays the same activity.

Johansen et al. (WO 2005/032581, Oct. 7, 2003) Teaches hybrid molecules consisting of a lipid membrane binding domain coupled to a Factor VII activity domain optionally coupled to a bulking agent, preferentially to PEG.

Maun et al. Protein Sci. (2005) 14:1171-80 introduced new disulfide bonds to lock the FVII conformation into an active TF*FVIIa-like state. Kinetic analysis of amidolytic activity revealed that all Factor VIIa variants alone had increased specific activity compared to wild type, the largest being for variants 136:160 and 138:160 with substrate S-2765, having 670- and 330-fold increases, respectively. Factor VIIa disulfide-locked variants no longer required TF as a co-factor for maximal activity in amidolytic assays. In the presence of soluble TF, activity was enhanced 20- and 12-fold for variants 136:160 and 138:160, respectively, compared to wild type.

DETAILED DESCRIPTION OF THE INVENTION

It is an object of the present invention to provide modified vitamin K-dependent polypeptides, e.g. modified FVII and modified FVIIa, with a longer functional half-life.

FVII is related to other Gla domain proteins like FIX, FX, protein C, protein Z, prothrombin, GAS6 and protein S. More closely related are FVII, FIX, FX and protein C in which the N-terminal Gla domain is followed by two epidermal growth factor (EGF) domains followed by the trypsin-type serine protease domain. Protein Z has a similar structure but an inactive protease domain. In prothrombin the Gla domain is followed by two kringle domains instead the two EGF domains then followed by the trypsin-type protease domain. In GAS6 and protein S the Gla domain is followed by 4 EGF domains and then by two laminin-G domains instead of the protease domain.

Striking is the large difference in plasma half life of these closely related plasma proteins:

| | |
|---|---|
| FVII | 2-4 hours |
| Protein C: | 6-8 hours |
| FIX: | 18-30 hours |
| FX: | 20-42 hours |
| Protein S: | 24-58 hours |
| Prothrombin: | 41-72 hours |

A particular closely related subgroup of these proteins comprises FVII, FIX, FX and protein C.

In FIG. 1 the homology between FVII, protein C, FIX and FX of human origin and of other species is compared. The molecules are highly conserved, the most striking difference being within the activation domain. For FVII no activation peptide has been described. However, during activation FVII might in addition to cleavage at Arg152 also be cleaved at Arg144, then resulting in the release of a putative activation peptide of 8 amino acids containing a conserved N-glycosylation site.

Surprisingly the length of the activation peptides and post-translational modifications of the activation peptides correlate with increased half-life:

TABLE 1

| | Plasma half-life | Length of human activation peptide | N-glycosylation sites within activation peptide |
|---|---|---|---|
| FVII | 2-4 hours | No activation peptide (or putative 8 amino acid activation peptide) | 1 in putative 8 amino acid activation peptide |
| Protein C | 6-8 hours | 11 amino acids | 0 |
| FIX | 18-30 hours | 35 amino acids | 2 |
| FX | 20-42 hours | 52 amino acids | 2 |

The invention therefore relates to a method for preparing a modified vitamin K-dependent polypeptide, comprising modifying the activation peptide of a first vitamin K-dependent polypeptide such that the modified vitamin K-dependent polypeptide has an increased half-life compared to the first vitamin K-dependent polypeptide in which the activation peptide has not been modified.

The invention further relates to a method for preparing such a modified vitamin K-dependent polypeptide, comprising modifying the activation peptide of a first vitamin K-dependent polypeptide by adding at least part of an activation peptide of a second vitamin K-dependent polypeptide or by replacing at least part of an activation peptide of a first vitamin K-dependent polypeptide with at least part of an activation peptide of a second vitamin K-dependent polypeptide.

Vitamin K-dependent polypeptides are a group of proteins that need vitamin K in their biosynthetic pathways to carboxylate the side chains of glutamic acid residues of their protein precursors. Vitamin K-dependent polypeptides include, but are not limited to, Factor VII, Factor VIIa, Factor IX, Factor IXa, Factor X, Factor Xa, Factor II (Prothrombin), Protein C, activated Protein C, Protein S, activated Protein S, GAS6, activated GAS6, Protein Z, activated Protein Z, and the like. Furthermore, useful vitamin K-dependent polypeptides can be wild-type or can contain mutations. Degree and location of glycosylation or other post-translation modifications may vary depending on the chosen host cells and the nature of the host cellular environment. When referring to specific amino acid sequences, posttranslational modifications of such sequences are encompassed in this application.

"Factor VII/VIIa" as used in this application means a product consisting of either the nonactivated form (factor VII) or the activated form (factor VIIa) or mixtures thereof. "Factor VII/VIIa" within the above definition includes proteins that have the amino acid sequence of native human factor VII/VIIa. It also includes proteins with a slightly modified amino acid sequence, for instance, a modified N-terminal end including N-terminal amino acid deletions or additions so long as those proteins substantially retain the activity of factor VIIa. "Factor VII" within the above definition also includes natural allelic variations that may exist and occur from one individual to another. "Factor VII" within the above definition further includes variants of FVII/FVIIa. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table.

TABLE 2

| (1) Alanine | Glycine | | |
|---|---|---|---|
| (2) Aspartic acid | Glutamic acid | | |
| (3) Asparagine | Glutamine | Serine | Threonine |
| (4) Arginine | Histidine | Lysine | |
| (5) Isoleucine | Leucine | Methionine | Valine |
| (6) Phenylalanine | Tyrosine | Tryptophane | |

The amino acid sequences of various vitamin K-dependent polypeptides and the cDNA sequences encoding them are shown in the sequence listing:

TABLE 3

| Vitamin K-dependent polypeptide | SEQ ID NO: of cDNA sequence | SEQ ID NO: of amino acid sequence encoded by cDNA | SEQ ID NO: of mature polypeptide |
|---|---|---|---|
| human Factor VII | 1 | 2 | 3 |
| human Protein C | 4 | 5 | 6 |
| human Factor IX | 7 | 8 | 9 |
| human Factor X | 10 | 11 | 12 |
| human Prothrombin | 13 | 14 | 15 |

The first vitamin K-dependent polypeptide is preferably selected from the group consisting of Factor VII, Factor VIIa, Factor IX, Factor IXa, Protein C and activated Protein C. More preferably, the first vitamin K-dependent polypeptide is selected from the group consisting of human Factor VII, human Factor VIIa, human Factor IX, human Factor IXa, human Protein C and human activated Protein C. Most preferably, the first vitamin K-dependent polypeptide is human Factor VII or human Factor VIIa. In a specific embodiment, the first vitamin K-dependent polypeptide comprises an amino acid sequence selected from the group consisting of SEQ ID NOs: 3, 6 and 9.

The second vitamin K-dependent polypeptide is different from the first vitamin K-dependent polypeptide. Accordingly, the modified vitamin K-dependent polypeptide obtainable by the process of the invention comprises at least part of an activation peptide not naturally occurring in the first vitamin K-dependent polypeptide.

The second vitamin K-dependent polypeptide has a longer plasma half life than the first vitamin K-dependent polypeptide. In another embodiment, the length of the activation peptide of the second vitamin K-dependent polypeptide is greater than the length of the activation peptide of the first vitamin K-dependent polypeptide. Preferably, the second vitamin K-dependent polypeptide is selected from the group consisting of Factor IX, Factor X and Prothrombin. More preferably, the second vitamin K-dependent polypeptide is selected from the group consisting of human Factor IX, human Factor X and human Prothrombin. In a specific embodiment, the second vitamin K-dependent polypeptide comprises an amino acid sequence selected from the group consisting of SEQ ID NOs:9, 12 and 15.

The part of the activation peptide of the activation peptide of the second vitamin K-dependent polypeptide, which is added, preferably consists of at least 8, more preferably of at least 12, even more preferably of at least 15 contiguous amino acids in the amino acid sequence of the activation peptide of the second vitamin K-dependent polypeptide.

In another embodiment the part of the activation peptide of the second vitamin K-dependent polypeptide, which is added, may consist of at least $0.15 \cdot N$ contiguous amino acids in the amino acid sequence of the activation peptide of the second vitamin K-dependent polypeptide, wherein N is the total number of amino acids of the activation peptide of the second vitamin K-dependent polypeptide. Preferably, the part of the activation peptide of the second vitamin K-dependent polypeptide consists of at least $0.5 \cdot N$, more preferably of at least $0.75 \cdot N$, more preferably of at least $0.9 \cdot N$, most preferably of at least $0.95 \cdot N$ contiguous amino acids in the amino acid sequence of the activation peptide of the second vitamin K-dependent polypeptide.

In another embodiment, the part of the activation peptide of the second vitamin K-dependent polypeptide, which is added, consists of at least (N-x) contiguous amino acids in the amino acid sequence of the activation peptide of the second vitamin K-dependent polypeptide, wherein N is the total number of amino acids of the activation peptide of the second vitamin K-dependent polypeptide and wherein x may be 7, preferably x is 5, more preferably x is 4, more preferably x is 3, even more preferably x is 2.

It is also possible that the part of the activation peptide of the second vitamin K-dependent polypeptide, which is added, consists of a central part of the activation peptide, i.e. it does not comprise the very C-terminal amino acid or the very N-terminal amino acid of the activation peptide.

Most preferably, the complete activation peptide of the second vitamin K-dependent polypeptide is added to the amino acid sequence of the first vitamin K-dependent polypeptide while retaining the specificity of activation of the first vitamin K-dependent polypeptide. Alternatively, a variant of the complete activation peptide of the second vitamin K-dependent polypeptide may be added to the amino acid sequence of the first vitamin K-dependent polypeptide. Variants include activation peptides in which 1 to 10, preferably 1 to 7, more preferably 1 to 5, most preferably 1 to 3 amino acids have been added, deleted and/or substituted.

If only the half-life of the zymogen shall be prolonged N- and C-terminal activation cleavage sites of the first vitamin K-dependent polypeptide are preferably retained in the variant activation peptides. If also the half-life of the activated form of the vitamin K-dependent polypeptide shall be prolonged either an N- or C-terminal activation cleavage site of the first vitamin K-dependent polypeptide shall be deleted. Preferably, the N-terminal activation cleavage site is deleted. If the half-life of FVIIa shall be prolonged preferentially N-terminal activation cleavage sites shall be deleted whereas preferentially C-terminal activation cleavage sites shall be retained.

The following table summarizes the sequences of activation peptides from several vitamin K-dependent polypeptides.

TABLE 4

| vitamin K-dependent polypeptide | amino acid sequence of activation peptide | SEQ ID NO: of activation peptide |
|---|---|---|
| human Factor VII | NASKPQGR (putative)<br>(aa 145-152 of SEQ ID NO: 3) | 16 |
| human Protein C | TEDQEDQVDPR<br>(aa 159-169 of SEQ ID NO: 6) | 17 |
| human Factor IX | AETVFPDVDYVNSTEAETILDNITQSTQSFNDFTR<br>(aa 146-180 of SEQ ID NO: 9) | 18 |
| human Factor X | SVAQATSSSGEAPDSITWKPYDAADLDPTE<br>NPFDLLDFNQTQPERGDNNLTR<br>(aa 143-194 of SEQ ID NO: 12) | 19 |
| human Prothrombin | TATSEYQTFFNPRTFGSGEADCGLRPLFEKKSLE<br>DKTERELLESYIDGR<br>(aa 272-320 of SEQ ID NO: 15) | 20 |

The term "activation peptide" as used herein includes known activation peptides and putative activation peptides such as that in Factor VII.

By way of non-limiting example, any one of the following amino acid sequences can be added to the amino acid sequence of SEQ ID NO:3 or 6
  aa 1 to 35 of SEQ ID NO:18;
  aa 1 to 34 of SEQ ID NO:18;
  aa 1 to 33 of SEQ ID NO:18;
  [ ... ]
  aa 1 to 8 of SEQ ID NO:18;
  aa 1 to 7 of SEQ ID NO:18;
  aa 1 to 6 of SEQ ID NO:18;
  aa 1 to 5 of SEQ ID NO:18;
  aa 2 to 35 of SEQ ID NO:18;
  aa 2 to 34 of SEQ ID NO:18;
  aa 2 to 33 of SEQ ID NO:18;
  [ ... ]
  aa 2 to 9 of SEQ ID NO:18;
  aa 2 to 8 of SEQ ID NO:18;
  aa 2 to 7 of SEQ ID NO:18;
  aa 2 to 6 of SEQ ID NO:18;
  aa 3 to 35 of SEQ ID NO:18;
  aa 3 to 34 of SEQ ID NO:18;
  aa 3 to 33 of SEQ ID NO:18;
  [ ... ]
  aa 3 to 10 of SEQ ID NO:18;
  aa 3 to 9 of SEQ ID NO:18;
  aa 3 to 8 of SEQ ID NO:18;
  aa 3 to 7 of SEQ ID NO:18;
  and so forth.

By way of non-limiting example, any one of the following amino acid sequences can be added to the amino acid sequence of SEQ ID NO:3, 6 or 9
  aa 1 to 52 of SEQ ID NO:19;
  aa 1 to 51 of SEQ ID NO:19;
  aa 1 to 50 of SEQ ID NO:19;
  [ ... ]
  aa 1 to 8 of SEQ ID NO:19;
  aa 1 to 7 of SEQ ID NO:19;
  aa 1 to 6 of SEQ ID NO:19;
  aa 1 to 5 of SEQ ID NO:19;
  aa 2 to 52 of SEQ ID NO:19;
  aa 2 to 51 of SEQ ID NO:19;
  aa 2 to 50 of SEQ ID NO:19;
  [ ... ]
  aa 2 to 9 of SEQ ID NO:19;
  aa 2 to 8 of SEQ ID NO:19;
  aa 2 to 7 of SEQ ID NO:19;
  aa 2 to 6 of SEQ ID NO:19;
  aa 3 to 52 of SEQ ID NO:19;
  aa 3 to 51 of SEQ ID NO:19;
  aa 3 to 50 of SEQ ID NO:19;
  [ ... ]
  aa 3 to 10 of SEQ ID NO:19;
  aa 3 to 9 of SEQ ID NO:19;
  aa 3 to 8 of SEQ ID NO:19;
  aa 3 to 7 of SEQ ID NO:19;
  and so forth.

The part of or the complete activation peptide of the second vitamin K-dependent polypeptide is inserted in the vicinity of the activation peptide region of the first vitamin K-dependent polypeptide. It may be inserted between two amino acids of the first vitamin K-dependent polypeptide without deleting amino acids of the first vitamin K-dependent polypeptide. For example, in case of FVII being the first vitamin K-dependent polypeptide, the part of or the complete activation peptide of the second vitamin K-dependent polypeptide may be inserted between amino acids 144 and 145, between amino acids 145 and 146, between amino acids 146 and 147, between amino acids 147 and 148, between amino acids 148 and 149, between amino acids 149 and 150, between amino acids 150 and 151, between amino acids 151 and 152 or between amino acids 152 and 153, wherein the numbering refers to SEQ ID NO:3. Preferably, the part of or the complete activation peptide of the second vitamin K-dependent polypeptide is inserted between amino acids 144 and 145, wherein the numbering refers to SEQ ID NO:3. Preferably, the C-terminal cleavage site and the specificity of activation of the first vitamin K-dependent polypeptide is preserved by the insertion. The N-terminal cleavage site may be deleted by the insertion.

In another aspect, the part of or the complete activation peptide of the second vitamin K-dependent polypeptide replaces a stretch of amino acids in the first vitamin K-dependent polypeptide. For example, in case of FVII being the first vitamin K-dependent polypeptide, the part of or the complete activation peptide of the second vitamin K-dependent polypeptide may replace amino acids 140 to 152 of SEQ ID NO:3. Preferably, the C-terminal cleavage site and the specificity of activation of the first vitamin K-dependent polypeptide is preserved by the replacement. The N-terminal cleavage site may be deleted by the replacement.

The N-terminal cleavage site may be deleted by replacing certain amino acids of the first vitamin K-dependent polypeptide with the part of or the complete activation peptide of the second vitamin K-dependent polypeptide. Accordingly, the part of or the complete activation peptide of the second vitamin K-dependent polypeptide may replace any one of the following amino acid sequences of SEQ ID NO:3:

aa 140 to 145;
aa 141 to 145;
aa 142 to 145;
aa 143 to 145;
aa 144 to 145;
aa 145;
aa 140 to 144;
aa 141 to 144;
aa 142 to 144;
aa 143 to 144; or
aa 144.

In another embodiment, the proteolytic cleavage sites in the first vitamin K-dependent polypeptide, which are N-terminal and C-terminal to the activation peptide region are retained during the modification. Thus the specificity of activation of the first vitamin K-dependent polypeptide is retained.

In another embodiment if the plasma half-life of the zymogen shall be prolonged the N-terminal and C-terminal activation cleavage sites of the second vitamin K-dependent polypeptide replace those of the first vitamin K-dependent polypeptide or an N-terminal activation cleavage site can be retained from the first vitamin K-dependent polypeptide and a C-terminal activation cleavage site can be retained from the second vitamin K-dependent polypeptide or vice versa. If the plasma half-life of the activated vitamin K-dependent polypeptide shall be stabilized either an N-terminal or a C-terminal activation cleavage site shall be deleted. In case of a stabilized FVIIa variant the activation peptide must be retained with the N-terminal light chain. This implies that the C-terminal activation cleavage site must be retained whereas an N-terminal activation cleavage site transferred from a vitamin K-dependent polypeptide must be deleted. Also it might be necessary to delete the hypothetical activation peptide cleavage site at Arg144.

The modification may further comprise in addition to the insertion of the activation peptide of a second vitamin K-dependent polypeptide or a variant thereof the concomitant deletion of at least part of the activation peptide of the first vitamin K-dependent polypeptide while preferentially retaining the specificity of activation of the first vitamin K-dependent polypeptide. The part to be deleted may consist of at least 2, preferably at least 4, more preferably at least 6, even more preferably at least 8 contiguous amino acids of the activation peptide of the first vitamin K-dependent polypeptide.

In another embodiment the part of the activation peptide of the first vitamin K-dependent polypeptide, which is deleted, may consist of at least 0.15·N contiguous amino acids in the amino acid sequence of the activation peptide of the first vitamin K-dependent polypeptide, wherein N is the total number of amino acids of the activation peptide of the first vitamin K-dependent polypeptide. Preferably, the part of the activation peptide of the first vitamin K-dependent polypeptide consists of at least 0.5·N, more preferably of at least 0.75·N, more preferably of at least 0.9·N, most preferably of at least 0.95·N contiguous amino acids in the amino acid sequence of the activation peptide of the first vitamin K-dependent polypeptide.

In another embodiment, the part of the activation peptide of the first vitamin K-dependent polypeptide, which is deleted, consists of at least (N-x) contiguous amino acids in the amino acid sequence of the activation peptide of the first vitamin K-dependent polypeptide, wherein N is the total number of amino acids of the activation peptide of the first vitamin K-dependent polypeptide, wherein x may be 7, preferably x is 5, more preferably x is 4, more preferably x is 3, even more preferably x is 2.

It is also possible that the part of the activation peptide of the first vitamin K-dependent polypeptide, which is deleted, consists of a central part of the activation peptide, i.e. it does not comprise the very C-terminal amino acid or the very N-terminal amino acid of the activation peptide.

In a specific embodiment, the complete activation peptide of the first vitamin K-dependent polypeptide is deleted.

Usually, the modification comprises replacing at least part of the activation peptide of the first vitamin K-dependent polypeptide with at least part of the activation peptide of the second vitamin K-dependent polypeptide. The preferred embodiments of the parts of the activation peptide of the first vitamin K-dependent polypeptide and of the activation peptide of the second vitamin K-dependent polypeptide correspond to those described above.

In a particular embodiment, the complete activation peptide of the first vitamin K-dependent polypeptide is replaced with the complete activation peptide of the second vitamin K-dependent polypeptide or with a variant of the complete activation peptide of the second vitamin K-dependent polypeptide while retaining the amino acids necessary to retain the specificity of activation of the first vitamin K-dependent polypeptide.

By way of non-limiting example the invention encompasses the introduction of activation peptide sequences from animal vitamin K-dependent polypeptides (some of which are shown in FIG. 1), such as murine, canine, bovine, porcine or rodent prothrombin factors, as well as combinations thereof.

By way of non-limiting example the invention encompasses the introduction of the activation peptide of FIX or FX into the vicinity of the activation site of FVII, as well as replacing the activation peptide of protein C by that of FIX or FX, as well as replacing the activation peptide of FIX by that of FX. By way of illustrating the breadth of this aspect of the invention with the preferred FVII molecule the half life of FVII is increased by simply replacing the putative activation peptide of 8 amino acids completely by one of the activation peptides taken from protein C, FIX or FX or by creating a hybrid activation peptide by adding the activation peptides taken from protein C, FIX or FX to, from one amino terminus proximal amino acid up to the complete putative FVII activation peptide.

Another aspect of the invention is the variation of the post translational modification of these transferred activation peptides, as by way of non-limiting example the removal of N-glycosylation sites in the transferred activation peptides or alternatively the removal of the N-glycosylation site in the putative activation peptide of FVII between Arg144 and Arg152, can lead to less asialoprotein-receptor mediated clearance of the coagulation factor. In one embodiment of the invention, the modification therefore comprises modifying sites of posttranslational modification within the activation peptide. Preferably, the modification comprises removing at least one N-glycosylation site within the activation peptide.

Another aspect of the invention is the prolongation of plasma half-life by the transfer of analogues of the activation peptides of longer-lived vitamin K-dependent proteins. An analogue in its widest sense is an insert having longer than 8 continuous amino acids or conservative substitutions of these amino acids of the activation peptide of a longer lived wild-type vitamin K-dependent protein while preserving its N- and its C-terminal activation cleavage sites if the half-life of the zymogen of the first vitamin K-dependent polypeptide shall be prolonged or while preserving either its N- or its C-terminal activation cleavage site if also the half-life of the activated vitamin K-dependent polypeptide shall be prolonged.

Conservative amino acid substitutions are substitutions performed within groups of amino acids with similar characteristics, e.g. (1) small amino acids, (2) acidic amino acids, (3) polar amino acids, (4) basic amino acids, (5) hydrophobic amino acids and (6) aromatic amino acids. Examples of such conservative substitutions are shown in table 2.

Another aspect of the invention is a method for increasing the stability of a vitamin K-dependent polypeptide, comprising modifying its activation peptide. Yet another aspect of the invention is a method for increasing the functional half life or plasma half-life of a vitamin K-dependent polypeptide, comprising modifying its activation peptide. These methods may comprise the same steps as the method for producing a modified vitamin K-dependent polypeptide described above.

The invention further relates to a modified vitamin K-dependent polypeptide obtainable by a process of the invention. The modified vitamin K-dependent polypeptide may comprise a modified activation peptide, wherein the modified vitamin K-dependent polypeptide has an increased half-life compared to the vitamin K-dependent polypeptide in which the activation peptide has not been modified.

Another aspect of the invention is a modified vitamin K-dependent polypeptide comprising a modified activation peptide, said modified activation peptide comprising at least part of an activation peptide of a different vitamin K-dependent polypeptide. Alternatively, the modified vitamin K-dependent polypeptide may comprise an analogue or a variant of an activation peptide of a different vitamin K-dependent polypeptide. Analogues and variants are molecules as defined supra.

Preferably, the vitamin K-dependent polypeptide is a first vitamin K-dependent polypeptide as defined supra. The "different vitamin K-dependent polypeptide" is a second vitamin K-dependent polypeptide as defined supra. The preferred embodiments of the modified vitamin K-dependent polypeptide of the invention correspond to the preferred embodiments described hereinbefore with respect to the method of the invention.

In another embodiment, the modified vitamin K-dependent polypeptide of the invention exhibits an increased functional half-life compared to the non-modified form and/or to the wild type form of the vitamin K-dependent polypeptide. The functional half-life can be determined in vitro as shown in Lindley et al. (Pharmacokinetics and pharmacodynamics of recombinant Factor VIIa, Clin. Pharmacol Ther. 1994 55:638-648)

The functional half life is usually increased by at least 50%, preferably by at least 100%, more preferably by at least 200%, even more preferably by at least 500% compared to the non-modified form and/or to the wild type form of the vitamin K-dependent polypeptide.

The functional half life of the wild type form of human Factor VII is approximately 4 hours. The functional half life of the modified Factor VII molecule of the invention is usually at least about 6 hours, preferably at least about 10 hours, more preferably at least about 15 hours, most preferably at least about 24 hours.

The functional half life of the wild type form of human Factor VIIa is approximately 2 hours. The functional half life of the modified Factor VIIa molecule of the invention is usually at least about 3 hours, preferably at least about 5 hours, more preferably at least about 8 hours, most preferably at least about 12 hours.

Generally, the modified vitamin K-dependent polypeptide has an increased stability compared to the non-modified form and/or compared to the wild type form of the vitamin K-dependent polypeptide. An increase in stability of the modified Factor VII molecules can for example be measured as previously described by functional assays The modified vitamin K-dependent polypeptide of the invention usually has substantially the same activity as the corresponding wild type form and/or non-modified form of the vitamin K-dependent polypeptide. A "substantially the same" activity means at least about 10%, preferably about 50%, more preferably at least about 75%, most preferably at least about 100% of the activity of the corresponding wild type form and/or non-modified form of the vitamin K-dependent polypeptide. The activity of Factor VII/VIIa is the ability to convert the substrate Factor X to the active Factor Xa. The activity of a Factor VII/VIIa polypeptide may be measured with the assays described in Shaw et al., 1998, PNAS, Vol. 95, pp. 4229-4234 or as in Gabriel et al. 2004, Sem. Hematol. Vol 41, Suppl. 1 pp 20-24.

The invention further relates to a polynucleotide encoding a modified vitamin K-dependent polypeptide as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing a modified vitamin K-dependent polypeptide, which is part of this invention. The method comprises:
(a) culturing host cells of the invention under conditions such that the modified vitamin K-dependent polypeptide is expressed; and
(b) optionally recovering the modified vitamin K-dependent polypeptide from the host cells or from the culture medium.

Expression of the Proposed Variants:

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the hybrid, modified Gla domain proteins, preferably FIX, FX, protein C most preferred Factor VII proteins. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are tyrosine O-sulfation, hydroxylation and proteolytic processing of the nascent polypeptide chain. Examples of cell lines that can be use are monkey COS-cells, mouse L-cells, mouse C127-cells, hamster BHK-21 cells, human embryonic kidney 293 cells, and preferentially hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody which is immobilised on a solid support. After desorption, the protein can be further purified by a variety of chromatographic techniques based on the above properties.

It is preferred to purify the modified vitamin K-dependent polypeptide of the present invention to >80% purity, more preferably >95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified vitamin K-dependent polypeptide of the invention is substantially free of other polypeptides.

The recombinant proteins described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

The various products of the invention are useful as medicaments. Accordingly, the invention relates to a pharmaceutical composition comprising a modified vitamin K-dependent polypeptide as described herein, a polynucleotide of the invention, or a plasmid or vector of the invention.

The modified DNA's of this invention may also be integrated into a transfer vector for use in the human gene therapy.

Another aspect of the invention is the use of a modified vitamin K-dependent polypeptide as described herein, of a polynucleotide of the invention, of a plasmid or vector of the invention, or of a host cell of the invention for the manufacture of a medicament for the treatment or prevention of a blood coagulation disorder. Blood coagulation disorders include but are not limited to hemophilia A. Preferably, the treatment comprises human gene therapy.

The invention also concerns a method of treating an individual suffering from a blood coagulation disorder such as hemophilia A. The method comprises administering to said individual an efficient amount of the modified vitamin K-dependent polypeptide as described herein. In another embodiment, the method comprises administering to the individual an efficient amount of the polynucleotide of the invention or of a plasmid or vector of the invention. Alternatively, the method may comprise administering to the individual an efficient amount of the host cells of the invention described herein.

DESCRIPTION OF THE DRAWINGS

Figure 1B:
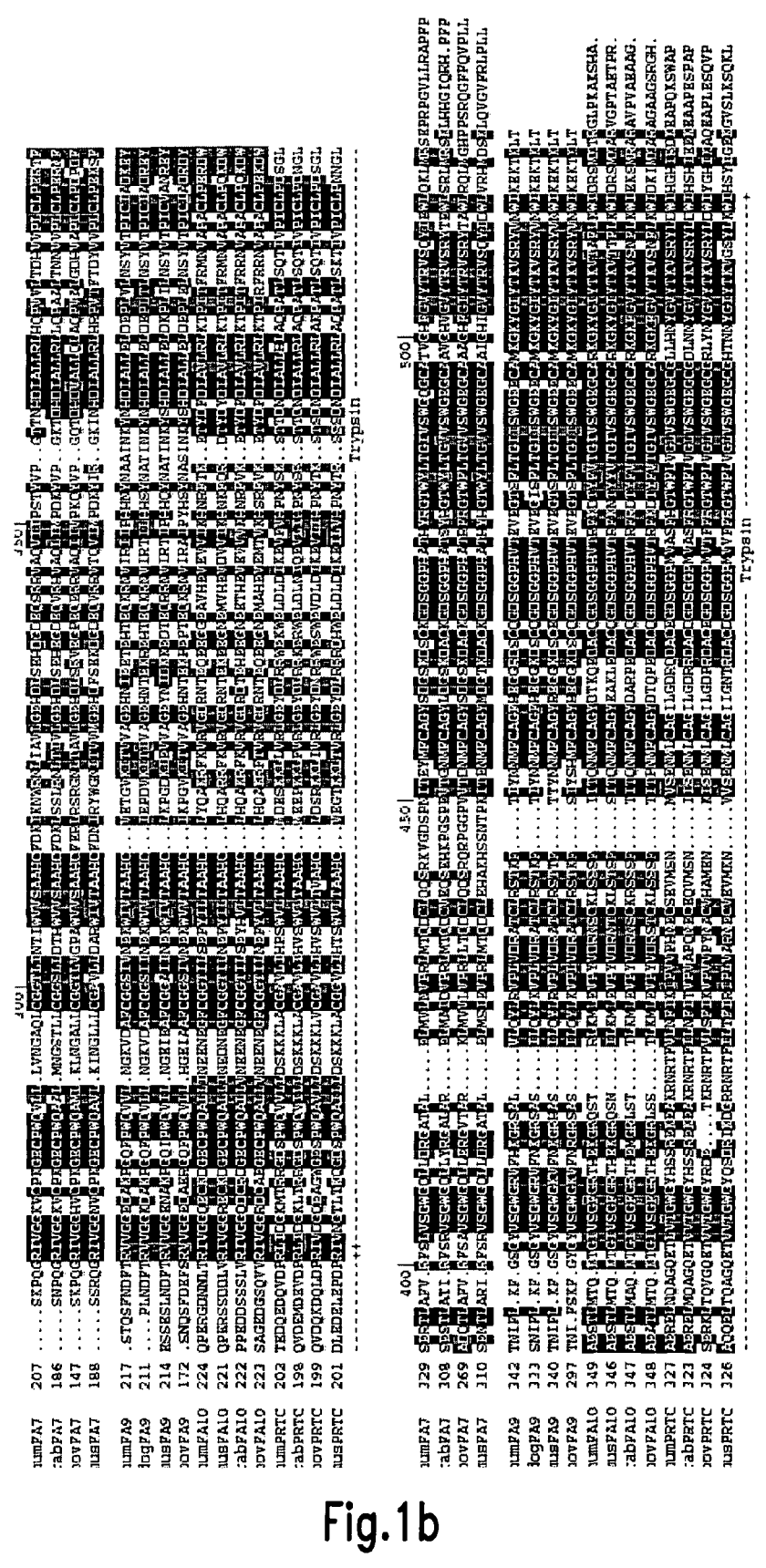

FIG. 1 discloses SEQ ID NOS 54-69, respectively, in order of appearance.

EXAMPLES

Figure 1A:
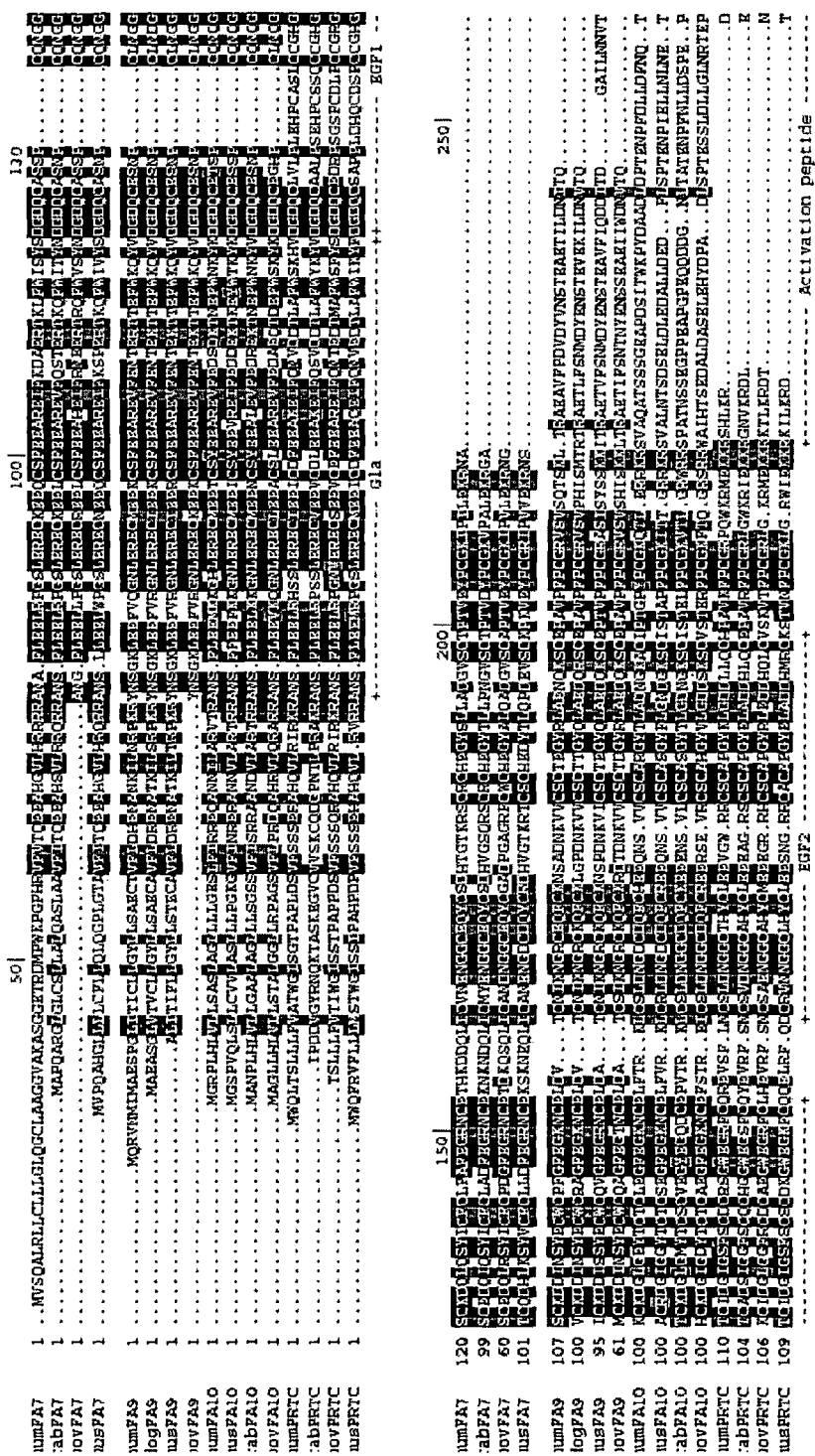
FIG. 1: Homology comparison between FVII, protein C, FIX and FX of human origin and of other species.

The present invention will be further described more in detail in the following examples thereof. This description of specific embodiments of the invention will be made in conjunction with the appended figures.

Example 1

Insertion of the Factor IX Activation Peptide Sequence into the Factor VII Coding Sequence

In this example the majority of the FIX activation peptide is inserted into the respective location in the FVII cDNA while preserving the FVII activation site. First, FVII cDNA, inserted into cloning vector pIRESpuro3 (Becton Dickinson; plasmid designated pFVII-538 wt) was prepared for insertion of foreign activation peptide sequences by introduction of a restriction site, NheI, between amino acids Ala146 and Ser147 (numbering refers to SEQ ID NO:3). Site directed mutagenesis was performed with a commercially available mutagenesis kit (e.g. Stratagene QuickChange SiteDirected Mutagenesis Kit) according to the manufacturer's instructions. Primers used for mutagenesis are listed below; mutagenic bases are indicated in bold letters.

```
forward primer
                                         (SEQ ID NO: 21)
5'CCTATTCTAGAAAAAAGAAATGCTAGCAAACCCCAAGGCCG3' reverse primer
                                         (SEQ ID NO: 22)
5'CGGCCTTGGGGTTTGCTAGCATTTCTTTTTTCTAGAATAGG3'
```

The resulting plasmid was designated pFVII-NheI186.

Second, amino acids 165 to 194 of the FIX activation peptide (numbering refers to SEQ ID NO:9) were amplified on a FIX cDNA construct by polymerase chain reaction using the following primers.

```
forward primer
                                         (SEQ ID NO: 23)
5'GTGGCTAGCGCTGAGACTGTTTTTCCTG3' reverse primer
                                         (SEQ ID NO: 24)
5'CACGCTAGCTTGGGTGCTTTGAGTGATG3'
```

Both primers added a NheI restriction site (underlined). The amplification product was digested with NheI and cloned into the NheI digested pFVII-NheI186 described above.

After verification of the correct orientation by DNA sequencing two rounds of mutagenesis were performed to backmutate the NheI sites into the natural FVII/FIX sequences. The mutagenic primers are indicated below:

Primers to Backmutate the NheI Site at the 5'-End of the FIX Insert:

```
forward primer
                                         (SEQ ID NO: 25)
5'CTAGAAAAAAGAAATGCTCGTGCTGAGACTGTTTTTCCTGATGTGG3' reverse primer
                                         (SEQ ID NO: 26)
5'CCACATCAGGAAAAACAGTCTCAGCACGAGCATTTCTTTTTTCTAG3'
```

Primers to Backmutate the NheI Site at the 3'-End of the FIX Insert:

```
forward primer
                                         (SEQ ID NO: 27)
5'CATCACTCAAAGCACCCAATCAAGCAAACCCCAAGGCCGAATTG3' reverse primer
                                         (SEQ ID NO: 28)
5'CAATTCGGCCTTGGGGTTTGCTTGATTGGGTGCTTTGAGTGATG3'
```

The resulting expression plasmid was designated pFVII-552. The resulting mature FVII/FIX chimeric protein sequence (SEQ ID NO:29) is given below, the inserted FIX activation peptide sequence being underlined.

```
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNARAET

151 VFPDVDYVNS TEAETILDNI TQSTQSSKPQ GRIVGGKVCP KGECPWQVLL
```

-continued
```
201 LVNGAQLCGG TLINTIWVVS AAHCFDKIKN WRNLIAVLGE HDLSEHDGDE

251 QSRRVAQVII PSTYVPGTTN HDIALLRLHQ PVVLTDHVVP LCLPERTFSE

301 RTLAFVRFSL VSGWGQLLDR GATALELMVL NVPRLMTQDC LQQSRKVGDS

351 PNITEYMFCA GYSDGSKDSC KGDSGGPHAT HYRGTWYLTG IVSWGQGCAT

401 VGHFGVYTRV SQYIEWLQKL MRSEPRPGVL LRAPFP 436
```

Depending on which cDNA sequences are being used for cloning, the chimeric protein may also contain polymorphisms of FVII and FIX like the FIX activation peptide RAE AVFPDVDYVNSTEAETILDNITQSTQS (SEQ ID NO:30) polymorphism.

Based on plasmid pFVII-552 another expression plasmid was constructed with different transition sequences between the FVII cDNA and the FIX activation peptide sequences. For that two rounds of mutagenesis were applied to pFVII-552 as described above. The first round deleted amino acids 145 to 147 of SEQ ID NO:29 and used the following primers:

```
forward primer
                                  (SEQ ID NO: 42)
5'CTATTCTAGAAAAAAGAGCTGAGACTGTTTTTCCTGATG3' reverse primer
                                  (SEQ ID NO: 43)
5'CATCAGGAAAAACAGTCTCAGCTCTTTTTTCTAGAATAG3'
```

The second round of mutagenesis inserted 4 amino acids between amino acids 176 and 177 of SEQ ID NO:29 and used the following primers:

```
forward primer
                                  (SEQ ID NO: 44)
5'CAAAGCACCCAATCAAAGCGGAATGCTAGCAAACCCCAAGG3' reverse primer
                                  (SEQ ID NO: 45)
5'CCTTGGGGTTTGCTAGCATTCCGCTTTGATTGGGTGCTTTG3'
```

The resulting plasmid was called pFVII-681. The resulting mature FVII/FIX chimeric protein sequence (SEQ ID NO:46) is given below, the inserted FIX activation peptide sequence being underlined.

Example 2

Insertion of the Factor X Activation Peptide Sequence into the Factor VII Coding Sequence The FX activation peptide was amplified by PCR on a cloned FX cDNA using the following primers, attaching an NheI restriction site (underlined).

```
forward primer
                                  (SEQ ID NO: 47)
5'GTGGCTAGCCAGGCCACCAGCAGCAG3' reverse primer
                                  (SEQ ID NO: 48)
5'GCGGCTAGCATTCCGCTTCTCAGGCTGCGTCTGGTTG3'
```

The PCR fragment containing the FX activation peptide was then digested with NheI and ligated into NheI digested plasmid pFVII-NheI186 (example 1). In 2 subsequent rounds of site-directed mutagenesis as described supra the transition between the FVII cDNA sequence and the FX activation peptide was corrected.

First Round of Mutagenesis was Performed with the Following Oligonucleotides:

```
forward primer
                                  (SEQ ID NO: 49)
5'CCTATTCTAGAAAAAAGAAATGCCCAGGCCACCAGCAGCAGCGG3' reverse primer
                                  (SEQ ID NO: 50)
5'CCGCTGCTGCTGGTGGCCTGGGCATTTCTTTTTTCTAGAATAGG3'
```

```
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRAETVFP

151 DVDYVNSTEA ETILDNITQS TQSKRNASKP QGRIVGGKVC PKGECPWQVL

201 LLVNGAQLCG GTLINTIWVV SAAHCFDKIK NWRNLIAVLG EHDLSEHDGD

251 EQSRRVAQVI IPSTYVPGTT NHDIALLRLH QPVVLTDHVV PLCLPERTFS

301 ERTLAFVRFS LVSGWGQLLD RGATALELMV LNVPRLMTQD CLQQSRKVGD

351 SPNITEYMFC AGYSDGSKDS CKGDSGGPHA THYRGTWYLT GIVSWGQGCA

401 TVGHFGVYTR VSQYIEWLQK LMRSEPRPGV LLRAPFP 437
```

Second Round of Mutagenesis was Performed with the Following Oligonucleotides:

forward primer
(SEQ ID NO: 51)
5'CCTATTCTAGAAAAAAGCGTGGCCCAGGCCACCAGCAGCAGCGGGG3' reverse primer
(SEQ ID NO: 52)
5'CCCCGCTGCTGCTGGTGGCCTGGGCCACGCTTTTTTCTAGAATAGG3'

The resulting plasmid was called pFVII-611. The resulting mature FVII/FX chimeric protein sequence (SEQ ID NO:53) is given below, the inserted FX activation peptide sequence being underlined.

```
  1  ANAFLEELRP GSLERECKEE QCSFEEAREI FKDAERTKLF WISYSDGDQC

51  ASSPCQNGGS CKDQLQSYIC FCLPAFEGRN CETHKDDQLI CVNENGGCEQ

101  YCSDHTGTKR SCRCHEGYSL LADGVSCTPT VEYPCGKIPI LEKSVAQATS

151  SSGEAPDSIT WKPYDAADLD PTENPFDLLD FNQTQPEKRN ASKPQGRIVG

201  GKVCPKGECP WQVLLLVNGA QLCGGTLINT IWVVSAAHCF DKIKNWRNLI

251  AVLGEHDLSE HDGDEQSRRV AQVIIPSTYV PGTTNHDIAL LRLHQPVVLT

301  DHVVPLCLPE RTFSERTLAF VRFSLVSGWG QLLDRGATAL ELMVLNVPRL

351  MTQDCLQQSR KVGDSPNITE YMFCAGYSDG SKDSCKGDSG GPHATHYRGT

401  WYLTGIVSWG QGCATVGHFG VYTRVSQYIE WLQKLMRSEP RPGVLLRAPF

451  P   452
```

Example 3

Insertion of the Factor X Activation Peptide Sequence into the Factor IX Coding Sequence In this example the FX activation peptide is inserted into the respective location in the FIX cDNA preserving the FIX activation site.

First, FIX cDNA in cloning vector pIRESpuro3 (Becton Dickinson) was prepared for insertion of foreign activation peptide sequences by introduction of two restriction sites: an XbaI site between amino acids Ser161 and Lys162 and a PinAI site between Thr192 and Gln193 (numbering refers to SEQ ID NO:9). Site directed mutagenesis was performed with a commercially available mutagenesis kit (e.g. Stratagene QuickChange SiteDirected Mutagenesis Kit) according to the manufacturer's instructions. Primers used for mutagenesis are listed below; mutagenic bases are indicated in bold letters.

Mutagenic Primers for Introduction of XbaI Site:

forward primer
(SEQ ID NO: 31)
5'GAAGAGTTTCTGTTTCACAAACTTCTAGACTCACCCGTGCTGAGAC3' reverse primer
(SEQ ID NO: 32)
5'GTCTCAGCACGGGTGAGTCTAGAAGTTTGTGAAACAGAAACTCTTC3'

Mutagenic Primers for Introduction of PinAI Site:

forward primer
(SEQ ID NO: 33)
5'GGATAACATCACTCAAAGCACCGGTTCATTTAATGACTTCACTCGGGTTG3' reverse primer
(SEQ ID NO: 34)
5'CAACCCGAGTGAAGTCATTAAATGAACCGGTGCTTTGAGTGATGTTATCC3'

Second, amino acids 159 to 213 of the FX activation peptide (numbering refers to SEQ ID NO:12) were amplified by polymerase chain reaction using following primers adding a 5'-terminal XbaI and a 3'-terminal PinAI site (underlined).

forward primer
5'GTGTCTAGAAGGAAGAGGTCAGTGGCCC3'   (SEQ ID NO: 35)

reverse primer
5'CACACCGGTGAGGTTGTTGTCGCCC3'   (SEQ ID NO: 36)

The amplification product was digested with XbaI and PinAI and cloned into the XbaI and PinAI digested FIX cDNA modified as described above. Two rounds of mutagenesis were subsequently performed to backmutate the XbaI and PinAI sites into the natural FIX and FX sequences. The mutagenic primers are indicated below:

Primers to Backmutate the XbaI Site at the 5'-End of the FX Insert:

```
forward primer
                                         (SEQ ID NO: 37)
5'GAGTTTCTGTTTCACAAACTTCTCGCAGGAAGAGGTCAGTGG3' reverse primer
                                         (SEQ ID NO: 38)
5'CCACTGACCTCTTCCTGCGAGAAGTTTGTGAAACAGAAACTC3'
```

Primers to Backmutate the PinAI Site at the 3'-End of the FX Insert:

```
forward primer
                                         (SEQ ID NO: 39)
5'GCGACAACAACCTCACCCAATCATTTAATGACTTCACTCGGGTTG3' reverse primer
                                         (SEQ ID NO: 40)
5'CAACCCGAGTGAAGTCATTAAATGATTGGGTGAGGTTGTTGTCGC3'
```

The resulting mature FIX/FX chimeric protein sequence (SEQ ID NO:41) is given below, the inserted FX activation peptide sequence being underlined.

```
  1 YNSGKLEEFV QGNLERECME EKCSFEEARE VFENTERTTE FWKQYVDGDQ

51 CESNPCLNGG SCKDDINSYE CWCPFGFEGK NCELDVTCNI KNGRCEQFCK

101 NSADNKVVCS CTEGYRLAEN QKSCEPAVPF PCGRVSVSQT SRRKRSVAQA

151 TSSSGEAPDS ITWKPYDAAD LDPTENPFDL LDFNQTQPER GDNNLTQSFN

201 DFTRVVGGED AKPGQFPWQV VLNGKVDAFC GGSIVNEKWI VTAAHCVETG

251 VKITVVAGEH NIEETEHTEQ KRNVIRIIPH HNYNAAINKY NHDIALLELD

301 EPLVLNSYVT PICIADKEYT NIFLKFGSGY VSGWGRVFHK GRSALVLQYL

351 RVPLVDRATC LRSTKFTIYN NMFCAGPHEG GRDSCQGDSG GPHVTEVEGT

401 SFLTGIISWG EECAMKGKYG IYTKVSRYVN WIKEKTKLT  439
```

Example 4

Transfection and Expression of Modified FVII and FIX Proteins

Expression plasmids were grown up in *E. coli* TOP10 (Invitrogen) and purified using standard protocols (Qiagen). HEK 293 cells (Invitrogen) were transfected using the Lipofectamine 2000 reagent (Invitrogen) and grown up in serum-free medium (Invitrogen 293 Express) in the presence of 50 ng/ml Vitamin K3 and 4 μg/ml Puromycin. Transfected cell populations were spread through T-flasks into roller bottles from which supernatant was harvested for purification.

Example 5

Purification of Modified FVII Proteins

FVII proteins were purified as described in patent EP 0770625. Briefly, soluble tissue factor was covalently coupled to sepharose beads by bromine cyanide. FVII containing cell culture supernatant was loaded in a 10 mM calcium buffer. Unbound proteins were washed away with the same buffer. Elution of bound FVII proteins was performed with a 100 mM sodium citrate buffer.

Example 6

Determination of FVII Activity and Antigen

FVII antigen was determined by an ELISA whose performance is known to those skilled in the art. Briefly, microplates were incubated with 120 μL per well of the capture antibody (sheep anti human FVII IgG, Cedarlane CL20030AP, diluted 1:1000 in Buffer A [Sigma C3041]) overnight at ambient temperature. After washing plates three times with buffer B (Sigma P3563), each well was incubated with 200 μL buffer C (Sigma P3688) for one hour at ambient temperature. After another three wash steps with buffer B, serial dilutions of the test sample in buffer B as well as serial dilutions of standard human plasma (Dade Behring; 50-0.5 mU/mL) in buffer B (volumes per well: 100 μL) were incubated for two hours at ambient temperature. After three wash steps with buffer B, 100 μL of a 1:5000 dilution in buffer B of the detection antibody (sheep anti human FVII IgG, Cedarlane CL20030K, peroxidase labelled) were added to each well and incubated for another two hours at ambient temperature. After three wash steps with buffer B, 100 μL of substrate solution (TMB, Dade Behring, OUVF) were added per well and incubated for 30 minutes at ambient temperature in the dark. Addition of 100 μL undiluted stop solution (Dade Behring, OSFA) prepared the samples for reading in a suitable microplate reader at 450 nm wavelength. Concentrations of test samples were then calculated using the standard curve with standard human plasma as reference.

Example 7

Pharmacokinetics of Modified FVII Proteins

Figure 2:
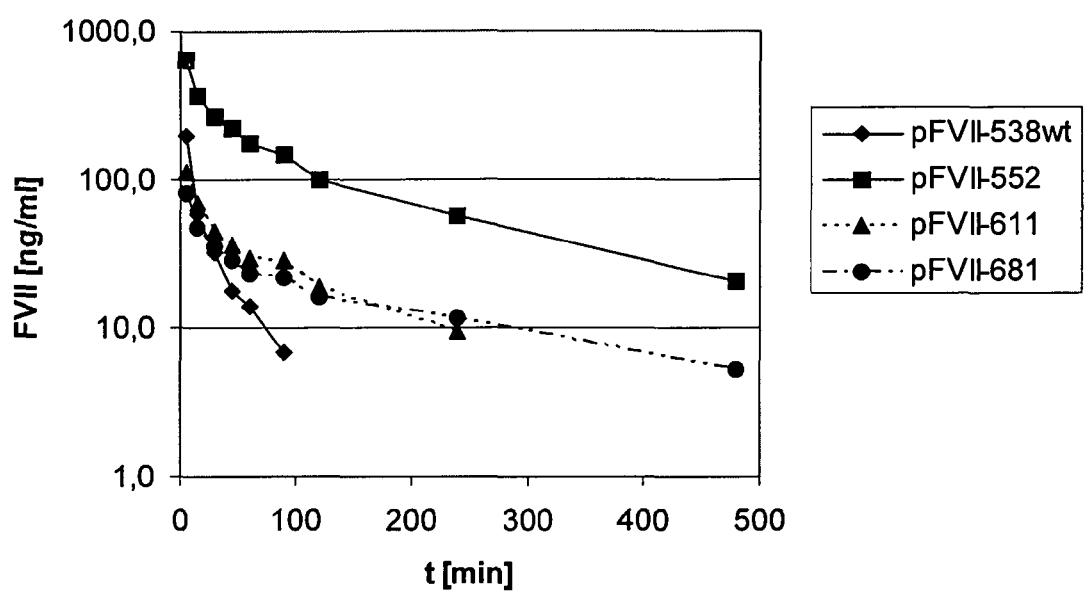
FIG. 2: Pharmacokinetics of FVII variants with inserted activation peptides from long lived vitamin-K dependent polypeptides

Wild-type and modified FVII proteins were administered intravenously to narcotised CD/Lewis rats (6 rats per substance) with a dose of 100 μg/kg body weight. Blood samples were drawn from 3 rats at 5, 30, 60, 120 and 480 minutes and from the other 3 rats at 15, 45, 90 and 240 minutes after application of the test substances from the arteria carotis. FVII antigen content was subsequently quantified by an ELISA assay specific for human factor VII (see above). The mean FVII antigen concentrations for each group are shown in FIG. 2. Table 5 summarizes the calculated half-lifes for the alpha and beta phases of elimination, whereby alpha phase was defined from 5 to 30 min and beta phase from 30 min to the last time point with concentrations above the limit of detection of the antigen assay. Calculations were done according to the formula $T_{1/2}$=ln 2/k, whereby k is the slope of the regression line.

| construct | half-life alpha phase [min] | half-life beta phase [min] | beta phase calculated from | half life extension (beta phase) compared to FVII wild-type |
|---|---|---|---|---|
| pFVII-538wt | 10 | 29 | 30-90 min | |
| pFVII-552 | 20 | 128 | 30-480 min | 4.4 fold |
| pFVII-611 | 19 | 102 | 30-240 min | 3.5 fold |
| pFVII-681 | 22 | 178 | 30-480 min | 6.1 fold |

The data clearly show that replacement of the native putative FVII activation peptide by an activation peptide from longer-lived prothrombin factors significantly extended the proteins' in vivo half-lifes compared to the wild-type FVII protein.

The invention claimed is:

1. A modified human Factor VII, human Factor VIIa, or human Factor IX polypeptide having a lengthened activation domain amino acid sequence as compared to a corresponding unmodified, native human Factor VII, human Factor VIIa, or human Factor IX, the modified polypeptide comprising
(a) a human Factor VII, human Factor VIIa, or human Factor IX polypeptide wherein all or a portion of an activation domain from human Factor IX, human Factor X, or human Prothrombin is inserted into the native activation domain of the human Factor VII, human Factor VIIa, or human Factor IX polypeptide, such that the modified polypeptide has a lengthened activation domain amino acid sequence; or
(b) a human Factor VII, human Factor VIIa, or human Factor IX polypeptide wherein all or a portion of the native activation domain is removed and all or a portion of an activation domain from human Factor IX, human Factor X, or human Prothrombin is inserted, such that the modified polypeptide has a lengthened activation domain amino acid sequence;
wherein the modified human Factor VII, human Factor VIIa, or human Factor IX polypeptide is modified only in the activation domain and has an increased half-life as compared to the unmodified, native human Factor VII, human Factor VIIa, or human Factor IX.

2. The modified polypeptide of claim 1, wherein the modified polypeptide does not contain an N-glycosylation site within its activation peptide.

3. The modified polypeptide of claim 1, wherein the half-life of the modified polypeptide is increased by at least 50%, as compared to the corresponding unmodified polypeptide.

4. The modified polypeptide of claim 1, wherein the modified polypeptide has increased stability in an in vitro functional assay, as compared to the corresponding unmodified polypeptide.

5. The modified polypeptide of claim 1, wherein the modified polypeptide has coagulant activity, as measured in an in vitro coagulation assay.

6. The modified polypeptide of claim 1, wherein: (i) the activation peptide of the modified polypeptide is capable of being cleaved off during activation, and/or (ii) the zymogen form of the modified polypeptide has an increased half-life as compared to the zymogen form of the corresponding unmodified polypeptide.

7. The modified polypeptide of claim 1, wherein: (i) the activation peptide of the modified polypeptide is not capable of being cleaved off during activation, and/or (ii) the activated form of the modified polypeptide has an increased half-life as compared to the activated form of the corresponding unmodified polypeptide.

8. The modified polypeptide of claim 1, comprising an activation domain from human Factor IX, human Factor X, or human Prothrombin in which 1 to 7 amino acids have been added, deleted, and/or substituted.

9. The modified polypeptide of claim 1, comprising an activation domain from human Factor IX, human Factor X, or human Prothrombin in which 1 to 5 amino acids have been added, deleted, and/or substituted.

10. The modified polypeptide of claim 1, comprising an activation domain from human Factor IX, human Factor X, or human Prothrombin in which 1 to 3 amino acids have been added, deleted, and/or substituted.

11. The modified polypeptide of claim 1, wherein the activation domain of the modified polypeptide comprises side chains with glutamic acid residues that can be carboxylated.

12. The modified polypeptide of claim 1, wherein at least 2 contiguous amino acids have been deleted from the native activation peptide.

13. The modified polypeptide of claim 1, wherein at least 4 contiguous amino acids have been deleted from the native activation peptide.

14. The modified polypeptide of claim 1, wherein at least 6 contiguous amino acids have been deleted from the native activation peptide.

15. The modified polypeptide of claim 1, wherein at least 8 contiguous amino acids have been deleted from the native activation peptide.

16. The modified polypeptide of claim 1, wherein at least 8 contiguous amino acids from the activation peptide of human Factor IX, human Factor X, or human Prothrombin have been inserted into the native activation peptide.

17. The modified polypeptide of claim 1, wherein at least 12 contiguous amino acids from the activation peptide of human Factor IX, human Factor X, or human Prothrombin have been inserted into the native activation peptide.

18. The modified polypeptide of claim 1, wherein at least 15 contiguous amino acids from the activation peptide of human Factor IX, human Factor X, or human Prothrombin have been inserted into the native activation peptide.

19. A pharmaceutical composition comprising the modified polypeptide of claim 1.

* * * * *

UNITED STATES PATENT AND TRADEMARK OFFICE
CERTIFICATE OF CORRECTION

PATENT NO. : 8,828,939 B2
APPLICATION NO. : 11/632552
DATED : September 9, 2014
INVENTOR(S) : Thomas Weimer et al.

It is certified that error appears in the above-identified patent and that said Letters Patent is hereby corrected as shown below:

In the Claims

In claim 1, column 131, line 45, "Factor Vila" should read --Factor VIIa--.

In claim 1, column 131, line 48, "Factor Vila" should read --Factor VIIa--.

In claim 1, column 131, line 50, "Factor Vila" should read --Factor VIIa--.

In claim 1, column 131, lines 54-55, "Factor Vila" should read --Factor VIIa--.

In claim 1, column 131, line 58, "Factor Vila" should read --Factor VIIa--.

In claim 1, column 131, lines 65-66, "Factor Vila" should read --Factor VIIa--.

In claim 1, column 132, line 45, "Factor Vila" should read --Factor VIIa--.

In claim 4, column 132, line 53, "in vitro" should read --*in vitro*--.

In claim 5, column 132, lines 57-58, "in vitro" should read --*in vitro*--.

Signed and Sealed this
Thirtieth Day of December, 2014

Michelle K. Lee
*Deputy Director of the United States Patent and Trademark Office*

SEQUENCE LISTING

```
<160> NUMBER OF SEQ ID NOS: 69

<210> SEQ ID NO 1
<211> LENGTH: 1401
<212> TYPE: DNA
<213> ORGANISM: Homo sapiens
<220> FEATURE:
<221> NAME/KEY: CDS
<222> LOCATION: (1)..(1398)
<220> FEATURE:
<221> NAME/KEY: sig_peptide
<222> LOCATION: (1)..(180)
<220> FEATURE:
<221> NAME/KEY: mat_peptide
<222> LOCATION: (181)..(1398)

<400> SEQUENCE: 1 atg gtc tcc cag gcc ctc agg ctc ctc tgc ctt ctg ctt ggg ctt cag      48
Met Val Ser Gln Ala Leu Arg Leu Leu Cys Leu Leu Leu Gly Leu Gln
-60             -55                 -50                 -45 ggc tgc ctg gct gca ggc ggg gtc gct aag gcc tca gga gga gaa aca      96
Gly Cys Leu Ala Ala Gly Gly Val Ala Lys Ala Ser Gly Gly Glu Thr
        -40                 -35                 -30 cgg gac atg ccg tgg aag ccg ggg cct cac aga gtc ttc gta acc cag     144
Arg Asp Met Pro Trp Lys Pro Gly Pro His Arg Val Phe Val Thr Gln
            -25                 -20                 -15 gag gaa gcc cac ggc gtc ctg cac cgg cgc cgg cgc gcc aac gcg ttc     192
Glu Glu Ala His Gly Val Leu His Arg Arg Arg Arg Ala Asn Ala Phe
        -10                  -5                  -1  1 ctg gag gag ctg cgg ccg ggc tcc ctg gag agg gag tgc aag gag gag     240
Leu Glu Glu Leu Arg Pro Gly Ser Leu Glu Arg Glu Cys Lys Glu Glu
5                   10                  15                  20 cag tgc tcc ttc gag gag gcc cgg gag atc ttc aag gac gcg gag agg     288
Gln Cys Ser Phe Glu Glu Ala Arg Glu Ile Phe Lys Asp Ala Glu Arg
                25                  30                  35 acg aag ctg ttc tgg att tct tac agt gat ggg gac cag tgt gcc tca     336
Thr Lys Leu Phe Trp Ile Ser Tyr Ser Asp Gly Asp Gln Cys Ala Ser
            40                  45                  50 agt cca tgc cag aat ggg ggc tcc tgc aag gac cag ctc cag tcc tat     384
Ser Pro Cys Gln Asn Gly Gly Ser Cys Lys Asp Gln Leu Gln Ser Tyr
        55                  60                  65 atc tgc ttc tgc ctc cct gcc ttc gag ggc cgg aac tgt gag acg cac     432
Ile Cys Phe Cys Leu Pro Ala Phe Glu Gly Arg Asn Cys Glu Thr His
    70                  75                  80 aag gat gac cag ctg atc tgt gtg aac gag aac ggc ggc tgt gag cag     480
Lys Asp Asp Gln Leu Ile Cys Val Asn Glu Asn Gly Gly Cys Glu Gln
85                  90                  95                  100
```

```
tac tgc agt gac cac acg ggc acc aag cgc tcc tgt cgg tgc cac gag      528
Tyr Cys Ser Asp His Thr Gly Thr Lys Arg Ser Cys Arg Cys His Glu
                105                 110                 115 ggg tac tct ctg ctg gca gac ggg gtg tcc tgc aca ccc aca gtt gaa      576
Gly Tyr Ser Leu Leu Ala Asp Gly Val Ser Cys Thr Pro Thr Val Glu
                120                 125                 130 tat cca tgt gga aaa ata cct att cta gaa aaa aga aat gcc agc aaa      624
Tyr Pro Cys Gly Lys Ile Pro Ile Leu Glu Lys Arg Asn Ala Ser Lys
                135                 140                 145 ccc caa ggc cga att gtg ggg ggc aag gtg tgc ccc aaa ggg gag tgt      672
Pro Gln Gly Arg Ile Val Gly Gly Lys Val Cys Pro Lys Gly Glu Cys
        150                 155                 160 cca tgg cag gtc ctg ttg ttg gtg aat gga gct cag ttg tgt ggg ggg      720
Pro Trp Gln Val Leu Leu Leu Val Asn Gly Ala Gln Leu Cys Gly Gly
165                 170                 175                 180 acc ctg atc aac acc atc tgg gtg gtc tcc gcg gcc cac tgt ttc gac      768
Thr Leu Ile Asn Thr Ile Trp Val Val Ser Ala Ala His Cys Phe Asp
                185                 190                 195 aaa atc aag aac tgg agg aac ctg atc gcg gtg ctg ggc gag cac gac      816
Lys Ile Lys Asn Trp Arg Asn Leu Ile Ala Val Leu Gly Glu His Asp
                200                 205                 210 ctc agc gag cac gac ggg gat gag cag agc cgg cgg gtg gcg cag gtc      864
Leu Ser Glu His Asp Gly Asp Glu Gln Ser Arg Arg Val Ala Gln Val
        215                 220                 225 atc atc ccc agc acg tac gtc ccg ggc acc acc aac cac gac atc gcg      912
Ile Ile Pro Ser Thr Tyr Val Pro Gly Thr Thr Asn His Asp Ile Ala
        230                 235                 240 ctg ctc cgc ctg cac cag ccc gtg gtc ctc act gac cat gtg gtg ccc      960
Leu Leu Arg Leu His Gln Pro Val Val Leu Thr Asp His Val Val Pro
245                 250                 255                 260 ctc tgc ctg ccc gaa cgg acg ttc tct gag agg acg ctg gcc ttc gtg     1008
Leu Cys Leu Pro Glu Arg Thr Phe Ser Glu Arg Thr Leu Ala Phe Val
                265                 270                 275 cgc ttc tca ttg gtc agc ggc tgg ggc cag ctg ctg gac cgt ggc gcc     1056
Arg Phe Ser Leu Val Ser Gly Trp Gly Gln Leu Leu Asp Arg Gly Ala
                280                 285                 290 acg gcc ctg gag ctc atg gtg ctc aac gtg ccc cgg ctg atg acc cag     1104
Thr Ala Leu Glu Leu Met Val Leu Asn Val Pro Arg Leu Met Thr Gln
        295                 300                 305 gac tgc ctg cag cag tca cgg aag gtg gga gac tcc cca aat atc acg     1152
Asp Cys Leu Gln Gln Ser Arg Lys Val Gly Asp Ser Pro Asn Ile Thr
        310                 315                 320 gag tac atg ttc tgt gcc ggc tac tcg gat ggc agc aag gac tcc tgc     1200
Glu Tyr Met Phe Cys Ala Gly Tyr Ser Asp Gly Ser Lys Asp Ser Cys
325                 330                 335                 340 aag ggg gac agt gga ggc cca cat gcc acc cac tac cgg ggc acg tgg     1248
Lys Gly Asp Ser Gly Gly Pro His Ala Thr His Tyr Arg Gly Thr Trp
                345                 350                 355 tac ctg acg ggc atc gtc agc tgg ggc cag ggc tgc gca acc gtg ggc     1296
Tyr Leu Thr Gly Ile Val Ser Trp Gly Gln Gly Cys Ala Thr Val Gly
                360                 365                 370 cac ttt ggg gtg tac acc agg gtc tcc cag tac atc gag tgg ctg caa     1344
His Phe Gly Val Tyr Thr Arg Val Ser Gln Tyr Ile Glu Trp Leu Gln
                375                 380                 385 aag ctc atg cgc tca gag cca cgc cca gga gtc ctc ctg cga gcc cca     1392
Lys Leu Met Arg Ser Glu Pro Arg Pro Gly Val Leu Leu Arg Ala Pro
        390                 395                 400 ttt ccc tag                                                          1401
Phe Pro
```

-continued

```
<210> SEQ ID NO 2
<211> LENGTH: 466
<212> TYPE: PRT
<213> ORGANISM: Homo sapiens

<400> SEQUENCE: 2

Met Val Ser Gln Ala Leu Arg Leu Leu Cys Leu Leu Leu Gly Leu Gln
-60             -55                 -50                 -45

Gly Cys Leu Ala Ala Gly Gly Val Ala Lys Ala Ser Gly Gly Glu Thr
            -40                 -35                 -30

Arg Asp Met Pro Trp Lys Pro Gly Pro His Arg Val Phe Val Thr Gln
            -25                 -20                 -15

Glu Glu Ala His Gly Val Leu His Arg Arg Arg Arg Ala Asn Ala Phe
        -10                  -5                  -1   1

Leu Glu Glu Leu Arg Pro Gly Ser Leu Glu Arg Glu Cys Lys Glu Glu
5               10                  15                  20

Gln Cys Ser Phe Glu Glu Ala Arg Glu Ile Phe Lys Asp Ala Glu Arg
            25                  30                  35

Thr Lys Leu Phe Trp Ile Ser Tyr Ser Asp Gly Asp Gln Cys Ala Ser
            40                  45                  50

Ser Pro Cys Gln Asn Gly Gly Ser Cys Lys Asp Gln Leu Gln Ser Tyr
            55                  60                  65

Ile Cys Phe Cys Leu Pro Ala Phe Glu Gly Arg Asn Cys Glu Thr His
70                  75                  80

Lys Asp Asp Gln Leu Ile Cys Val Asn Glu Asn Gly Gly Cys Glu Gln
85                  90                  95                  100

Tyr Cys Ser Asp His Thr Gly Thr Lys Arg Ser Cys Arg Cys His Glu
            105                 110                 115

Gly Tyr Ser Leu Leu Ala Asp Gly Val Ser Cys Thr Pro Thr Val Glu
            120                 125                 130

Tyr Pro Cys Gly Lys Ile Pro Ile Leu Glu Lys Arg Asn Ala Ser Lys
            135                 140                 145

Pro Gln Gly Arg Ile Val Gly Gly Lys Val Cys Pro Lys Gly Glu Cys
            150                 155                 160

Pro Trp Gln Val Leu Leu Leu Val Asn Gly Ala Gln Leu Cys Gly Gly
165                 170                 175                 180

Thr Leu Ile Asn Thr Ile Trp Val Val Ser Ala Ala His Cys Phe Asp
            185                 190                 195

Lys Ile Lys Asn Trp Arg Asn Leu Ile Ala Val Leu Gly Glu His Asp
            200                 205                 210

Leu Ser Glu His Asp Gly Asp Glu Gln Ser Arg Arg Val Ala Gln Val
            215                 220                 225

Ile Ile Pro Ser Thr Tyr Val Pro Gly Thr Thr Asn His Asp Ile Ala
            230                 235                 240

Leu Leu Arg Leu His Gln Pro Val Val Leu Thr Asp His Val Val Pro
245                 250                 255                 260

Leu Cys Leu Pro Glu Arg Thr Phe Ser Glu Arg Thr Leu Ala Phe Val
            265                 270                 275

Arg Phe Ser Leu Val Ser Gly Trp Gly Gln Leu Leu Asp Arg Gly Ala
            280                 285                 290

Thr Ala Leu Glu Leu Met Val Leu Asn Val Pro Arg Leu Met Thr Gln
            295                 300                 305
```

-continued

```
Asp Cys Leu Gln Gln Ser Arg Lys Val Gly Asp Ser Pro Asn Ile Thr
    310                 315                 320
Glu Tyr Met Phe Cys Ala Gly Tyr Ser Asp Gly Ser Lys Asp Ser Cys
325                 330                 335                 340
Lys Gly Asp Ser Gly Gly Pro His Ala Thr His Tyr Arg Gly Thr Trp
                345                 350                 355
Tyr Leu Thr Gly Ile Val Ser Trp Gly Gln Gly Cys Ala Thr Val Gly
                360                 365                 370
His Phe Gly Val Tyr Thr Arg Val Ser Gln Tyr Ile Glu Trp Leu Gln
                375                 380                 385
Lys Leu Met Arg Ser Glu Pro Arg Pro Gly Val Leu Leu Arg Ala Pro
390                 395                 400
Phe Pro
405

<210> SEQ ID NO 3
<211> LENGTH: 406
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Glu or gamma-carboxyglutamic acid
<220> FEATURE:
<221> NAME/KEY: MOD_RES
<222> LOCATION: (14)..(14)
<223> OTHER INFORMATION: Glu or gamma-carboxyglutamic acid
<220> FEATURE:
<221> NAME/KEY: MOD_RES
<222> LOCATION: (16)..(16)
<223> OTHER INFORMATION: Glu or gamma-carboxyglutamic acid
<220> FEATURE:
<221> NAME/KEY: MOD_RES
<222> LOCATION: (19)..(20)
<223> OTHER INFORMATION: Glu or gamma-carboxyglutamic acid
<220> FEATURE:
<221> NAME/KEY: MOD_RES
<222> LOCATION: (25)..(26)
<223> OTHER INFORMATION: Glu or gamma-carboxyglutamic acid
<220> FEATURE:
<221> NAME/KEY: MOD_RES
<222> LOCATION: (29)..(29)
<223> OTHER INFORMATION: Glu or gamma-carboxyglutamic acid
<220> FEATURE:
<221> NAME/KEY: MOD_RES
<222> LOCATION: (35)..(35)
<223> OTHER INFORMATION: Glu or gamma-carboxyglutamic acid

<400> SEQUENCE: 3

Ala Asn Ala Phe Leu Xaa Xaa Leu Arg Pro Gly Ser Leu Xaa Arg Xaa
1               5                   10                  15
Cys Lys Xaa Xaa Gln Cys Ser Phe Xaa Xaa Ala Arg Xaa Ile Phe Lys
                20                  25                  30
Asp Ala Xaa Arg Thr Lys Leu Phe Trp Ile Ser Tyr Ser Asp Gly Asp
            35                  40                  45
Gln Cys Ala Ser Ser Pro Cys Gln Asn Gly Gly Ser Cys Lys Asp Gln
        50                  55                  60
Leu Gln Ser Tyr Ile Cys Phe Cys Leu Pro Ala Phe Glu Gly Arg Asn
65                  70                  75                  80
Cys Glu Thr His Lys Asp Asp Gln Leu Ile Cys Val Asn Glu Asn Gly
                85                  90                  95
Gly Cys Glu Gln Tyr Cys Ser Asp His Thr Gly Thr Lys Arg Ser Cys
            100                 105                 110
Arg Cys His Glu Gly Tyr Ser Leu Leu Ala Asp Gly Val Ser Cys Thr
```

```
                    115                 120                 125
Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 4
<211> LENGTH: 1386
<212> TYPE: DNA
<213> ORGANISM: Homo sapiens
<220> FEATURE:
<221> NAME/KEY: CDS
<222> LOCATION: (1)..(1383)
<220> FEATURE:
<221> NAME/KEY: sig_peptide
<222> LOCATION: (1)..(126)
<220> FEATURE:
<221> NAME/KEY: mat_peptide
<222> LOCATION: (127)..(1383)

<400> SEQUENCE: 4 atg tgg cag ctc aca agc ctc ctg ctg ttc gtg gcc acc tgg gga att     48
Met Trp Gln Leu Thr Ser Leu Leu Leu Phe Val Ala Thr Trp Gly Ile
        -40                 -35                 -30 tcc ggc aca cca gct cct ctt gac tca gtg ttc tcc agc agc gag cgt     96
Ser Gly Thr Pro Ala Pro Leu Asp Ser Val Phe Ser Ser Ser Glu Arg
```

```
                -25                 -20                 -15
gcc cac cag gtg ctg cgg atc cgc aaa cgt gcc aac tcc ttc ctg gag    144
Ala His Gln Val Leu Arg Ile Arg Lys Arg Ala Asn Ser Phe Leu Glu
-10                 -5                  -1  1                 5 gag ctc cgt cac agc agc ctg gag cgg gag tgc ata gag gag atc tgt    192
Glu Leu Arg His Ser Ser Leu Glu Arg Glu Cys Ile Glu Glu Ile Cys
                10                  15                  20 gac ttc gag gag gcc aag gaa att ttc caa aat gtg gat gac aca ctg    240
Asp Phe Glu Glu Ala Lys Glu Ile Phe Gln Asn Val Asp Asp Thr Leu
            25                  30                  35 gcc ttc tgg tcc aag cac gtc gac ggt gac cag tgc ttg gtc ttg ccc    288
Ala Phe Trp Ser Lys His Val Asp Gly Asp Gln Cys Leu Val Leu Pro
        40                  45                  50 ttg gag cac ccg tgc gcc agc ctg tgc tgc ggg cac ggc acg tgc atc    336
Leu Glu His Pro Cys Ala Ser Leu Cys Cys Gly His Gly Thr Cys Ile
55                  60                  65                  70 gac ggc atc ggc agc ttc agc tgc gac tgc cgc agc ggc tgg gag ggc    384
Asp Gly Ile Gly Ser Phe Ser Cys Asp Cys Arg Ser Gly Trp Glu Gly
                75                  80                  85 cgc ttc tgc cag cgc gag gtg agc ttc ctc aat tgc tcg ctg gac aac    432
Arg Phe Cys Gln Arg Glu Val Ser Phe Leu Asn Cys Ser Leu Asp Asn
            90                  95                  100 ggc ggc tgc acg cat tac tgc cta gag gag gtg ggc tgg cgg cgc tgt    480
Gly Gly Cys Thr His Tyr Cys Leu Glu Glu Val Gly Trp Arg Arg Cys
        105                 110                 115 agc tgt gcg cct ggc tac aag ctg ggg gac gac ctc ctg cag tgt cac    528
Ser Cys Ala Pro Gly Tyr Lys Leu Gly Asp Asp Leu Leu Gln Cys His
120                 125                 130 ccc gca gtg aag ttc cct tgt ggg agg ccc tgg aag cgg atg gag aag    576
Pro Ala Val Lys Phe Pro Cys Gly Arg Pro Trp Lys Arg Met Glu Lys
135                 140                 145                 150 aag cgc agt cac ctg aaa cga gac aca gaa gac caa gaa gac caa gta    624
Lys Arg Ser His Leu Lys Arg Asp Thr Glu Asp Gln Glu Asp Gln Val
                155                 160                 165 gat ccg cgg ctc att gat ggg aag atg acc agg cgg gga gac agc ccc    672
Asp Pro Arg Leu Ile Asp Gly Lys Met Thr Arg Arg Gly Asp Ser Pro
            170                 175                 180 tgg cag gtg gtc ctg ctg gac tca aag aag aag ctg gcc tgc ggg gca    720
Trp Gln Val Val Leu Leu Asp Ser Lys Lys Lys Leu Ala Cys Gly Ala
        185                 190                 195 gtg ctc atc cac ccc tcc tgg gtg ctg aca gcg gcc cac tgc atg gat    768
Val Leu Ile His Pro Ser Trp Val Leu Thr Ala Ala His Cys Met Asp
200                 205                 210 gag tcc aag aag ctc ctt gtc agg ctt gga gag tat gac ctg cgg cgc    816
Glu Ser Lys Lys Leu Leu Val Arg Leu Gly Glu Tyr Asp Leu Arg Arg
215                 220                 225                 230 tgg gag aag tgg gag ctg gac ctg gac atc aag gag gtc ttc gtc cac    864
Trp Glu Lys Trp Glu Leu Asp Leu Asp Ile Lys Glu Val Phe Val His
                235                 240                 245 ccc aac tac agc aag agc acc acc gac aat gac atc gca ctg ctg cac    912
Pro Asn Tyr Ser Lys Ser Thr Thr Asp Asn Asp Ile Ala Leu Leu His
            250                 255                 260 ctg gcc cag ccc gcc acc ctc tcg cag acc ata gtg ccc atc tgc ctc    960
Leu Ala Gln Pro Ala Thr Leu Ser Gln Thr Ile Val Pro Ile Cys Leu
        265                 270                 275 ccg gac agc ggc ctt gca gag cgc gag ctc aat cag gcc ggc cag gag   1008
Pro Asp Ser Gly Leu Ala Glu Arg Glu Leu Asn Gln Ala Gly Gln Glu
280                 285                 290 acc ctc gtg acg ggc tgg ggc tac cac agc agc cga gag aag gag gcc   1056
Thr Leu Val Thr Gly Trp Gly Tyr His Ser Ser Arg Glu Lys Glu Ala
```

```
                                                    -continued

Thr Leu Val Thr Gly Trp Gly Tyr His Ser Ser Arg Glu Lys Glu Ala
295                 300                 305                 310 aag aga aac cgc acc ttc gtc ctc aac ttc atc aag att ccc gtg gtc    1104
Lys Arg Asn Arg Thr Phe Val Leu Asn Phe Ile Lys Ile Pro Val Val
                315                 320                 325 ccg cac aat gag tgc agc gag gtc atg agc aac atg gtg tct gag aac    1152
Pro His Asn Glu Cys Ser Glu Val Met Ser Asn Met Val Ser Glu Asn
330                 335                 340 atg ctg tgt gcg ggc atc ctc ggg gac cgg cag gat gcc tgc gag ggc    1200
Met Leu Cys Ala Gly Ile Leu Gly Asp Arg Gln Asp Ala Cys Glu Gly
            345                 350                 355 gac agt ggg ggg ccc atg gtc gcc tcc ttc cac ggc acc tgg ttc ctg    1248
Asp Ser Gly Gly Pro Met Val Ala Ser Phe His Gly Thr Trp Phe Leu
        360                 365                 370 gtg ggc ctg gtg agc tgg ggt gag ggc tgt ggg ctc ctt cac aac tac    1296
Val Gly Leu Val Ser Trp Gly Glu Gly Cys Gly Leu Leu His Asn Tyr
375                 380                 385                 390 ggc gtt tac acc aaa gtc agc cgc tac ctc gac tgg atc cat ggg cac    1344
Gly Val Tyr Thr Lys Val Ser Arg Tyr Leu Asp Trp Ile His Gly His
                395                 400                 405 atc aga gac aag gaa gcc ccc cag aag agc tgg gca cct tag           1386
Ile Arg Asp Lys Glu Ala Pro Gln Lys Ser Trp Ala Pro
                410                 415

<210> SEQ ID NO 5
<211> LENGTH: 461
<212> TYPE: PRT
<213> ORGANISM: Homo sapiens

<400> SEQUENCE: 5

Met Trp Gln Leu Thr Ser Leu Leu Phe Val Ala Thr Trp Gly Ile
        -40                 -35                 -30

Ser Gly Thr Pro Ala Pro Leu Asp Ser Val Phe Ser Ser Ser Glu Arg
    -25                 -20                 -15

Ala His Gln Val Leu Arg Ile Arg Lys Arg Ala Asn Ser Phe Leu Glu
-10                  -5                  -1   1                   5

Glu Leu Arg His Ser Ser Leu Glu Arg Glu Cys Ile Glu Glu Ile Cys
                10                  15                  20

Asp Phe Glu Glu Ala Lys Glu Ile Phe Gln Asn Val Asp Asp Thr Leu
            25                  30                  35

Ala Phe Trp Ser Lys His Val Asp Gly Asp Gln Cys Leu Val Leu Pro
40                  45                  50

Leu Glu His Pro Cys Ala Ser Leu Cys Cys Gly His Gly Thr Cys Ile
55                  60                  65                  70

Asp Gly Ile Gly Ser Phe Ser Cys Asp Cys Arg Ser Gly Trp Glu Gly
                75                  80                  85

Arg Phe Cys Gln Arg Glu Val Ser Phe Leu Asn Cys Ser Leu Asp Asn
            90                  95                  100

Gly Gly Cys Thr His Tyr Cys Leu Glu Glu Val Gly Trp Arg Arg Cys
        105                 110                 115

Ser Cys Ala Pro Gly Tyr Lys Leu Gly Asp Asp Leu Leu Gln Cys His
    120                 125                 130

Pro Ala Val Lys Phe Pro Cys Gly Arg Pro Trp Lys Arg Met Glu Lys
135                 140                 145                 150

Lys Arg Ser His Leu Lys Arg Asp Thr Glu Asp Gln Glu Asp Gln Val
                155                 160                 165

Asp Pro Arg Leu Ile Asp Gly Lys Met Thr Arg Arg Gly Asp Ser Pro
```

```
              170                 175                 180
Trp Gln Val Val Leu Asp Ser Lys Lys Leu Ala Cys Gly Ala
            185                 190                 195
Val Leu Ile His Pro Ser Trp Val Leu Thr Ala Ala His Cys Met Asp
            200                 205                 210
Glu Ser Lys Lys Leu Leu Val Arg Leu Gly Glu Tyr Asp Leu Arg Arg
215                 220                 225                 230
Trp Glu Lys Trp Glu Leu Asp Leu Asp Ile Lys Glu Val Phe Val His
                    235                 240                 245
Pro Asn Tyr Ser Lys Ser Thr Thr Asp Asn Asp Ile Ala Leu Leu His
                250                 255                 260
Leu Ala Gln Pro Ala Thr Leu Ser Gln Thr Ile Val Pro Ile Cys Leu
            265                 270                 275
Pro Asp Ser Gly Leu Ala Glu Arg Glu Leu Asn Gln Ala Gly Gln Glu
            280                 285                 290
Thr Leu Val Thr Gly Trp Gly Tyr His Ser Ser Arg Glu Lys Glu Ala
295                 300                 305                 310
Lys Arg Asn Arg Thr Phe Val Leu Asn Phe Ile Lys Ile Pro Val Val
                    315                 320                 325
Pro His Asn Glu Cys Ser Glu Val Met Ser Asn Met Val Ser Glu Asn
                330                 335                 340
Met Leu Cys Ala Gly Ile Leu Gly Asp Arg Gln Asp Ala Cys Glu Gly
            345                 350                 355
Asp Ser Gly Gly Pro Met Val Ala Ser Phe His Gly Thr Trp Phe Leu
            360                 365                 370
Val Gly Leu Val Ser Trp Gly Glu Gly Cys Gly Leu Leu His Asn Tyr
375                 380                 385                 390
Gly Val Tyr Thr Lys Val Ser Arg Tyr Leu Asp Trp Ile His Gly His
                    395                 400                 405
Ile Arg Asp Lys Glu Ala Pro Gln Lys Ser Trp Ala Pro
                410                 415
```

<210> SEQ ID NO 6
<211> LENGTH: 419
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Glu or gamma-carboxyglutamic acid
<220> FEATURE:
<221> NAME/KEY: MOD_RES
<222> LOCATION: (14)..(14)
<223> OTHER INFORMATION: Glu or gamma-carboxyglutamic acid
<220> FEATURE:
<221> NAME/KEY: MOD_RES
<222> LOCATION: (16)..(16)
<223> OTHER INFORMATION: Glu or gamma-carboxyglutamic acid
<220> FEATURE:
<221> NAME/KEY: MOD_RES
<222> LOCATION: (19)..(20)
<223> OTHER INFORMATION: Glu or gamma-carboxyglutamic acid
<220> FEATURE:
<221> NAME/KEY: MOD_RES
<222> LOCATION: (25)..(26)
<223> OTHER INFORMATION: Glu or gamma-carboxyglutamic acid
<220> FEATURE:
<221> NAME/KEY: MOD_RES
<222> LOCATION: (29)..(29)
<223> OTHER INFORMATION: Glu or gamma-carboxyglutamic acid

<400> SEQUENCE: 6

-continued

```
Ala Asn Ser Phe Leu Xaa Xaa Leu Arg His Ser Ser Leu Xaa Arg Xaa
1               5                   10                  15

Cys Ile Xaa Xaa Ile Cys Asp Phe Xaa Xaa Ala Lys Xaa Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro
```

```
<210> SEQ ID NO 7
<211> LENGTH: 1386
<212> TYPE: DNA
<213> ORGANISM: Homo sapiens
<220> FEATURE:
<221> NAME/KEY: CDS
<222> LOCATION: (1)..(1383)
<220> FEATURE:
<221> NAME/KEY: sig_peptide
<222> LOCATION: (1)..(138)
<220> FEATURE:
<221> NAME/KEY: mat_peptide
<222> LOCATION: (139)..(1383)

<400> SEQUENCE: 7
```

| | | | | | | | | | | | | | | | |
|---|---|---|---|---|---|---|---|---|---|---|---|---|---|---|---|
| atg | cag | cgc | gtg | aac | atg | atc | atg | gca | gaa | tca | cca | ggc | ctc | atc | acc | 48 |
| Met | Gln | Arg | Val | Asn | Met | Ile | Met | Ala | Glu | Ser | Pro | Gly | Leu | Ile | Thr | |
| | -45 | | | | -40 | | | | | -35 | | | | | | |

| atc | tgc | ctt | tta | gga | tat | cta | ctc | agt | gct | gaa | tgt | aca | gtt | ttt | ctt | 96 |
|---|---|---|---|---|---|---|---|---|---|---|---|---|---|---|---|---|
| Ile | Cys | Leu | Leu | Gly | Tyr | Leu | Leu | Ser | Ala | Glu | Cys | Thr | Val | Phe | Leu | |
| -30 | | | | | -25 | | | | | -20 | | | | | -15 | |

| gat | cat | gaa | aac | gcc | aac | aaa | att | ctg | aat | cgg | cca | aag | agg | tat | aat | 144 |
|---|---|---|---|---|---|---|---|---|---|---|---|---|---|---|---|---|
| Asp | His | Glu | Asn | Ala | Asn | Lys | Ile | Leu | Asn | Arg | Pro | Lys | Arg | Tyr | Asn | |
| | | | -10 | | | | | -5 | | | | | -1 | 1 | | |

| tca | ggt | aaa | ttg | gaa | gag | ttt | gtt | caa | ggg | aac | ctt | gag | aga | gaa | tgt | 192 |
|---|---|---|---|---|---|---|---|---|---|---|---|---|---|---|---|---|
| Ser | Gly | Lys | Leu | Glu | Glu | Phe | Val | Gln | Gly | Asn | Leu | Glu | Arg | Glu | Cys | |
| | | 5 | | | | | 10 | | | | | 15 | | | | |

| atg | gaa | gaa | aag | tgt | agt | ttt | gaa | gaa | gca | cga | gaa | gtt | ttt | gaa | aac | 240 |
|---|---|---|---|---|---|---|---|---|---|---|---|---|---|---|---|---|
| Met | Glu | Glu | Lys | Cys | Ser | Phe | Glu | Glu | Ala | Arg | Glu | Val | Phe | Glu | Asn | |
| | 20 | | | | | 25 | | | | | 30 | | | | | |

| act | gaa | aga | aca | act | gaa | ttt | tgg | aag | cag | tat | gtt | gat | gga | gat | cag | 288 |
|---|---|---|---|---|---|---|---|---|---|---|---|---|---|---|---|---|
| Thr | Glu | Arg | Thr | Thr | Glu | Phe | Trp | Lys | Gln | Tyr | Val | Asp | Gly | Asp | Gln | |
| 35 | | | | | 40 | | | | | 45 | | | | | 50 | |

| tgt | gag | tcc | aat | cca | tgt | tta | aat | ggc | ggc | agt | tgc | aag | gat | gac | att | 336 |
|---|---|---|---|---|---|---|---|---|---|---|---|---|---|---|---|---|
| Cys | Glu | Ser | Asn | Pro | Cys | Leu | Asn | Gly | Gly | Ser | Cys | Lys | Asp | Asp | Ile | |
| | | | 55 | | | | | 60 | | | | | 65 | | | |

| aat | tcc | tat | gaa | tgt | tgg | tgt | ccc | ttt | gga | ttt | gaa | gga | aag | aac | tgt | 384 |
|---|---|---|---|---|---|---|---|---|---|---|---|---|---|---|---|---|
| Asn | Ser | Tyr | Glu | Cys | Trp | Cys | Pro | Phe | Gly | Phe | Glu | Gly | Lys | Asn | Cys | |
| | | 70 | | | | | 75 | | | | | 80 | | | | |

| gaa | tta | gat | gta | aca | tgt | aac | att | aag | aat | ggc | aga | tgc | gag | cag | ttt | 432 |
|---|---|---|---|---|---|---|---|---|---|---|---|---|---|---|---|---|
| Glu | Leu | Asp | Val | Thr | Cys | Asn | Ile | Lys | Asn | Gly | Arg | Cys | Glu | Gln | Phe | |
| | 85 | | | | | 90 | | | | | 95 | | | | | |

| tgt | aaa | aat | agt | gct | gat | aac | aag | gtg | gtt | tgc | tcc | tgt | act | gag | gga | 480 |
|---|---|---|---|---|---|---|---|---|---|---|---|---|---|---|---|---|
| Cys | Lys | Asn | Ser | Ala | Asp | Asn | Lys | Val | Val | Cys | Ser | Cys | Thr | Glu | Gly | |
| 100 | | | | | 105 | | | | | 110 | | | | | | |

| tat | cga | ctt | gca | gaa | aac | cag | aag | tcc | tgt | gaa | cca | gca | gtg | cca | ttt | 528 |
|---|---|---|---|---|---|---|---|---|---|---|---|---|---|---|---|---|
| Tyr | Arg | Leu | Ala | Glu | Asn | Gln | Lys | Ser | Cys | Glu | Pro | Ala | Val | Pro | Phe | |
| 115 | | | | | 120 | | | | | 125 | | | | | 130 | |

| cca | tgt | gga | aga | gtt | tct | gtt | tca | caa | act | tct | aag | ctc | acc | cgt | gct | 576 |
|---|---|---|---|---|---|---|---|---|---|---|---|---|---|---|---|---|
| Pro | Cys | Gly | Arg | Val | Ser | Val | Ser | Gln | Thr | Ser | Lys | Leu | Thr | Arg | Ala | |
| | | | 135 | | | | | 140 | | | | | 145 | | | |

| gag | act | gtt | ttt | cct | gat | gtg | gac | tat | gta | aat | tct | act | gaa | gct | gaa | 624 |
|---|---|---|---|---|---|---|---|---|---|---|---|---|---|---|---|---|
| Glu | Thr | Val | Phe | Pro | Asp | Val | Asp | Tyr | Val | Asn | Ser | Thr | Glu | Ala | Glu | |
| | | | 150 | | | | | 155 | | | | | 160 | | | |

| acc | att | ttg | gat | aac | atc | act | caa | agc | acc | caa | tca | ttt | aat | gac | ttc | 672 |
|---|---|---|---|---|---|---|---|---|---|---|---|---|---|---|---|---|
| Thr | Ile | Leu | Asp | Asn | Ile | Thr | Gln | Ser | Thr | Gln | Ser | Phe | Asn | Asp | Phe | |
| | 165 | | | | | 170 | | | | | 175 | | | | | |

| act | cgg | gtt | gtt | ggt | gga | gaa | gat | gcc | aaa | cca | ggt | caa | ttc | cct | tgg | 720 |
|---|---|---|---|---|---|---|---|---|---|---|---|---|---|---|---|---|
| Thr | Arg | Val | Val | Gly | Gly | Glu | Asp | Ala | Lys | Pro | Gly | Gln | Phe | Pro | Trp | |
| 180 | | | | | 185 | | | | | 190 | | | | | | |

| cag | gtt | gtt | ttg | aat | ggt | aaa | gtt | gat | gca | ttc | tgt | gga | ggc | tct | atc | 768 |
|---|---|---|---|---|---|---|---|---|---|---|---|---|---|---|---|---|
| Gln | Val | Val | Leu | Asn | Gly | Lys | Val | Asp | Ala | Phe | Cys | Gly | Gly | Ser | Ile | |

-continued

| | | | | | | | | | | | | | | |
|---|---|---|---|---|---|---|---|---|---|---|---|---|---|---|
| Gln | Val | Val | Leu | Asn | Gly | Lys | Val | Asp | Ala | Phe | Cys | Gly | Gly | Ser | Ile |
| 195 | | | | 200 | | | | 205 | | | | 210 | | |

```
gtt aat gaa aaa tgg att gta act gct gcc cac tgt gtt gaa act ggt      816
Val Asn Glu Lys Trp Ile Val Thr Ala Ala His Cys Val Glu Thr Gly
            215                 220                 225 gtt aaa att aca gtt gtc gca ggt gaa cat aat att gag gag aca gaa      864
Val Lys Ile Thr Val Val Ala Gly Glu His Asn Ile Glu Glu Thr Glu
        230                 235                 240 cat aca gag caa aag cga aat gtg att cga att att cct cac cac aac      912
His Thr Glu Gln Lys Arg Asn Val Ile Arg Ile Ile Pro His His Asn
        245                 250                 255 tac aat gca gct att aat aag tac aac cat gac att gcc ctt ctg gaa      960
Tyr Asn Ala Ala Ile Asn Lys Tyr Asn His Asp Ile Ala Leu Leu Glu
    260                 265                 270 ctg gac gaa ccc tta gtg cta aac agc tac gtt aca cct att tgc att     1008
Leu Asp Glu Pro Leu Val Leu Asn Ser Tyr Val Thr Pro Ile Cys Ile
275                 280                 285                 290 gct gac aag gaa tac acg aac atc ttc ctc aaa ttt gga tct ggc tat     1056
Ala Asp Lys Glu Tyr Thr Asn Ile Phe Leu Lys Phe Gly Ser Gly Tyr
                295                 300                 305 gta agt ggc tgg gga aga gtc ttc cac aaa ggg aga tca gct tta gtt     1104
Val Ser Gly Trp Gly Arg Val Phe His Lys Gly Arg Ser Ala Leu Val
            310                 315                 320 ctt cag tac ctt aga gtt cca ctt gtt gac cga gcc aca tgt ctt cga     1152
Leu Gln Tyr Leu Arg Val Pro Leu Val Asp Arg Ala Thr Cys Leu Arg
        325                 330                 335 tct aca aag ttc acc atc tat aac aac atg ttc tgt gct ggc ttc cat     1200
Ser Thr Lys Phe Thr Ile Tyr Asn Asn Met Phe Cys Ala Gly Phe His
        340                 345                 350 gaa gga ggt aga gat tca tgt caa gga gat agt ggg gga ccc cat gtt     1248
Glu Gly Gly Arg Asp Ser Cys Gln Gly Asp Ser Gly Gly Pro His Val
355                 360                 365                 370 act gaa gtg gaa ggg acc agt ttc tta act gga att att agc tgg ggt     1296
Thr Glu Val Glu Gly Thr Ser Phe Leu Thr Gly Ile Ile Ser Trp Gly
                375                 380                 385 gaa gag tgt gca atg aaa ggc aaa tat gga ata tat acc aag gta tcc     1344
Glu Glu Cys Ala Met Lys Gly Lys Tyr Gly Ile Tyr Thr Lys Val Ser
            390                 395                 400 cgg tat gtc aac tgg att aag gaa aaa aca aag ctc act taa             1386
Arg Tyr Val Asn Trp Ile Lys Glu Lys Thr Lys Leu Thr
        405                 410                 415

<210> SEQ ID NO 8
<211> LENGTH: 461
<212> TYPE: PRT
<213> ORGANISM: Homo sapiens

<400> SEQUENCE: 8

Met Gln Arg Val Asn Met Ile Met Ala Glu Ser Pro Gly Leu Ile Thr
        -45                 -40                 -35

Ile Cys Leu Leu Gly Tyr Leu Leu Ser Ala Glu Cys Thr Val Phe Leu
-30                 -25                 -20                 -15

Asp His Glu Asn Ala Asn Lys Ile Leu Asn Arg Pro Lys Arg Tyr Asn
                -10                 -5                  -1   1

Ser Gly Lys Leu Glu Glu Phe Val Gln Gly Asn Leu Glu Arg Glu Cys
            5                   10                  15

Met Glu Glu Lys Cys Ser Phe Glu Glu Ala Arg Glu Val Phe Glu Asn
        20                  25                  30

Thr Glu Arg Thr Thr Glu Phe Trp Lys Gln Tyr Val Asp Gly Asp Gln
```

```
            35                  40                  45                  50
        Cys Glu Ser Asn Pro Cys Leu Asn Gly Gly Ser Cys Lys Asp Asp Ile
                        55                  60                  65

Asn Ser Tyr Glu Cys Trp Cys Pro Phe Gly Phe Glu Gly Lys Asn Cys
                    70                  75                  80

Glu Leu Asp Val Thr Cys Asn Ile Lys Asn Gly Arg Cys Glu Gln Phe
                85                  90                  95

Cys Lys Asn Ser Ala Asp Asn Lys Val Val Cys Ser Cys Thr Glu Gly
        100                 105                 110

Tyr Arg Leu Ala Glu Asn Gln Lys Ser Cys Glu Pro Ala Val Pro Phe
        115                 120                 125                 130

Pro Cys Gly Arg Val Ser Val Ser Gln Thr Ser Lys Leu Thr Arg Ala
                        135                 140                 145

Glu Thr Val Phe Pro Asp Val Asp Tyr Val Asn Ser Thr Glu Ala Glu
                    150                 155                 160

Thr Ile Leu Asp Asn Ile Thr Gln Ser Thr Gln Ser Phe Asn Asp Phe
                165                 170                 175

Thr Arg Val Val Gly Gly Glu Asp Ala Lys Pro Gly Gln Phe Pro Trp
        180                 185                 190

Gln Val Val Leu Asn Gly Lys Val Asp Ala Phe Cys Gly Gly Ser Ile
        195                 200                 205                 210

Val Asn Glu Lys Trp Ile Val Thr Ala Ala His Cys Val Glu Thr Gly
                        215                 220                 225

Val Lys Ile Thr Val Val Ala Gly Glu His Asn Ile Glu Glu Thr Glu
                    230                 235                 240

His Thr Glu Gln Lys Arg Asn Val Ile Arg Ile Ile Pro His His Asn
                245                 250                 255

Tyr Asn Ala Ala Ile Asn Lys Tyr Asn His Asp Ile Ala Leu Leu Glu
        260                 265                 270

Leu Asp Glu Pro Leu Val Leu Asn Ser Tyr Val Thr Pro Ile Cys Ile
        275                 280                 285                 290

Ala Asp Lys Glu Tyr Thr Asn Ile Phe Leu Lys Phe Gly Ser Gly Tyr
                        295                 300                 305

Val Ser Gly Trp Gly Arg Val Phe His Lys Gly Arg Ser Ala Leu Val
                    310                 315                 320

Leu Gln Tyr Leu Arg Val Pro Leu Val Asp Arg Ala Thr Cys Leu Arg
                325                 330                 335

Ser Thr Lys Phe Thr Ile Tyr Asn Asn Met Phe Cys Ala Gly Phe His
        340                 345                 350

Glu Gly Gly Arg Asp Ser Cys Gln Gly Asp Ser Gly Gly Pro His Val
        355                 360                 365                 370

Thr Glu Val Glu Gly Thr Ser Phe Leu Thr Gly Ile Ile Ser Trp Gly
                        375                 380                 385

Glu Glu Cys Ala Met Lys Gly Lys Tyr Gly Ile Tyr Thr Lys Val Ser
                    390                 395                 400

Arg Tyr Val Asn Trp Ile Lys Glu Lys Thr Lys Leu Thr
                405                 410                 415

<210> SEQ ID NO 9
<211> LENGTH: 415
<212> TYPE: PRT
<213> ORGANISM: Homo sapiens
<220> FEATURE:
<221> NAME/KEY: MOD_RES
<222> LOCATION: (7)..(8)
```

-continued

<223> OTHER INFORMATION: Glu or gamma-carboxyglutamic acid
<220> FEATURE:
<221> NAME/KEY: MOD_RES
<222> LOCATION: (15)..(15)
<223> OTHER INFORMATION: Glu or gamma-carboxyglutamic acid
<220> FEATURE:
<221> NAME/KEY: MOD_RES
<222> LOCATION: (17)..(17)
<223> OTHER INFORMATION: Glu or gamma-carboxyglutamic acid
<220> FEATURE:
<221> NAME/KEY: MOD_RES
<222> LOCATION: (20)..(21)
<223> OTHER INFORMATION: Glu or gamma-carboxyglutamic acid
<220> FEATURE:
<221> NAME/KEY: MOD_RES
<222> LOCATION: (26)..(27)
<223> OTHER INFORMATION: Glu or gamma-carboxyglutamic acid
<220> FEATURE:
<221> NAME/KEY: MOD_RES
<222> LOCATION: (30)..(30)
<223> OTHER INFORMATION: Glu or gamma-carboxyglutamic acid
<220> FEATURE:
<221> NAME/KEY: MOD_RES
<222> LOCATION: (33)..(33)
<223> OTHER INFORMATION: Glu or gamma-carboxyglutamic acid
<220> FEATURE:
<221> NAME/KEY: MOD_RES
<222> LOCATION: (36)..(36)
<223> OTHER INFORMATION: Glu or gamma-carboxyglutamic acid
<220> FEATURE:
<221> NAME/KEY: MOD_RES
<222> LOCATION: (40)..(40)
<223> OTHER INFORMATION: Glu or gamma-carboxyglutamic acid

<400> SEQUENCE: 9

Tyr Asn Ser Gly Lys Leu Xaa Xaa Phe Val Gln Gly Asn Leu Xaa Arg
1               5                   10                  15

Xaa Cys Met Xaa Xaa Lys Cys Ser Phe Xaa Xaa Ala Arg Xaa Val Phe
            20                  25                  30

Xaa Asn Thr Xaa Arg Thr Thr Xaa Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu

```
               225                 230                 235                 240
         Thr Glu His Thr Glu Gln Lys Arg Asn Val Ile Arg Ile Ile Pro His
                         245                 250                 255

His Asn Tyr Asn Ala Ala Ile Asn Lys Tyr Asn His Asp Ile Ala Leu
                         260                 265                 270

Leu Glu Leu Asp Glu Pro Leu Val Leu Asn Ser Tyr Val Thr Pro Ile
                         275                 280                 285

Cys Ile Ala Asp Lys Glu Tyr Thr Asn Ile Phe Leu Lys Phe Gly Ser
                         290                 295                 300

Gly Tyr Val Ser Gly Trp Gly Arg Val Phe His Lys Gly Arg Ser Ala
         305                 310                 315                 320

Leu Val Leu Gln Tyr Leu Arg Val Pro Leu Val Asp Arg Ala Thr Cys
                         325                 330                 335

Leu Arg Ser Thr Lys Phe Thr Ile Tyr Asn Asn Met Phe Cys Ala Gly
                         340                 345                 350

Phe His Glu Gly Gly Arg Asp Ser Cys Gln Gly Asp Ser Gly Gly Pro
                         355                 360                 365

His Val Thr Glu Val Glu Gly Thr Ser Phe Leu Thr Gly Ile Ile Ser
                         370                 375                 380

Trp Gly Glu Glu Cys Ala Met Lys Gly Lys Tyr Gly Ile Tyr Thr Lys
         385                 390                 395                 400

Val Ser Arg Tyr Val Asn Trp Ile Lys Glu Lys Thr Lys Leu Thr
                         405                 410                 415

<210> SEQ ID NO 10
<211> LENGTH: 1467
<212> TYPE: DNA
<213> ORGANISM: Homo sapiens
<220> FEATURE:
<221> NAME/KEY: CDS
<222> LOCATION: (1)..(1464)
<220> FEATURE:
<221> NAME/KEY: sig_peptide
<222> LOCATION: (1)..(120)
<220> FEATURE:
<221> NAME/KEY: mat_peptide
<222> LOCATION: (121)..(1464)

<400> SEQUENCE: 10 atg ggg cgc cca ctg cac ctc gtc ctg ctc agt gcc tcc ctg gct ggc     48
Met Gly Arg Pro Leu His Leu Val Leu Leu Ser Ala Ser Leu Ala Gly
-40                 -35                 -30                 -25 ctc ctg ctg ctc ggg gaa agt ctg ttc atc cgc agg gag cag gcc aac     96
Leu Leu Leu Leu Gly Glu Ser Leu Phe Ile Arg Arg Glu Gln Ala Asn
                -20                 -15                 -10 aac atc ctg gcg agg gtc acg agg gcc aat tcc ttt ctt gaa gag atg    144
Asn Ile Leu Ala Arg Val Thr Arg Ala Asn Ser Phe Leu Glu Glu Met
            -5                  -1  1                   5 aag aaa gga cac ctc gaa aga gag tgc atg gaa gag acc tgc tca tac    192
Lys Lys Gly His Leu Glu Arg Glu Cys Met Glu Glu Thr Cys Ser Tyr
        10                  15                  20 gaa gag gcc cgc gag gtc ttt gag gac agc gac aag acg aat gaa ttc    240
Glu Glu Ala Arg Glu Val Phe Glu Asp Ser Asp Lys Thr Asn Glu Phe
25                  30                  35                  40 tgg aat aaa tac aaa gat ggc gac cag tgt gag acc agt cct tgc cag    288
Trp Asn Lys Tyr Lys Asp Gly Asp Gln Cys Glu Thr Ser Pro Cys Gln
                45                  50                  55 aac cag ggc aaa tgt aaa gac ggc ctc ggg gaa tac acc tgc acc tgt    336
Asn Gln Gly Lys Cys Lys Asp Gly Leu Gly Glu Tyr Thr Cys Thr Cys
            60                  65                  70
```

```
tta gaa gga ttc gaa ggc aaa aac tgt gaa tta ttc aca cgg aag ctc      384
Leu Glu Gly Phe Glu Gly Lys Asn Cys Glu Leu Phe Thr Arg Lys Leu
            75                  80                  85 tgc agc ctg gac aac ggg gac tgt gac cag ttc tgc cac gag gaa cag      432
Cys Ser Leu Asp Asn Gly Asp Cys Asp Gln Phe Cys His Glu Glu Gln
    90                  95                  100 aac tct gtg gtg tgc tcc tgc gcc cgc ggg tac acc ctg gct gac aac      480
Asn Ser Val Val Cys Ser Cys Ala Arg Gly Tyr Thr Leu Ala Asp Asn
105                 110                 115                 120 ggc aag gcc tgc att ccc aca ggg ccc tac ccc tgt ggg aaa cag acc      528
Gly Lys Ala Cys Ile Pro Thr Gly Pro Tyr Pro Cys Gly Lys Gln Thr
                125                 130                 135 ctg gaa cgc agg aag agg tca gtg gcc cag gcc acc agc agc agc ggg      576
Leu Glu Arg Arg Lys Arg Ser Val Ala Gln Ala Thr Ser Ser Ser Gly
            140                 145                 150 gag gcc cct gac agc atc aca tgg aag cca tat gat gca gcc gac ctg      624
Glu Ala Pro Asp Ser Ile Thr Trp Lys Pro Tyr Asp Ala Ala Asp Leu
    155                 160                 165 gac ccc acc gag aac ccc ttc gac ctg ctt gac ttc aac cag acg cag      672
Asp Pro Thr Glu Asn Pro Phe Asp Leu Leu Asp Phe Asn Gln Thr Gln
170                 175                 180 cct gag agg ggc gac aac aac ctc acc agg atc gtg gga ggc cag gaa      720
Pro Glu Arg Gly Asp Asn Asn Leu Thr Arg Ile Val Gly Gly Gln Glu
185                 190                 195                 200 tgc aag gac ggg gag tgt ccc tgg cag gcc ctg ctc atc aat gag gaa      768
Cys Lys Asp Gly Glu Cys Pro Trp Gln Ala Leu Leu Ile Asn Glu Glu
                205                 210                 215 aac gag ggt ttc tgt ggt gga acc att ctg agc gag ttc tac atc cta      816
Asn Glu Gly Phe Cys Gly Gly Thr Ile Leu Ser Glu Phe Tyr Ile Leu
            220                 225                 230 acg gca gcc cac tgt ctc tac caa gcc aag aga ttc aag gtg agg gta      864
Thr Ala Ala His Cys Leu Tyr Gln Ala Lys Arg Phe Lys Val Arg Val
    235                 240                 245 ggg gac cgg aac acg gag cag gag gag ggc ggt gag gcg gtg cac gag      912
Gly Asp Arg Asn Thr Glu Gln Glu Glu Gly Gly Glu Ala Val His Glu
250                 255                 260 gtg gag gtg gtc atc aag cac aac cgg ttc aca aag gag acc tat gac      960
Val Glu Val Val Ile Lys His Asn Arg Phe Thr Lys Glu Thr Tyr Asp
265                 270                 275                 280 ttc gac atc gcc gtg ctc cgg ctc aag acc ccc atc acc ttc cgc atg     1008
Phe Asp Ile Ala Val Leu Arg Leu Lys Thr Pro Ile Thr Phe Arg Met
                285                 290                 295 aac gtg gcg cct gcc tgc ctc ccc gag cgt gac tgg gcc gag tcc acg     1056
Asn Val Ala Pro Ala Cys Leu Pro Glu Arg Asp Trp Ala Glu Ser Thr
            300                 305                 310 ctg atg acg cag aag acg ggg att gtg agc ggc ttc ggg cgc acc cac     1104
Leu Met Thr Gln Lys Thr Gly Ile Val Ser Gly Phe Gly Arg Thr His
    315                 320                 325 gag aag ggc cgg cag tcc acc agg ctc aag atg ctg gag gtg ccc tac     1152
Glu Lys Gly Arg Gln Ser Thr Arg Leu Lys Met Leu Glu Val Pro Tyr
330                 335                 340 gtg gac cgc aac agc tgc aag ctg tcc agc agc ttc atc atc acc cag     1200
Val Asp Arg Asn Ser Cys Lys Leu Ser Ser Ser Phe Ile Ile Thr Gln
345                 350                 355                 360 aac atg ttc tgt gcc ggc tac gac acc aag cag gag gat gcc tgc cag     1248
Asn Met Phe Cys Ala Gly Tyr Asp Thr Lys Gln Glu Asp Ala Cys Gln
                365                 370                 375 ggg gac agc ggg ggc ccg cac gtc acc cgc ttc aag gac acc tac ttc     1296
Gly Asp Ser Gly Gly Pro His Val Thr Arg Phe Lys Asp Thr Tyr Phe
```

```
              380                 385                 390
gtg aca ggc atc gtc agc tgg gga gag ggc tgt gcc cgt aag ggg aag    1344
Val Thr Gly Ile Val Ser Trp Gly Glu Gly Cys Ala Arg Lys Gly Lys
            395                 400                 405 tac ggg atc tac acc aag gtc acc gcc ttc ctc aag tgg atc gac agg    1392
Tyr Gly Ile Tyr Thr Lys Val Thr Ala Phe Leu Lys Trp Ile Asp Arg
        410                 415                 420 tcc atg aaa acc agg ggc ttg ccc aag gcc aag agc cat gcc ccg gag    1440
Ser Met Lys Thr Arg Gly Leu Pro Lys Ala Lys Ser His Ala Pro Glu
425                 430                 435                 440 gtc ata acg tcc tct cca tta aag tga                                1467
Val Ile Thr Ser Ser Pro Leu Lys
                445

<210> SEQ ID NO 11
<211> LENGTH: 488
<212> TYPE: PRT
<213> ORGANISM: Homo sapiens

<400> SEQUENCE: 11

Met Gly Arg Pro Leu His Leu Val Leu Leu Ser Ala Ser Leu Ala Gly
-40                 -35                 -30                 -25

Leu Leu Leu Leu Gly Glu Ser Leu Phe Ile Arg Arg Glu Gln Ala Asn
                -20                 -15                 -10

Asn Ile Leu Ala Arg Val Thr Arg Ala Asn Ser Phe Leu Glu Glu Met
            -5                  -1  1               5

Lys Lys Gly His Leu Glu Arg Glu Cys Met Glu Glu Thr Cys Ser Tyr
        10                  15                  20

Glu Glu Ala Arg Glu Val Phe Glu Asp Ser Asp Lys Thr Asn Glu Phe
25                  30                  35                  40

Trp Asn Lys Tyr Lys Asp Gly Asp Gln Cys Glu Thr Ser Pro Cys Gln
                45                  50                  55

Asn Gln Gly Lys Cys Lys Asp Gly Leu Gly Glu Tyr Thr Cys Thr Cys
            60                  65                  70

Leu Glu Gly Phe Glu Gly Lys Asn Cys Glu Leu Phe Thr Arg Lys Leu
        75                  80                  85

Cys Ser Leu Asp Asn Gly Asp Cys Asp Gln Phe Cys His Glu Glu Gln
90                  95                  100

Asn Ser Val Val Cys Ser Cys Ala Arg Gly Tyr Thr Leu Ala Asp Asn
105                 110                 115                 120

Gly Lys Ala Cys Ile Pro Thr Gly Pro Tyr Pro Cys Gly Lys Gln Thr
                125                 130                 135

Leu Glu Arg Arg Lys Arg Ser Val Ala Gln Ala Thr Ser Ser Ser Gly
            140                 145                 150

Glu Ala Pro Asp Ser Ile Thr Trp Lys Pro Tyr Asp Ala Ala Asp Leu
        155                 160                 165

Asp Pro Thr Glu Asn Pro Phe Asp Leu Leu Asp Phe Asn Gln Thr Gln
170                 175                 180

Pro Glu Arg Gly Asp Asn Asn Leu Thr Arg Ile Val Gly Gly Gln Glu
185                 190                 195                 200

Cys Lys Asp Gly Glu Cys Pro Trp Gln Ala Leu Leu Ile Asn Glu Glu
                205                 210                 215

Asn Glu Gly Phe Cys Gly Gly Thr Ile Leu Ser Glu Phe Tyr Ile Leu
            220                 225                 230

Thr Ala Ala His Cys Leu Tyr Gln Ala Lys Arg Phe Lys Val Arg Val
        235                 240                 245
```

-continued

```
Gly Asp Arg Asn Thr Glu Gln Glu Gly Gly Glu Ala Val His Glu
        250                 255                 260
Val Glu Val Val Ile Lys His Asn Arg Phe Thr Lys Glu Thr Tyr Asp
265                 270                 275                 280
Phe Asp Ile Ala Val Leu Arg Leu Lys Thr Pro Ile Thr Phe Arg Met
                    285                 290                 295
Asn Val Ala Pro Ala Cys Leu Pro Glu Arg Asp Trp Ala Glu Ser Thr
                300                 305                 310
Leu Met Thr Gln Lys Thr Gly Ile Val Ser Gly Phe Gly Arg Thr His
            315                 320                 325
Glu Lys Gly Arg Gln Ser Thr Arg Leu Lys Met Leu Glu Val Pro Tyr
        330                 335                 340
Val Asp Arg Asn Ser Cys Lys Leu Ser Ser Ser Phe Ile Ile Thr Gln
345                 350                 355                 360
Asn Met Phe Cys Ala Gly Tyr Asp Thr Lys Gln Glu Asp Ala Cys Gln
                    365                 370                 375
Gly Asp Ser Gly Gly Pro His Val Thr Arg Phe Lys Asp Thr Tyr Phe
                380                 385                 390
Val Thr Gly Ile Val Ser Trp Gly Glu Gly Cys Ala Arg Lys Gly Lys
            395                 400                 405
Tyr Gly Ile Tyr Thr Lys Val Thr Ala Phe Leu Lys Trp Ile Asp Arg
        410                 415                 420
Ser Met Lys Thr Arg Gly Leu Pro Lys Ala Lys Ser His Ala Pro Glu
425                 430                 435                 440
Val Ile Thr Ser Ser Pro Leu Lys
                445

<210> SEQ ID NO 12
<211> LENGTH: 448
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Glu or gamma-carboxyglutamic acid
<220> FEATURE:
<221> NAME/KEY: MOD_RES
<222> LOCATION: (14)..(14)
<223> OTHER INFORMATION: Glu or gamma-carboxyglutamic acid
<220> FEATURE:
<221> NAME/KEY: MOD_RES
<222> LOCATION: (16)..(16)
<223> OTHER INFORMATION: Glu or gamma-carboxyglutamic acid
<220> FEATURE:
<221> NAME/KEY: MOD_RES
<222> LOCATION: (19)..(20)
<223> OTHER INFORMATION: Glu or gamma-carboxyglutamic acid
<220> FEATURE:
<221> NAME/KEY: MOD_RES
<222> LOCATION: (25)..(26)
<223> OTHER INFORMATION: Glu or gamma-carboxyglutamic acid
<220> FEATURE:
<221> NAME/KEY: MOD_RES
<222> LOCATION: (29)..(29)
<223> OTHER INFORMATION: Glu or gamma-carboxyglutamic acid
<220> FEATURE:
<221> NAME/KEY: MOD_RES
<222> LOCATION: (32)..(32)
<223> OTHER INFORMATION: Glu or gamma-carboxyglutamic acid
<220> FEATURE:
<221> NAME/KEY: MOD_RES
<222> LOCATION: (39)..(39)
<223> OTHER INFORMATION: Glu or gamma-carboxyglutamic acid

<400> SEQUENCE: 12
```

```
Ala Asn Ser Phe Leu Xaa Xaa Met Lys Lys Gly His Leu Xaa Arg Xaa
1               5                   10                  15

Cys Met Xaa Xaa Thr Cys Ser Tyr Xaa Xaa Ala Arg Xaa Val Phe Xaa
            20                  25                  30

Asp Ser Asp Lys Thr Asn Xaa Phe Trp Asn Lys Tyr Lys Asp Gly Asp
                35              40                  45

Gln Cys Glu Thr Ser Pro Cys Gln Asn Gln Gly Lys Cys Lys Asp Gly
            50              55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
            115                 120                 125

Pro Tyr Pro Cys Gly Lys Gln Thr Leu Glu Arg Arg Lys Arg Ser Val
            130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
                180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
            290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415
```

```
Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

<210> SEQ ID NO 13
<211> LENGTH: 1869
<212> TYPE: DNA
<213> ORGANISM: Homo sapiens
<220> FEATURE:
<221> NAME/KEY: CDS
<222> LOCATION: (1)..(1866)
<220> FEATURE:
<221> NAME/KEY: sig_peptide
<222> LOCATION: (1)..(129)
<220> FEATURE:
<221> NAME/KEY: mat_peptide
<222> LOCATION: (130)..(1866)

<400> SEQUENCE: 13 atg gcg cac gtc cga ggc ttg cag ctg cct ggc tgc ctg gcc ctg gct        48
Met Ala His Val Arg Gly Leu Gln Leu Pro Gly Cys Leu Ala Leu Ala
        -40                 -35                 -30 gcc ctg tgt agc ctt gtg cac agc cag cat gtg ttc ctg gct cct cag        96
Ala Leu Cys Ser Leu Val His Ser Gln His Val Phe Leu Ala Pro Gln
    -25                 -20                 -15 caa gca cgg tcg ctg ctc cag cgg gtc cgg cga gcc aac acc ttc ttg       144
Gln Ala Arg Ser Leu Leu Gln Arg Val Arg Arg Ala Asn Thr Phe Leu
-10                  -5                  -1  1                 5 gag gag gtg cgc aag ggc aac cta gag cga gag tgc gtg gag gag acg       192
Glu Glu Val Arg Lys Gly Asn Leu Glu Arg Glu Cys Val Glu Glu Thr
                10                  15                  20 tgc agc tac gag gag gcc ttc gag gct ctg gag tcc tcc acg gct acg       240
Cys Ser Tyr Glu Glu Ala Phe Glu Ala Leu Glu Ser Ser Thr Ala Thr
            25                  30                  35 gat gtg ttc tgg gcc aag tac aca gct tgt gag aca gcg agg acg cct       288
Asp Val Phe Trp Ala Lys Tyr Thr Ala Cys Glu Thr Ala Arg Thr Pro
        40                  45                  50 cga gat aag ctt gct gca tgt ctg gaa ggt aac tgt gct gag ggt ctg       336
Arg Asp Lys Leu Ala Ala Cys Leu Glu Gly Asn Cys Ala Glu Gly Leu
    55                  60                  65 ggt acg aac tac cga ggg cat gtg aac atc acc cgg tca ggc att gag       384
Gly Thr Asn Tyr Arg Gly His Val Asn Ile Thr Arg Ser Gly Ile Glu
70                  75                  80                  85 tgc cag cta tgg agg agt cgc tac cca cat aag cct gaa atc aac tcc       432
Cys Gln Leu Trp Arg Ser Arg Tyr Pro His Lys Pro Glu Ile Asn Ser
                90                  95                 100 act acc cat cct ggg gcc gac cta cag gag aat ttc tgc cgc aac ccc       480
Thr Thr His Pro Gly Ala Asp Leu Gln Glu Asn Phe Cys Arg Asn Pro
            105                 110                 115 gac agc agc acc acg gga ccc tgg tgc tac act aca gac ccc acc gtg       528
Asp Ser Ser Thr Thr Gly Pro Trp Cys Tyr Thr Thr Asp Pro Thr Val
        120                 125                 130 agg agg cag gaa tgc agc atc cct gtc tgt ggc cag gat caa gtc act       576
Arg Arg Gln Glu Cys Ser Ile Pro Val Cys Gly Gln Asp Gln Val Thr
    135                 140                 145 gta gcg atg act cca cgc tcc gaa ggc tcc agt gtg aat ctg tca cct       624
Val Ala Met Thr Pro Arg Ser Glu Gly Ser Ser Val Asn Leu Ser Pro
150                 155                 160                 165 cca ttg gag cag tgt gtc cct gat cgg ggg cag cag tac cag ggg cgc       672
Pro Leu Glu Gln Cys Val Pro Asp Arg Gly Gln Gln Tyr Gln Gly Arg
                170                 175                 180
```

```
ctg gcg gtg acc aca cat ggg ctc ccc tgc ctg gcc tgg gcc agc gca       720
Leu Ala Val Thr Thr His Gly Leu Pro Cys Leu Ala Trp Ala Ser Ala
            185                 190                 195 cag gcc aag gcc ctg agc aag cac cag gac ttc aac tca gct gtg cag       768
Gln Ala Lys Ala Leu Ser Lys His Gln Asp Phe Asn Ser Ala Val Gln
        200                 205                 210 ctg gtg gag aac ttc tgc cgc aac cca gac ggg gat gag gag ggc gtg       816
Leu Val Glu Asn Phe Cys Arg Asn Pro Asp Gly Asp Glu Glu Gly Val
    215                 220                 225 tgg tgc tat gtg gcc ggg aag cct ggc gac ttt ggg tac tgc gac ctc       864
Trp Cys Tyr Val Ala Gly Lys Pro Gly Asp Phe Gly Tyr Cys Asp Leu
230                 235                 240                 245 aac tat tgt gag gag gcc gtg gag gag gag aca gga gat ggg ctg gat       912
Asn Tyr Cys Glu Glu Ala Val Glu Glu Glu Thr Gly Asp Gly Leu Asp
                250                 255                 260 gag gac tca gac agg gcc atc gaa ggg cgt acc gcc acc agt gag tac       960
Glu Asp Ser Asp Arg Ala Ile Glu Gly Arg Thr Ala Thr Ser Glu Tyr
            265                 270                 275 cag act ttc ttc aat ccg agg acc ttt ggc tcg gga gag gca gac tgt      1008
Gln Thr Phe Phe Asn Pro Arg Thr Phe Gly Ser Gly Glu Ala Asp Cys
        280                 285                 290 ggg ctg cga cct ctg ttc gag aag aag tcg ctg gag gac aaa acc gaa      1056
Gly Leu Arg Pro Leu Phe Glu Lys Lys Ser Leu Glu Asp Lys Thr Glu
    295                 300                 305 aga gag ctc ctg gaa tcc tac atc gac ggg cgc att gtg gag ggc tcg      1104
Arg Glu Leu Leu Glu Ser Tyr Ile Asp Gly Arg Ile Val Glu Gly Ser
310                 315                 320                 325 gat gca gag atc ggc atg tca cct tgg cag gtg atg ctt ttc cgg aag      1152
Asp Ala Glu Ile Gly Met Ser Pro Trp Gln Val Met Leu Phe Arg Lys
                330                 335                 340 agt ccc cag gag ctg ctg tgt ggg gcc agc ctc atc agt gac cgc tgg      1200
Ser Pro Gln Glu Leu Leu Cys Gly Ala Ser Leu Ile Ser Asp Arg Trp
            345                 350                 355 gtc ctc acc gcc gcc cac tgc ctc ctg tac ccg ccc tgg gac aag aac      1248
Val Leu Thr Ala Ala His Cys Leu Leu Tyr Pro Pro Trp Asp Lys Asn
        360                 365                 370 ttc acc gag aat gac ctt ctg gtg cgc att ggc aag cac tcc cgc aca      1296
Phe Thr Glu Asn Asp Leu Leu Val Arg Ile Gly Lys His Ser Arg Thr
    375                 380                 385 agg tac gag cga aac att gaa aag ata tcc atg ttg gaa aag atc tac      1344
Arg Tyr Glu Arg Asn Ile Glu Lys Ile Ser Met Leu Glu Lys Ile Tyr
390                 395                 400                 405 atc cac ccc agg tac aac tgg cgg gag aac ctg gac cgg gac att gcc      1392
Ile His Pro Arg Tyr Asn Trp Arg Glu Asn Leu Asp Arg Asp Ile Ala
                410                 415                 420 ctg atg aag ctg aag aag cct gtt gcc ttc agt gac tac att cac cct      1440
Leu Met Lys Leu Lys Lys Pro Val Ala Phe Ser Asp Tyr Ile His Pro
            425                 430                 435 gtg tgt ctg ccc gac agg gag acg gca gcc agc ttg ctc cag gct gga      1488
Val Cys Leu Pro Asp Arg Glu Thr Ala Ala Ser Leu Leu Gln Ala Gly
        440                 445                 450 tac aag ggg cgg gtg aca ggc tgg ggc aac ctg aag gag acg tgg aca      1536
Tyr Lys Gly Arg Val Thr Gly Trp Gly Asn Leu Lys Glu Thr Trp Thr
    455                 460                 465 gcc aac gtt ggt aag ggg cag ccc agt gtc ctg cag gtg gtg aac ctg      1584
Ala Asn Val Gly Lys Gly Gln Pro Ser Val Leu Gln Val Val Asn Leu
470                 475                 480                 485 ccc att gtg gag cgg ccg gtc tgc aag gac tcc acc cgg atc cgc atc      1632
Pro Ile Val Glu Arg Pro Val Cys Lys Asp Ser Thr Arg Ile Arg Ile
                490                 495                 500
```

-continued

```
act gac aac atg ttc tgt gct ggt tac aag cct gat gaa ggg aaa cga      1680
Thr Asp Asn Met Phe Cys Ala Gly Tyr Lys Pro Asp Glu Gly Lys Arg
            505                 510                 515 ggg gat gcc tgt gaa ggt gac agt ggg gga ccc ttt gtc atg aag agc      1728
Gly Asp Ala Cys Glu Gly Asp Ser Gly Gly Pro Phe Val Met Lys Ser
        520                 525                 530 ccc ttt aac aac cgc tgg tat caa atg ggc atc gtc tca tgg ggt gaa      1776
Pro Phe Asn Asn Arg Trp Tyr Gln Met Gly Ile Val Ser Trp Gly Glu
    535                 540                 545 ggc tgt gac cgg gat ggg aaa tat ggc ttc tac aca cat gtg ttc cgc      1824
Gly Cys Asp Arg Asp Gly Lys Tyr Gly Phe Tyr Thr His Val Phe Arg
550                 555                 560                 565 ctg aag aag tgg ata cag aag gtc att gat cag ttt gga gag tag          1869
Leu Lys Lys Trp Ile Gln Lys Val Ile Asp Gln Phe Gly Glu
                570                 575
```

<210> SEQ ID NO 14
<211> LENGTH: 622
<212> TYPE: PRT
<213> ORGANISM: Homo sapiens

<400> SEQUENCE: 14

```
Met Ala His Val Arg Gly Leu Gln Leu Pro Gly Cys Leu Ala Leu Ala
            -40                 -35                 -30

Ala Leu Cys Ser Leu Val His Ser Gln His Val Phe Leu Ala Pro Gln
        -25                 -20                 -15

Gln Ala Arg Ser Leu Leu Gln Arg Val Arg Arg Ala Asn Thr Phe Leu
    -10                  -5                  -1   1               5

Glu Glu Val Arg Lys Gly Asn Leu Glu Arg Glu Cys Val Glu Glu Thr
                 10                  15                  20

Cys Ser Tyr Glu Glu Ala Phe Glu Ala Leu Glu Ser Ser Thr Ala Thr
             25                  30                  35

Asp Val Phe Trp Ala Lys Tyr Thr Ala Cys Glu Thr Ala Arg Thr Pro
         40                  45                  50

Arg Asp Lys Leu Ala Ala Cys Leu Glu Gly Asn Cys Ala Glu Gly Leu
     55                  60                  65

Gly Thr Asn Tyr Arg Gly His Val Asn Ile Thr Arg Ser Gly Ile Glu
 70                  75                  80                  85

Cys Gln Leu Trp Arg Ser Arg Tyr Pro His Lys Pro Glu Ile Asn Ser
                 90                  95                 100

Thr Thr His Pro Gly Ala Asp Leu Gln Glu Asn Phe Cys Arg Asn Pro
            105                 110                 115

Asp Ser Ser Thr Thr Gly Pro Trp Cys Tyr Thr Thr Asp Pro Thr Val
        120                 125                 130

Arg Arg Gln Glu Cys Ser Ile Pro Val Cys Gly Gln Asp Gln Val Thr
    135                 140                 145

Val Ala Met Thr Pro Arg Ser Glu Gly Ser Ser Val Asn Leu Ser Pro
150                 155                 160                 165

Pro Leu Glu Gln Cys Val Pro Asp Arg Gly Gln Gln Tyr Gln Gly Arg
                170                 175                 180

Leu Ala Val Thr Thr His Gly Leu Pro Cys Leu Ala Trp Ala Ser Ala
            185                 190                 195

Gln Ala Lys Ala Leu Ser Lys His Gln Asp Phe Asn Ser Ala Val Gln
        200                 205                 210

Leu Val Glu Asn Phe Cys Arg Asn Pro Asp Gly Asp Glu Glu Gly Val
    215                 220                 225
```

```
Trp Cys Tyr Val Ala Gly Lys Pro Gly Asp Phe Gly Tyr Cys Asp Leu
230                 235                 240                 245

Asn Tyr Cys Glu Glu Ala Val Glu Glu Thr Gly Asp Gly Leu Asp
            250                 255                 260

Glu Asp Ser Asp Arg Ala Ile Gly Arg Thr Ala Thr Ser Glu Tyr
            265                 270                 275

Gln Thr Phe Phe Asn Pro Arg Thr Phe Gly Ser Gly Glu Ala Asp Cys
        280                 285                 290

Gly Leu Arg Pro Leu Phe Glu Lys Lys Ser Leu Glu Asp Lys Thr Glu
295                 300                 305

Arg Glu Leu Leu Glu Ser Tyr Ile Asp Gly Arg Ile Val Glu Gly Ser
310                 315                 320                 325

Asp Ala Glu Ile Gly Met Ser Pro Trp Gln Val Met Leu Phe Arg Lys
                330                 335                 340

Ser Pro Gln Glu Leu Leu Cys Gly Ala Ser Leu Ile Ser Asp Arg Trp
            345                 350                 355

Val Leu Thr Ala Ala His Cys Leu Leu Tyr Pro Pro Trp Asp Lys Asn
            360                 365                 370

Phe Thr Glu Asn Asp Leu Leu Val Arg Ile Gly Lys His Ser Arg Thr
375                 380                 385

Arg Tyr Glu Arg Asn Ile Glu Lys Ile Ser Met Leu Glu Lys Ile Tyr
390                 395                 400                 405

Ile His Pro Arg Tyr Asn Trp Arg Glu Asn Leu Asp Arg Asp Ile Ala
                410                 415                 420

Leu Met Lys Leu Lys Lys Pro Val Ala Phe Ser Asp Tyr Ile His Pro
                425                 430                 435

Val Cys Leu Pro Asp Arg Glu Thr Ala Ala Ser Leu Leu Gln Ala Gly
                440                 445                 450

Tyr Lys Gly Arg Val Thr Gly Trp Gly Asn Leu Lys Glu Thr Trp Thr
            455                 460                 465

Ala Asn Val Gly Lys Gly Gln Pro Ser Val Leu Gln Val Val Asn Leu
470                 475                 480                 485

Pro Ile Val Glu Arg Pro Val Cys Lys Asp Ser Thr Arg Ile Arg Ile
                490                 495                 500

Thr Asp Asn Met Phe Cys Ala Gly Tyr Lys Pro Asp Glu Gly Lys Arg
            505                 510                 515

Gly Asp Ala Cys Glu Gly Asp Ser Gly Gly Pro Phe Val Met Lys Ser
            520                 525                 530

Pro Phe Asn Asn Arg Trp Tyr Gln Met Gly Ile Val Ser Trp Gly Glu
            535                 540                 545

Gly Cys Asp Arg Asp Gly Lys Tyr Gly Phe Tyr Thr His Val Phe Arg
550                 555                 560                 565

Leu Lys Lys Trp Ile Gln Lys Val Ile Asp Gln Phe Gly Glu
                570                 575
```

<210> SEQ ID NO 15
<211> LENGTH: 579
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Glu or gamma-carboxyglutamic acid
<220> FEATURE:
<221> NAME/KEY: MOD_RES
<222> LOCATION: (14)..(14)

```
<223> OTHER INFORMATION: Glu or gamma-carboxyglutamic acid
<220> FEATURE:
<221> NAME/KEY: MOD_RES
<222> LOCATION: (16)..(16)
<223> OTHER INFORMATION: Glu or gamma-carboxyglutamic acid
<220> FEATURE:
<221> NAME/KEY: MOD_RES
<222> LOCATION: (19)..(20)
<223> OTHER INFORMATION: Glu or gamma-carboxyglutamic acid
<220> FEATURE:
<221> NAME/KEY: MOD_RES
<222> LOCATION: (25)..(26)
<223> OTHER INFORMATION: Glu or gamma-carboxyglutamic acid
<220> FEATURE:
<221> NAME/KEY: MOD_RES
<222> LOCATION: (29)..(29)
<223> OTHER INFORMATION: Glu or gamma-carboxyglutamic acid
<220> FEATURE:
<221> NAME/KEY: MOD_RES
<222> LOCATION: (32)..(32)
<223> OTHER INFORMATION: Glu or gamma-carboxyglutamic acid

<400> SEQUENCE: 15
```

Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu

```
                290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu
                405                 410                 415

Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 16
<211> LENGTH: 8
<212> TYPE: PRT
<213> ORGANISM: Homo sapiens

<400> SEQUENCE: 16

Asn Ala Ser Lys Pro Gln Gly Arg
1               5

<210> SEQ ID NO 17
<211> LENGTH: 17
<212> TYPE: PRT
<213> ORGANISM: Homo sapiens

<400> SEQUENCE: 17

Ser His Leu Lys Arg Asp Thr Glu Asp Gln Glu Asp Gln Val Asp Pro
1               5                   10                  15

Arg
```

<210> SEQ ID NO 18
<211> LENGTH: 35
<212> TYPE: PRT
<213> ORGANISM: Homo sapiens

<400> SEQUENCE: 18

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 19
<211> LENGTH: 52
<212> TYPE: PRT
<213> ORGANISM: Homo sapiens

<400> SEQUENCE: 19

Ser Val Ala Gln Ala Thr Ser Ser Gly Glu Ala Pro Asp Ser Ile
1               5                   10                  15

Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
        35                  40                  45

Asn Leu Thr Arg
    50

<210> SEQ ID NO 20
<211> LENGTH: 49
<212> TYPE: PRT
<213> ORGANISM: Homo sapiens

<400> SEQUENCE: 20

Thr Ala Thr Ser Glu Tyr Gln Thr Phe Phe Asn Pro Arg Thr Phe Gly
1               5                   10                  15

Ser Gly Glu Ala Asp Cys Gly Leu Arg Pro Leu Phe Glu Lys Lys Ser
            20                  25                  30

Leu Glu Asp Lys Thr Glu Arg Glu Leu Leu Glu Ser Tyr Ile Asp Gly
        35                  40                  45

Arg

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctattctag aaaaaagaaa tgctagcaaa ccccaaggcc g                          41

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggccttggg gtttgctagc atttcttttt tctagaatag g         41

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtggctagcg ctgagactgt ttttcctg         28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cacgctagct tgggtgcttt gagtgatg         28

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctagaaaaaa gaaatgctcg tgctgagact gttttcctg atgtgg         46

<210> SEQ ID NO 26
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccacatcagg aaaaacagtc tcagcacgag catttctttt ttctag         46

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catcactcaa agcacccaat caagcaaacc ccaaggccga attg         44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
caattcggcc ttggggtttg cttgattggg tgctttgagt gatg                     44
```

<210> SEQ ID NO 29
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Arg Ala Glu Thr Val Phe Pro Asp Val Asp Tyr Val Asn Ser
145                 150                 155                 160

Thr Glu Ala Glu Thr Ile Leu Asp Asn Ile Thr Gln Ser Thr Gln Ser
                165                 170                 175

Ser Lys Pro Gln Gly Arg Ile Val Gly Gly Lys Val Cys Pro Lys Gly
            180                 185                 190

Glu Cys Pro Trp Gln Val Leu Leu Leu Val Asn Gly Ala Gln Leu Cys
        195                 200                 205

Gly Gly Thr Leu Ile Asn Thr Ile Trp Val Val Ser Ala Ala His Cys
    210                 215                 220

Phe Asp Lys Ile Lys Asn Trp Arg Asn Leu Ile Ala Val Leu Gly Glu
225                 230                 235                 240

His Asp Leu Ser Glu His Asp Gly Asp Glu Gln Ser Arg Arg Val Ala
                245                 250                 255

Gln Val Ile Ile Pro Ser Thr Tyr Val Pro Gly Thr Thr Asn His Asp
            260                 265                 270

Ile Ala Leu Leu Arg Leu His Gln Pro Val Val Leu Thr Asp His Val
        275                 280                 285

Val Pro Leu Cys Leu Pro Glu Arg Thr Phe Ser Glu Arg Thr Leu Ala
    290                 295                 300

Phe Val Arg Phe Ser Leu Val Ser Gly Trp Gly Gln Leu Leu Asp Arg
305                 310                 315                 320

Gly Ala Thr Ala Leu Glu Leu Met Val Leu Asn Val Pro Arg Leu Met
                325                 330                 335

Thr Gln Asp Cys Leu Gln Gln Ser Arg Lys Val Gly Asp Ser Pro Asn
            340                 345                 350
```

```
Ile Thr Glu Tyr Met Phe Cys Ala Gly Tyr Ser Asp Gly Ser Lys Asp
            355                 360                 365

Ser Cys Lys Gly Asp Ser Gly Gly Pro His Ala Thr His Tyr Arg Gly
        370                 375                 380

Thr Trp Tyr Leu Thr Gly Ile Val Ser Trp Gly Gln Gly Cys Ala Thr
385                 390                 395                 400

Val Gly His Phe Gly Val Tyr Thr Arg Val Ser Gln Tyr Ile Glu Trp
                405                 410                 415

Leu Gln Lys Leu Met Arg Ser Glu Pro Arg Pro Gly Val Leu Leu Arg
            420                 425                 430

Ala Pro Phe Pro
        435

<210> SEQ ID NO 30
<211> LENGTH: 30
<212> TYPE: PRT
<213> ORGANISM: Homo sapiens

<400> SEQUENCE: 30

Arg Ala Glu Ala Val Phe Pro Asp Val Asp Tyr Val Asn Ser Thr Glu
1               5                   10                  15

Ala Glu Thr Ile Leu Asp Asn Ile Thr Gln Ser Thr Gln Ser
            20                  25                  30

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaagagtttc tgtttcacaa acttctagac tcacccgtgc tgagac          46

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtctcagcac gggtgagtct agaagtttgt gaaacagaaa ctcttc          46

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggataacatc actcaaagca ccggttcatt taatgacttc actcgggttg      50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 34
caacccgagt gaagtcatta aatgaaccgg tgctttgagt gatgttatcc          50

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtgtctagaa ggaagaggtc agtggccc                                  28

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacaccggtg aggttgttgt cgccc                                     25

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gagtttctgt ttcacaaact tctcgcagga agaggtcagt gg                  42

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccactgacct cttcctgcga gaagtttgtg aaacagaaac tc                  42

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcgacaacaa cctcacccaa tcatttaatg acttcactcg ggttg               45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 40
caacccgagt gaagtcatta aatgattggg tgaggttgtt gtcgc                    45

<210> SEQ ID NO 41
<211> LENGTH: 439
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41
```

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Arg Arg Lys
    130                 135                 140

Arg Ser Val Ala Gln Ala Thr Ser Ser Ser Gly Glu Ala Pro Asp Ser
145                 150                 155                 160

Ile Thr Trp Lys Pro Tyr Asp Ala Ala Asp Leu Asp Pro Thr Glu Asn
                165                 170                 175

Pro Phe Asp Leu Leu Asp Phe Asn Gln Thr Gln Pro Glu Arg Gly Asp
            180                 185                 190

Asn Asn Leu Thr Gln Ser Phe Asn Asp Phe Thr Arg Val Val Gly Gly
        195                 200                 205

Glu Asp Ala Lys Pro Gly Gln Phe Pro Trp Gln Val Val Leu Asn Gly
    210                 215                 220

Lys Val Asp Ala Phe Cys Gly Gly Ser Ile Val Asn Glu Lys Trp Ile
225                 230                 235                 240

Val Thr Ala Ala His Cys Val Glu Thr Gly Val Lys Ile Thr Val Val
                245                 250                 255

Ala Gly Glu His Asn Ile Glu Glu Thr Glu His Thr Glu Gln Lys Arg
            260                 265                 270

Asn Val Ile Arg Ile Ile Pro His His Asn Tyr Asn Ala Ala Ile Asn
        275                 280                 285

Lys Tyr Asn His Asp Ile Ala Leu Leu Glu Leu Asp Glu Pro Leu Val
    290                 295                 300

Leu Asn Ser Tyr Val Thr Pro Ile Cys Ile Ala Asp Lys Glu Tyr Thr
305                 310                 315                 320

Asn Ile Phe Leu Lys Phe Gly Ser Gly Tyr Val Ser Gly Trp Gly Arg
                325                 330                 335

Val Phe His Lys Gly Arg Ser Ala Leu Val Leu Gln Tyr Leu Arg Val

```
                    340                 345                 350
Pro Leu Val Asp Arg Ala Thr Cys Leu Arg Ser Thr Lys Phe Thr Ile
                355                 360                 365

Tyr Asn Asn Met Phe Cys Ala Gly Phe His Glu Gly Arg Asp Ser
370                 375                 380

Cys Gln Gly Asp Ser Gly Gly Pro His Val Thr Glu Val Glu Gly Thr
385                 390                 395                 400

Ser Phe Leu Thr Gly Ile Ile Ser Trp Gly Glu Glu Cys Ala Met Lys
                405                 410                 415

Gly Lys Tyr Gly Ile Tyr Thr Lys Val Ser Arg Tyr Val Asn Trp Ile
                420                 425                 430

Lys Glu Lys Thr Lys Leu Thr
                435

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctattctaga aaaagagct gagactgttt ttcctgatg                              39

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
catcaggaaa aacagtctca gctcttttt ctagaatag                              39

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caaagcaccc aatcaaagcg gaatgctagc aaaccccaag g                          41

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccttggggtt tgctagcatt ccgctttgat tgggtgcttt g                          41

<210> SEQ ID NO 46
<211> LENGTH: 436
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 46

```
Ala Asn Ala Phe Leu Glu Glu Leu Arg Pro Gly Ser Leu Glu Arg Glu
 1               5                  10                  15

Cys Lys Glu Glu Gln Cys Ser Phe Glu Glu Ala Arg Glu Ile Phe Lys
             20                  25                  30

Asp Ala Glu Arg Thr Lys Leu Phe Trp Ile Ser Tyr Ser Asp Gly Asp
         35                  40                  45

Gln Cys Ala Ser Ser Pro Cys Gln Asn Gly Gly Ser Cys Lys Asp Gln
     50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                 85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Arg Ala Glu Thr Val Phe Pro Asp Val Asp Tyr Val Asn Ser
145                 150                 155                 160

Thr Glu Ala Glu Thr Ile Leu Asp Asn Ile Thr Gln Ser Thr Gln Ser
                165                 170                 175

Ser Lys Pro Gln Gly Arg Ile Val Gly Gly Lys Val Cys Pro Lys Gly
            180                 185                 190

Glu Cys Pro Trp Gln Val Leu Leu Leu Val Asn Gly Ala Gln Leu Cys
        195                 200                 205

Gly Gly Thr Leu Ile Asn Thr Ile Trp Val Val Ser Ala Ala His Cys
    210                 215                 220

Phe Asp Lys Ile Lys Asn Trp Arg Asn Leu Ile Ala Val Leu Gly Glu
225                 230                 235                 240

His Asp Leu Ser Glu His Asp Gly Asp Glu Gln Ser Arg Arg Val Ala
                245                 250                 255

Gln Val Ile Ile Pro Ser Thr Tyr Val Pro Gly Thr Thr Asn His Asp
            260                 265                 270

Ile Ala Leu Leu Arg Leu His Gln Pro Val Val Leu Thr Asp His Val
        275                 280                 285

Val Pro Leu Cys Leu Pro Glu Arg Thr Phe Ser Glu Arg Thr Leu Ala
    290                 295                 300

Phe Val Arg Phe Ser Leu Val Ser Gly Trp Gly Gln Leu Leu Asp Arg
305                 310                 315                 320

Gly Ala Thr Ala Leu Glu Leu Met Val Leu Asn Val Pro Arg Leu Met
                325                 330                 335

Thr Gln Asp Cys Leu Gln Gln Ser Arg Lys Val Gly Asp Ser Pro Asn
            340                 345                 350

Ile Thr Glu Tyr Met Phe Cys Ala Gly Tyr Ser Asp Gly Ser Lys Asp
        355                 360                 365

Ser Cys Lys Gly Asp Ser Gly Gly Pro His Ala Thr His Tyr Arg Gly
    370                 375                 380

Thr Trp Tyr Leu Thr Gly Ile Val Ser Trp Gly Gln Gly Cys Ala Thr
385                 390                 395                 400
```

Val Gly His Phe Gly Val Tyr Thr Arg Val Ser Gln Tyr Ile Glu Trp
            405                 410                 415

Leu Gln Lys Leu Met Arg Ser Glu Pro Arg Pro Gly Val Leu Leu Arg
        420                 425                 430

Ala Pro Phe Pro
        435

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtggctagcc aggccaccag cagcag                                    26

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcggctagca ttccgcttct caggctgcgt ctggttg                        37

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cctattctag aaaaaagaaa tgcccaggcc accagcagca gcgg                44

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccgctgctgc tggtggcctg ggcatttctt ttttctagaa tagg                44

<210> SEQ ID NO 51
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cctattctag aaaaaagcgt ggcccaggcc accagcagca gcgggg              46

<210> SEQ ID NO 52
<211> LENGTH: 46
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 52
ccccgctgct gctggtggcc tgggccacgc ttttttctag aatagg                    46

<210> SEQ ID NO 53
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Ser
    130                 135                 140

Val Ala Gln Ala Thr Ser Ser Ser Gly Glu Ala Pro Asp Ser Ile Thr
145                 150                 155                 160

Trp Lys Pro Tyr Asp Ala Ala Asp Leu Asp Pro Thr Glu Asn Pro Phe
                165                 170                 175

Asp Leu Leu Asp Phe Asn Gln Thr Gln Pro Glu Lys Arg Asn Ala Ser
            180                 185                 190

Lys Pro Gln Gly Arg Ile Val Gly Gly Lys Val Cys Pro Lys Gly Glu
        195                 200                 205

Cys Pro Trp Gln Val Leu Leu Leu Val Asn Gly Ala Gln Leu Cys Gly
    210                 215                 220

Gly Thr Leu Ile Asn Thr Ile Trp Val Val Ser Ala Ala His Cys Phe
225                 230                 235                 240

Asp Lys Ile Lys Asn Trp Arg Asn Leu Ile Ala Val Leu Gly Glu His
                245                 250                 255

Asp Leu Ser Glu His Asp Gly Asp Glu Gln Ser Arg Arg Val Ala Gln
            260                 265                 270

Val Ile Ile Pro Ser Thr Tyr Val Pro Gly Thr Thr Asn His Asp Ile
        275                 280                 285

Ala Leu Leu Arg Leu His Gln Pro Val Val Leu Thr Asp His Val Val
    290                 295                 300

Pro Leu Cys Leu Pro Glu Arg Thr Phe Ser Glu Arg Thr Leu Ala Phe
305                 310                 315                 320

Val Arg Phe Ser Leu Val Ser Gly Trp Gly Gln Leu Leu Asp Arg Gly
            325                 330                 335

Ala Thr Ala Leu Glu Leu Met Val Leu Asn Val Pro Arg Leu Met Thr
        340                 345                 350

Gln Asp Cys Leu Gln Gln Ser Arg Lys Val Gly Asp Ser Pro Asn Ile
        355                 360                 365

Thr Glu Tyr Met Phe Cys Ala Gly Tyr Ser Asp Gly Ser Lys Asp Ser
    370                 375                 380

Cys Lys Gly Asp Ser Gly Gly Pro His Ala Thr His Tyr Arg Gly Thr
385                 390                 395                 400

Trp Tyr Leu Thr Gly Ile Val Ser Trp Gly Gln Gly Cys Ala Thr Val
                405                 410                 415

Gly His Phe Gly Val Tyr Thr Arg Val Ser Gln Tyr Ile Glu Trp Leu
            420                 425                 430

Gln Lys Leu Met Arg Ser Glu Pro Arg Pro Gly Val Leu Leu Arg Ala
        435                 440                 445

Pro Phe Pro
    450

<210> SEQ ID NO 54
<211> LENGTH: 466
<212> TYPE: PRT
<213> ORGANISM: Homo sapiens

<400> SEQUENCE: 54

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Asp Val Asn Glu Asn Gly Gly Cys Glu Gln
145                 150                 155                 160

Tyr Asp Ser Asp His Thr Gly Thr Lys Arg Ser Asp Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205

Pro Gln Gly Arg Ile Val Gly Gly Lys Val Cys Pro Lys Gly Glu Cys
    210                 215                 220

Pro Trp Gln Val Leu Leu Leu Val Asn Gly Ala Gln Leu Cys Gly Gly
225                 230                 235                 240

```
Thr Leu Ile Asn Thr Ile Trp Val Val Ser Ala Ala His Cys Phe Asp
            245                 250                 255

Lys Ile Lys Asn Trp Arg Asn Leu Ile Ala Val Leu Gly Glu His Asp
        260                 265                 270

Leu Ser Glu His Gln Gly Asp Glu Gln Ser Arg Arg Val Ala Gln Val
    275                 280                 285

Ile Ile Pro Ser Thr Tyr Val Pro Gly Thr Thr Asn His Asp Ile Ala
290                 295                 300

Leu Leu Arg Ile His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
    370                 375                 380

Glu Tyr Met Phe Cys Ala Gly Tyr Ser Asp Gly Ser Lys Asp Ser Cys
385                 390                 395                 400

Lys Gly Gln Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
    450                 455                 460

Phe Pro
465

<210> SEQ ID NO 55
<211> LENGTH: 444
<212> TYPE: PRT
<213> ORGANISM: Unknown
<220> FEATURE:
<223> OTHER INFORMATION: Description of Unknown Organism: Unknown animal
      vitamin K-dependent prothrombin sequence

<400> SEQUENCE: 55

Met Ala Pro Gln Ala Arg Gly Leu Gly Leu Cys Ser Leu Leu Ala Leu
1               5                   10                  15

Gln Ala Ser Leu Ala Ala Val Phe Ile Thr Gln Glu Glu Leu His Ser
            20                  25                  30

Val Leu Arg Arg Gln Arg Arg Ala Asn Ser Phe Leu Glu Glu Leu Arg
        35                  40                  45

Pro Gly Ser Leu Glu Arg Glu Asp Lys Glu Glu Leu Cys Ser Phe Glu
    50                  55                  60

Glu Ala Arg Glu Val Phe Gln Ser Thr Glu Arg Thr Lys Gln Phe Trp
65                  70                  75                  80

Ile Thr Tyr Asn Asp Gly Asp Gln Cys Ala Ser Asn Phe Cys Gln Asn
                85                  90                  95

Gly Gly Ser Cys Glu Cys Gln Ile Gln Ser Tyr Ile Cys Phe Cys Leu
            100                 105                 110

Ala Asp Phe Glu Gly Arg Asn Cys Glu Lys Asn Lys Asn Asp Gln Leu
```

```
                115                 120                 125
Ile Asp Met Tyr Glu Asn Gly Gly Cys Glu Gln Tyr Cys Ser Asp His
            130                 135                 140

Val Gly Ser Gln Arg Ser Cys Arg Cys His Glu Gly Tyr Thr Leu Leu
145                 150                 155                 160

Pro Asn Gly Val Ser Cys Thr Pro Thr Val Asp Tyr Pro Cys Gly Lys
                165                 170                 175

Val Pro Ala Leu Glu Lys Arg Gly Ala Ser Asn Pro Gln Gly Arg Ile
            180                 185                 190

Val Gly Gly Lys Val Cys Pro Lys Gly Glu Cys Pro Trp Gln Ala Ala
            195                 200                 205

Leu Met Asn Gly Ser Thr Leu Leu Cys Gly Gly Ser Leu Leu Asp Thr
        210                 215                 220

His Trp Val Val Ser Ala Ala His Asp Phe Asp Lys Leu Ser Ser Leu
225                 230                 235                 240

Arg Asn Leu Thr Ile Val Leu Gly Glu His Asp Leu Ser Glu His Glu
                245                 250                 255

Gly Asp Glu Gln Val Arg His Val Ala Gln Leu Leu Met Pro Asp Lys
            260                 265                 270

Tyr Val Pro Gly Lys Thr Asp His Asp Ile Ala Ala Leu Arg Leu Leu
        275                 280                 285

Gln Pro Ala Leu Leu Thr Asn Asn Val Val Pro Leu Cys Leu Pro Glu
    290                 295                 300

Arg Asn Phe Ser Glu Ser Thr Leu Ala Thr Ile Arg Phe Ser Arg Val
305                 310                 315                 320

Ser Gly Trp Gly Gln Leu Leu Tyr Arg Gly Ala Leu Ala Arg Glu Leu
                325                 330                 335

Met Ala Ile Asp Val Pro Arg Leu Met Thr Gln Asp Cys Val Glu Gln
            340                 345                 350

Ser Glu His Lys Pro Gly Ser Pro Glu Val Thr Gly Asn Met Phe Cys
        355                 360                 365

Ala Gly Tyr Leu Asp Gly Ser Lys Asp Ala Gln Lys Gly Asp Ser Gly
    370                 375                 380

Gly Pro His Ala Thr Ser Tyr His Gly Thr Trp Tyr Leu Thr Gly Val
385                 390                 395                 400

Val Ser Trp Gly Glu Gly Cys Ala Ala Val Gly His Val Gly Val Tyr
                405                 410                 415

Thr Arg Val Ser Arg Tyr Thr Glu Trp Leu Ser Arg Leu Met Arg Ser
            420                 425                 430

Lys Leu His His Gly Ile Gln Arg His Pro Phe Pro
        435                 440

<210> SEQ ID NO 56
<211> LENGTH: 406
<212> TYPE: PRT
<213> ORGANISM: Bos sp.

<400> SEQUENCE: 56

Ala Asn Gly Phe Leu Glu Glu Leu Leu Pro Gly Ser Leu Glu Arg Glu
1               5                   10                  15

Cys Arg Glu Glu Leu Cys Ser Phe Glu Glu Ala His Glu Ile Phe Arg
            20                  25                  30

Asn Glu Glu Arg Thr Arg Gln Phe Trp Val Ser Tyr Asn Asp Gly Asp
        35                  40                  45
```

```
Gln Cys Ala Ser Ser Pro Cys Gln Asn Gly Gly Ser Cys Glu Asp Gln
         50                  55                  60

Leu Arg Ser Tyr Ile Cys Phe Asp Phe Asp Gly Phe Glu Gly Arg Asn
 65                  70                  75                  80

Cys Glu Thr Asp Lys Gln Ser Gln Leu Ile Cys Ala Asn Asp Asn Gly
                 85                  90                  95

Gly Cys Glu Gln Tyr Cys Gly Ala Asp Pro Gly Ala Gly Arg Phe Cys
            100                 105                 110

Trp Cys His Glu Gly Tyr Ala Leu Gln Ala Asp Gly Val Ser Cys Ala
            115                 120                 125

Pro Thr Val Glu Tyr Pro Cys Gly Lys Ile Pro Val Leu Glu Lys Arg
130                 135                 140

Asn Gly Ser Lys Pro Gln Gly Arg Ile Val Gly Gly His Val Cys Pro
145                 150                 155                 160

Lys Gly Glu Cys Pro Trp Gln Ala Met Leu Lys Leu Asn Gly Ala Leu
                165                 170                 175

Leu Cys Gly Gly Thr Leu Val Gly Pro Ala Trp Val Val Ser Ala Ala
            180                 185                 190

His Cys Phe Glu Arg Leu Arg Ser Arg Gly Asn Leu Thr Ala Val Leu
            195                 200                 205

Gly Glu His Asp Leu Ser Arg Val Glu Gly Pro Glu Gln Glu Arg Arg
210                 215                 220

Val Ala Gln Ile Ile Val Pro Lys Gln Tyr Val Pro Gly Gln Thr Asp
225                 230                 235                 240

His Asp Val Ala Leu Leu Gln Leu Ala Gln Pro Val Ala Leu Gly Asp
                245                 250                 255

His Val Ala Pro Leu Cys Leu Pro Asp Pro Asp Phe Ala Asp Gln Thr
            260                 265                 270

Leu Ala Phe Val Arg Phe Ser Ala Val Ser Gly Trp Gly Gln Leu Leu
            275                 280                 285

Glu Arg Gly Val Thr Ala Arg Lys Leu Met Val Leu Val Pro Arg
290                 295                 300

Leu Leu Thr Gln Asp Cys Leu Gln Gln Ser Arg Gln Arg Pro Gly Gly
305                 310                 315                 320

Pro Val Val Thr Asp Asn Met Phe Cys Ala Gly Tyr Ser Asp Gly Ser
                325                 330                 335

Lys Asp Ala Cys Lys Gly Asp Ser Gly Gly Pro His Ala Thr Arg Phe
            340                 345                 350

Arg Gly Thr Trp Phe Leu Thr Gly Val Val Ser Trp Gly Glu Gly Cys
            355                 360                 365

Ala Ala Ala Gly His Phe Gly Ile Tyr Thr Arg Val Ser Arg Tyr Thr
370                 375                 380

Ala Trp Leu Arg Gln Leu Met Gly His Pro Pro Ser Arg Gln Gly Phe
385                 390                 395                 400

Phe Gln Val Pro Leu Leu
                405

<210> SEQ ID NO 57
<211> LENGTH: 446
<212> TYPE: PRT
<213> ORGANISM: Mus sp.

<400> SEQUENCE: 57

Met Val Pro Gln Ala His Gly Leu Leu Leu Leu Cys Phe Leu Leu Gln
 1               5                  10                  15
```

-continued

```
Leu Gln Gly Pro Leu Gly Thr Ala Val Phe Ile Thr Gln Glu Glu Ala
            20                  25                  30

His Gly Val Leu His Arg Gln Arg Ala Asn Ser Leu Leu Glu Glu
        35                  40                  45

Leu Trp Pro Gly Ser Leu Glu Arg Glu Cys Asn Glu Glu Gln Cys Ser
50                      55                  60

Phe Glu Glu Ala Arg Glu Ile Phe Lys Ser Pro Glu Arg Thr Lys Gln
65                  70                  75                  80

Phe Trp Ile Val Tyr Ser Asp Gly Asp Gln Cys Ala Ser Asn Phe Cys
                85                  90                  95

Gln Asn Gly Gly Thr Cys Gln Asp His Leu Lys Ser Tyr Val Cys Phe
                100                 105                 110

Asp Leu Leu Asp Phe Glu Gly Arg Asn Cys Glu Lys Ser Lys Asn Glu
            115                 120                 125

Gln Leu Ile Asp Ala Asn Glu Asn Gly Asp Cys Asp Gln Tyr Cys Arg
    130                 135                 140

Asp His Val Gly Thr Lys Arg Thr Cys Ser Cys His Glu Asp Tyr Thr
145                 150                 155                 160

Leu Gln Pro Asp Glu Val Ser Cys Lys Pro Lys Val Glu Tyr Pro Cys
                165                 170                 175

Gly Arg Ile Pro Val Val Glu Lys Arg Asn Ser Ser Ser Arg Gln Gly
                180                 185                 190

Arg Ile Val Gly Gly Asn Val Cys Pro Lys Gly Glu Cys Pro Trp Gln
            195                 200                 205

Ala Val Leu Lys Ile Asn Gly Leu Leu Leu Cys Gly Ala Val Leu Leu
        210                 215                 220

Asp Ala Arg Trp Ile Val Thr Ala Ala His Cys Phe Asp Asn Ile Arg
225                 230                 235                 240

Tyr Trp Gly Asn Ile Thr Val Val Met Gly Glu His Asp Phe Ser Lys
                245                 250                 255

Lys Asp Gly Asp Glu Gln Val Arg Arg Val Thr Gln Val Ile Met Pro
                260                 265                 270

Asp Glu Tyr Ile Arg Gly Lys Ile Asn His Asp Ile Ala Leu Leu Arg
            275                 280                 285

Leu His Arg Pro Val Thr Phe Thr Asp Tyr Val Val Pro Leu Cys Leu
    290                 295                 300

Pro Glu Lys Ser Phe Ser Glu Asn Thr Leu Ala Arg Ile Arg Phe Ser
305                 310                 315                 320

Arg Val Ser Gly Trp Gly Gln Leu Leu Asp Arg Gly Ala Thr Ala Leu
                325                 330                 335

Glu Leu Met Ser Ile Glu Val Pro Arg Leu Met Thr Gln Asp Cys Leu
                340                 345                 350

Glu His Ala Glu His Ser Ser Asn Thr Pro Lys Ile Thr Glu Asn Met
            355                 360                 365

Phe Cys Ala Gly Tyr Met Asp Gly Thr Lys Asp Ala Cys Lys Gly Asp
    370                 375                 380

Ser Gly Gly Pro His Ala Thr His Tyr His Gly Thr Trp Tyr Leu Thr
385                 390                 395                 400

Gly Val Val Ser Trp Gly Glu Gly Cys Ala Ala Ile Gly His Ile Gly
                405                 410                 415

Val Tyr Thr Arg Val Ser Gln Tyr Ile Asp Trp Leu Val Arg His Met
            420                 425                 430
```

```
Asp Ser Glu Leu Gln Val Gly Val Phe Arg Leu Pro Leu Leu
            435                 440                 445

<210> SEQ ID NO 58
<211> LENGTH: 461
<212> TYPE: PRT
<213> ORGANISM: Homo sapiens

<400> SEQUENCE: 58

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Glu Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Cys Trp Gly Arg Val Phe His Lys Gly Arg Ser Ala Leu Val
        355                 360                 365
```

```
Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Glu Phe Leu Thr Gly Ile Ile Ser Trp Gly
                420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
    450                 455                 460

<210> SEQ ID NO 59
<211> LENGTH: 452
<212> TYPE: PRT
<213> ORGANISM: Unknown
<220> FEATURE:
<223> OTHER INFORMATION: Description of Unknown Organism: Unknown animal
      vitamin K-dependent prothrombin sequence

<400> SEQUENCE: 59

Met Ala Glu Ala Ser Gly Leu Val Thr Val Cys Leu Leu Gly Tyr Leu
1               5                   10                  15

Leu Ser Ala Glu Cys Ala Val Phe Leu Asp Arg Glu Asn Ala Thr Lys
                20                  25                  30

Ile Leu Ser Arg Pro Lys Arg Tyr Asn Ser Gly Lys Leu Glu Glu Phe
            35                  40                  45

Val Arg Gly Asn Leu Glu Arg Glu Cys Ile Glu Glu Lys Cys Ser Phe
50                  55                  60

Glu Glu Ala Arg Glu Val Phe Glu Asn Thr Glu Lys Thr Thr Glu Phe
65                  70                  75                  80

Trp Lys Gln Tyr Val Asp Gly Asp Gln Cys Glu Ser Asn Pro Cys Leu
                85                  90                  95

Asn Asp Gly Val Cys Lys Asp Asp Ile Asn Ser Tyr Glu Cys Trp Cys
                100                 105                 110

Arg Ala Gly Phe Glu Gly Lys Asn Cys Glu Leu Asp Val Thr Cys Asn
            115                 120                 125

Ile Glu Asn Gly Arg Cys Lys Gln Phe Cys Lys Leu Gly Pro Asp Asn
130                 135                 140

Lys Val Val Cys Ser Asp Thr Thr Gly Tyr Gln Leu Ala Glu Asp Gln
145                 150                 155                 160

Arg Ser Cys Glu Pro Ala Val Pro Phe Pro Cys Gly Arg Val Ser Val
                165                 170                 175

Pro His Ile Ser Met Thr Arg Thr Arg Ala Glu Thr Leu Phe Ser Asn
                180                 185                 190

Met Asp Tyr Glu Asn Ser Thr Glu Val Glu Lys Ile Leu Asp Asn Val
            195                 200                 205

Thr Gln Pro Leu Asn Asp Phe Thr Arg Val Val Gly Gly Lys Asp Ala
        210                 215                 220

Lys Pro Gly Gln Phe Pro Trp Gln Val Leu Leu Asn Gly Lys Val Asp
225                 230                 235                 240

Ala Phe Cys Gly Gly Ser Ile Ile Asn Glu Lys Trp Val Val Thr Ala
                245                 250                 255

Ala His Cys Ile Glu Pro Asp Val Lys Ile Thr Ile Val Ala Gly Glu
```

```
                   260                 265                 270
His Asn Thr Glu Lys Arg Glu His Thr Glu Gln Lys Arg Asn Val Ile
            275                 280                 285

Arg Thr Ile Leu His His Ser Tyr Asn Ala Thr Ile Asn Lys Tyr Asn
        290                 295                 300

His Asp Ile Ala Leu Leu Glu Leu Asp Glu Pro Leu Thr Leu Asn Ser
305                 310                 315                 320

Tyr Val Thr Pro Ile Cys Ile Ala Asp Arg Glu Tyr Ser Asn Ile Phe
                325                 330                 335

Leu Lys Phe Gly Ser Gly Tyr Val Ser Gly Trp Gly Arg Val Phe Asn
            340                 345                 350

Lys Gly Arg Ser Ala Ser Ile Leu Gln Tyr Leu Lys Val Pro Leu Val
        355                 360                 365

Asp Arg Ala Thr Cys Leu Arg Ser Thr Lys Phe Thr Ile Tyr Asn Asn
    370                 375                 380

Met Phe Cys Ala Gly Phe His Glu Gly Gly Lys Asp Ser Cys Gln Gly
385                 390                 395                 400

Asp Ser Gly Gly Pro His Val Thr Glu Val Glu Gly Ile Ser Phe Leu
                405                 410                 415

Thr Gly Ile Ile Ser Trp Gly Glu Glu Cys Ala Met Lys Gly Lys Tyr
            420                 425                 430

Gly Ile Tyr Thr Lys Val Ser Arg Tyr Val Asn Trp Ile Lys Glu Lys
        435                 440                 445

Thr Lys Leu Thr
    450

<210> SEQ ID NO 60
<211> LENGTH: 459
<212> TYPE: PRT
<213> ORGANISM: Mus sp.

<400> SEQUENCE: 60

Ala Leu Ile Thr Ile Phe Leu Leu Gly Tyr Leu Leu Ser Thr Glu Cys
1               5                   10                  15

Ala Val Phe Leu Asp Arg Glu Asn Ala Thr Lys Ile Leu Thr Arg Pro
            20                  25                  30

Lys Arg Tyr Asn Ser Gly Lys Leu Glu Glu Phe Val Arg Gly Asn Leu
        35                  40                  45

Glu Arg Glu Cys Ile Glu Glu Arg Cys Ser Phe Glu Glu Ala Arg Glu
    50                  55                  60

Val Phe Glu Asn Thr Glu Lys Thr Thr Glu Phe Trp Lys Gln Tyr Val
65                  70                  75                  80

Asp Gly Asp Gln Cys Glu Ser Asn Pro Cys Leu Asn Gly Gly Ile Cys
                85                  90                  95

Lys Asp Asp Ile Ser Ser Tyr Glu Cys Trp Cys Gln Val Gly Phe Glu
            100                 105                 110

Gly Arg Asn Cys Glu Leu Asp Ala Thr Cys Asn Ile Lys Asn Gly Arg
        115                 120                 125

Cys Lys Gln Phe Cys Lys Asn Ser Pro Asp Asn Lys Val Ile Cys Ser
    130                 135                 140

Cys Thr Glu Gly Tyr Gln Leu Ala Glu Asp Gln Lys Ser Cys Glu Pro
145                 150                 155                 160

Thr Val Pro Phe Pro Cys Gly Arg Ala Ser Ile Ser Tyr Ser Ser Lys
                165                 170                 175
```

```
Lys Ile Thr Arg Ala Glu Thr Val Phe Ser Asn Met Asp Tyr Glu Asn
            180                 185                 190

Ser Thr Glu Ala Val Phe Ile Gln Asp Asp Ile Thr Asp Gly Ala Ile
        195                 200                 205

Leu Asn Asn Val Thr Glu Ser Ser Glu Ser Leu Asn Asp Phe Thr Arg
    210                 215                 220

Val Val Gly Gly Glu Asn Ala Lys Pro Gly Gln Ile Pro Trp Gln Val
225                 230                 235                 240

Ile Leu Asn Gly Glu Ile Glu Ala Phe Cys Gly Gly Ala Ile Ile Asn
                245                 250                 255

Glu Lys Trp Ile Val Thr Ala Ala His Cys Leu Lys Pro Gly Asp Lys
            260                 265                 270

Ile Glu Val Val Ala Gly Glu Tyr Asn Ile Asp Lys Lys Glu Asp Thr
        275                 280                 285

Glu Gln Arg Arg Asn Val Ile Arg Thr Ile Pro His His Gln Tyr Asn
    290                 295                 300

Ala Thr Ile Asn Lys Tyr Ser His Asp Ile Ala Leu Leu Glu Leu Asp
305                 310                 315                 320

Lys Pro Leu Ile Leu Asn Ser Tyr Val Thr Pro Ile Cys Val Ala Asn
                325                 330                 335

Arg Glu Tyr Thr Asn Ile Phe Leu Lys Phe Gly Ser Gly Tyr Val Ser
            340                 345                 350

Gly Trp Gly Lys Val Phe Asn Lys Gly Arg His Ala Ser Ile Leu Gln
        355                 360                 365

Tyr Leu Arg Val Pro Leu Val Asp Arg Ala Thr Cys Leu Arg Ser Thr
    370                 375                 380

Thr Phe Thr Thr Tyr Asn Asn Met Phe Cys Ala Gly Tyr Arg Glu Gly
385                 390                 395                 400

Gly Lys Asp Ser Cys Glu Gly Asp Ser Gly Gly Pro His Val Thr Glu
                405                 410                 415

Val Glu Gly Thr Ser Phe Leu Thr Gly Ile Ile Ser Trp Gly Glu Glu
            420                 425                 430

Cys Ala Met Lys Gly Lys Tyr Gly Ile Tyr Thr Lys Val Ser Arg Tyr
        435                 440                 445

Val Lys Trp Ile Lys Glu Lys Thr Lys Leu Thr
    450                 455

<210> SEQ ID NO 61
<211> LENGTH: 416
<212> TYPE: PRT
<213> ORGANISM: Bos sp.

<400> SEQUENCE: 61

Tyr Asn Ser Gly Lys Leu Glu Glu Phe Val Arg Gly Asn Leu Glu Arg
1               5                   10                  15

Glu Gln Asp Lys Glu Glu Lys Cys Ser Phe Glu Glu Ala Arg Glu Val
            20                  25                  30

Pro Glu Asn Thr Glu Lys Thr Glu Phe Trp Lys Gln Tyr Val Asp Gly
        35                  40                  45

Asp Gln Cys Glu Ser Asn Pro Cys Leu Asn Gly Gly Met Cys Lys Asp
    50                  55                  60

Asp Ile Asn Ser Tyr Glu Cys Trp Cys Gln Ala Gly Phe Glu Gly Thr
65                  70                  75                  80

Asn Cys Glu Leu Asp Ala Thr Cys Ser Ile Lys Asn Gly Arg Cys Lys
                85                  90                  95
```

-continued

```
Gln Phe Cys Lys Arg Asp Thr Asp Asn Glu Val Val Cys Ser Cys Thr
                100                 105                 110

Asp Gly Tyr Arg Leu Ala Glu Asp Gln Lys Ser Cys Glu Pro Ala Val
            115                 120                 125

Pro Phe Pro Cys Gly Arg Val Ser Val Ser His Ile Ser Lys Lys Leu
130                 135                 140

Thr Arg Ala Glu Thr Ile Phe Ser Asn Thr Asn Tyr Glu Asn Ser Ser
145                 150                 155                 160

Glu Ala Glu Ile Ile Trp Asp Asn Val Thr Gln Ser Asn Gln Ser Phe
                165                 170                 175

Asp Glu Phe Ser Arg Val Val Gly Gly Glu Asp Ala Glu Arg Gly Gln
            180                 185                 190

Phe Pro Trp Gln Val Leu Leu His Gly Glu Ile Ala Ala Phe Cys Gly
        195                 200                 205

Gly Ser Ile Val Asn Glu Lys Trp Val Val Thr Ala Ala His Cys Ile
    210                 215                 220

Lys Pro Gly Val Lys Ile Thr Val Val Ala Gly Glu His Asn Thr Glu
225                 230                 235                 240

Lys Pro Glu Pro Thr Glu Gln Lys Arg Asn Val Ile Arg Ala Ile Pro
                245                 250                 255

Tyr His Ser Tyr Asn Ala Ser Ile Asn Lys Tyr Ser His Asp Ile Ala
            260                 265                 270

Leu Leu Glu Leu Asp Glu Pro Leu Glu Leu Asn Ser Tyr Val Thr Pro
        275                 280                 285

Ile Cys Ile Ala Asp Arg Asp Tyr Thr Asn Ile Phe Ser Lys Phe Gly
    290                 295                 300

Tyr Gly Tyr Val Ser Gly Trp Gly Lys Val Phe Asn Arg Gly Arg Ser
305                 310                 315                 320

Ala Ser Ile Leu Gln Tyr Leu Lys Val Pro Leu Val Asp Arg Ala Thr
                325                 330                 335

Cys Leu Arg Ser Thr Lys Phe Ser Ile Tyr Ser His Met Phe Cys Ala
            340                 345                 350

Gly Tyr His Glu Gly Gly Lys Asp Ser Cys Gln Gly Asp Ser Gly Gly
        355                 360                 365

Pro His Val Thr Glu Val Glu Gly Thr Ser Phe Leu Thr Gly Ile Ile
    370                 375                 380

Ser Trp Gly Glu Glu Cys Ala Met Lys Gly Lys Tyr Gly Ile Tyr Thr
385                 390                 395                 400

Lys Val Ser Arg Tyr Val Asn Trp Ile Lys Glu Lys Thr Lys Leu Thr
                405                 410                 415
```

<210> SEQ ID NO 62
<211> LENGTH: 478
<212> TYPE: PRT
<213> ORGANISM: Homo sapiens

<400> SEQUENCE: 62

```
Met Gly Arg Pro Leu His Leu Val Leu Leu Ser Ala Ser Leu Ala Gly
1               5                   10                  15

Ile Leu Leu Leu Gly Glu Ser Leu Phe Ile Arg Arg Glu Gln Ala Asn
            20                  25                  30

Asn Ile Leu Ala Arg Val Thr Arg Ala Asn Ser Pro Leu Glu Glu Met
        35                  40                  45

Lys Lys Gly His Leu Glu Arg Glu Cys Met Glu Glu Thr Cys Ser Tyr
```

```
            50                  55                  60
Glu Glu Ala Arg Glu Val Phe Glu Asp Ser Asp Lys Thr Asn Glu Phe
 65                  70                  75                  80

Trp Asn Lys Tyr Lys Asp Gly Asp Gln Cys Glu Thr Ser Pro Cys Gln
                 85                  90                  95

Asn Cys Gly Lys Cys Lys Asp Gly Leu Gly Glu Tyr Thr Cys Thr Cys
                100                 105                 110

Leu Glu Gly Phe Glu Gly Lys Asn Cys Glu Leu Phe Thr Arg Lys Leu
                115                 120                 125

Cys Ser Leu Asp Asn Gly Asp Cys Asp Gln Phe Cys His Glu Glu Gln
                130                 135                 140

Trp Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
                180                 185                 190

Glu Ala Pro Asp Ser Ile Thr Trp Lys Pro Tyr Asp Ala Ala Asp Leu
                195                 200                 205

Asp Pro Thr Glu Asn Pro Phe Asp Leu Leu Asp Phe Asn Gln Thr Gln
                210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
                260                 265                 270

Thr Ala Ala His Cys Leu Tyr Gln Ala Lys Arg Phe Lys Val Arg Val
                275                 280                 285

Gly Asp Arg Asn Thr Glu Gln Glu Glu Gly Gly Glu Ala Val His Glu
                290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
                340                 345                 350

Leu Met Thr Gln Lys Thr Gly Ile Val Ser Gly Phe Gly Arg Thr His
                355                 360                 365

Glu Glu Gly Arg Gln Ser Thr Arg Leu Lys Met Leu Glu Val Pro Tyr
                370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
                420                 425                 430

Val Thr Gly Ile Val Ser Trp Gly Glu Gly Cys Ala Arg Lys Gly Lys
                435                 440                 445

Tyr Gly Ile Tyr Thr Lys Val Thr Ala Pro Leu Lys Trp Ile Asp Arg
                450                 455                 460

Ser Met Lys Thr Arg Gly Leu Pro Lys Ala Lys Ser His Ala
465                 470                 475
```

<210> SEQ ID NO 63
<211> LENGTH: 475
<212> TYPE: PRT
<213> ORGANISM: Mus sp.

<400> SEQUENCE: 63

Met Gly Ser Pro Val Gln Leu Ser Leu Leu Cys Val Val Leu Ala Ser
1               5                   10                  15

Ile Leu Leu Pro Gly Lys Gly Val Phe Ile Asn Arg Glu Arg Ala Asn
            20                  25                  30

Asn Val Leu Ala Arg Thr Arg Arg Ala Asn Ser Phe Phe Glu Glu Phe
        35                  40                  45

Lys Lys Gly Asn Leu Glu Arg Glu Cys Met Glu Glu Ile Cys Ser Tyr
    50                  55                  60

Glu Glu Val Arg Glu Ile Pro Glu Asp Asp Glu Lys Thr Lys Glu Tyr
65                  70                  75                  80

Trp Thr Lys Tyr Lys Asp Gly Asp Gln Cys Glu Ser Ser Pro Cys Gln
                85                  90                  95

Asn Cys Gly Ala Cys Arg Asp Gly Ile Gly Gly Tyr Thr Cys Thr Cys
            100                 105                 110

Ser Glu Gly Phe Glu Gly Lys Asn Cys Glu Leu Phe Val Arg Lys Leu
        115                 120                 125

Cys Arg Leu Asp Asn Gly Asp Cys Asp Gln Pro Cys Arg Glu Glu Gln
    130                 135                 140

Asn Ser Val Val Cys Ser Cys Ala Ser Gly Tyr Phe Leu Gly Asn Cys
145                 150                 155                 160

Gly Lys Ser Cys Ile Ser Thr Ala Pro Pro Cys Gly Lys Ile Thr
                165                 170                 175

Thr Gly Arg Arg Lys Arg Ser Val Ala Leu Asn Thr Ser Asp Ser Glu
            180                 185                 190

Leu Asp Leu Glu Asp Ala Leu Leu Asp Glu Asp Phe Leu Ser Pro Thr
        195                 200                 205

Glu Asn Pro Ile Glu Leu Leu Asn Leu Asn Glu Thr Gln Pro Glu Arg
    210                 215                 220

Ser Ser Asp Asp Leu Val Arg Ile Val Gly Gly Arg Glu Cys Lys Asp
225                 230                 235                 240

Gly Glu Cys Pro Trp Gln Ala Leu Leu Ile Asn Glu Asp Asn Glu Gly
                245                 250                 255

Phe Cys Gly Gly Thr Ile Leu Asn Glu Pro Tyr Ile Leu Thr Ala Ala
            260                 265                 270

His Cys Leu His Gln Ala Arg Arg Phe Lys Val Arg Val Gly Asp Arg
        275                 280                 285

Asn Thr Glu Lys Glu Glu Gly Asn Glu Met Val His Glu Val Asp Val
    290                 295                 300

Val Ile Lys His Asn Lys Phe Gln Arg Asp Thr Tyr Asp Tyr Asp Ile
305                 310                 315                 320

Ala Val Leu Arg Leu Lys Thr Pro Ile Thr Phe Arg Met Asn Val Ala
                325                 330                 335

Pro Ala Cys Leu Pro Gln Lys Asp Trp Ala Glu Ser Thr Leu Met Thr
            340                 345                 350

Gln Lys Thr Gly Ile Val Ser Gly Phe Gly Arg Thr His Glu Lys Gly
        355                 360                 365

Arg Gln Ser Asn Ile Leu Lys Met Leu Glu Val Pro Tyr Val Asp Arg

```
                    370                 375                 380
Asn Thr Cys Lys Leu Ser Thr Ser Pro Ser Ile Thr Gln Asn Met Phe
385                 390                 395                 400

Cys Ala Gly Tyr Glu Ala Lys Leu Glu Asp Ala Cys Gln Gly Asp Ser
                405                 410                 415

Gly Gly Pro His Val Thr Arg Phe Lys Asn Thr Tyr Tyr Val Thr Gly
            420                 425                 430

Ile Val Ser Trp Gly Glu Gly Cys Ala Arg Lys Gly Lys Tyr Gly Ile
        435                 440                 445

Tyr Thr Lys Val Thr Thr Pro Leu Lys Trp Ile Asp Arg Ser Met Lys
    450                 455                 460

Ala Arg Val Gly Pro Thr Ala Glu Thr Pro Arg
465                 470                 475

<210> SEQ ID NO 64
<211> LENGTH: 476
<212> TYPE: PRT
<213> ORGANISM: Unknown
<220> FEATURE:
<223> OTHER INFORMATION: Description of Unknown Organism: Unknown animal
      vitamin K-dependent prothrombin sequence

<400> SEQUENCE: 64

Met Ala Asn Pro Leu His Leu Val Leu Leu Gly Ala Ala Leu Ala Gly
1               5                   10                  15

Leu Leu Leu Ser Gly Ser Ser Val Phe Ile Ser Arg Arg Ala Ala Asn
            20                  25                  30

Asp Val Leu Ala Arg Thr Arg Arg Ala Asn Ser Phe Leu Glu Glu Leu
        35                  40                  45

Lys Lys Gly Asn Leu Glu Arg Glu Cys Met Glu Glu Asn Cys Ser Val
    50                  55                  60

Glu Glu Ala Leu Glu Val Phe Glu Asp Arg Glu Lys Thr Asn Glu Phe
65                  70                  75                  80

Trp Asn Lys Tyr Val Asp Gly Asp Gln Cys Glu Ser Asn Pro Cys Gln
                85                  90                  95

Asn Cys Gly Thr Cys Lys Asp Gly Leu Gly Met Tyr Thr Cys Ser Cys
            100                 105                 110

Val Glu Gly Tyr Glu Gly Gln Asp Cys Glu Pro Val Thr Arg Lys Leu
        115                 120                 125

Cys Glu Leu Asp Asn Gly Gly Cys Asp Gln Phe Cys Arg Glu Glu Glu
    130                 135                 140

Asn Ser Val Leu Cys Ser Cys Ala Glu Gly Tyr Thr Leu Gly Asp Asn
145                 150                 155                 160

Gly Lys Ser Cys Ile Ser Thr Glu Leu Phe Pro Cys Gly Lys Val Thr
                165                 170                 175

Leu Gly Arg Arg Arg Arg Ser Pro Ala Thr Asn Ser Ser Glu Gly Pro
            180                 185                 190

Pro Glu Ala Pro Gly Pro Glu Gln Gln Asp Gly Asn Leu Thr Ala
        195                 200                 205

Thr Glu Asn Phe Phe Asn Leu Leu Asp Ser Pro Glu Pro Pro Lys
    210                 215                 220

Asp Asp Ser Ser Ser Leu Val Arg Ile Val Gly Gly Gln Asp Cys Arg
225                 230                 235                 240

Asp Gly Glu Cys Pro Trp Gln Ala Leu Leu Val Asn Glu Glu Asn Glu
                245                 250                 255
```

```
Gly Phe Cys Gly Gly Thr Ile Leu Ser Glu Tyr His Val Leu Thr Ala
            260                 265                 270

Ala His Cys Leu His Gln Ala Lys Arg Phe Lys Val Arg Val Gly Asp
        275                 280                 285

Arg Asp Thr Glu His Glu Glu Gly Asn Glu Lys Thr His Glu Val Glu
    290                 295                 300

Val Val Val Lys His Asn Arg Phe Val Lys Glu Thr Tyr Asp Phe Asp
305                 310                 315                 320

Ile Ala Val Leu Arg Leu Lys Thr Pro Ile Thr Phe Arg Arg Asn Val
                325                 330                 335

Ala Pro Ala Cys Leu Pro Gln Lys Asp Trp Ala Glu Ser Thr Leu Met
            340                 345                 350

Ala Gln Lys Thr Gly Ile Val Ser Gly Phe Gly Arg Thr His Glu Met
        355                 360                 365

Gly Arg Leu Ser Thr Thr Leu Lys Met Leu Glu Val Pro Tyr Val Asp
    370                 375                 380

Arg Asn Ser Asp Lys Arg Ser Ser Ser Phe Thr Ile Thr Gln Asn Met
385                 390                 395                 400

Phe Cys Ala Gly Tyr Asp Ala Arg Pro Glu Asp Ala Cys Gln Gly Asp
                405                 410                 415

Ser Gly Gly Pro His Val Thr Arg Phe Arg Asp Thr Tyr Phe Val Thr
            420                 425                 430

Gly Ile Val Ser Trp Gly Glu Gly Cys Ala Arg Lys Gly Lys Phe Gly
        435                 440                 445

Val Tyr Thr Lys Val Ser Asn Phe Leu Lys Trp Ile Glu Lys Glu Met
    450                 455                 460

Arg Ala Arg Ala Val Pro Val Ala Glu Ala Ala Gly
465                 470                 475

<210> SEQ ID NO 65
<211> LENGTH: 477
<212> TYPE: PRT
<213> ORGANISM: Bos sp.

<400> SEQUENCE: 65

Met Ala Gly Leu Leu His Leu Val Leu Leu Ser Thr Ala Leu Gly Gly
1               5                   10                  15

Leu Leu Arg Pro Ala Gly Ser Val Phe Leu Pro Arg Asp Gln Ala His
            20                  25                  30

Arg Val Leu Gln Arg Ala Arg Arg Ala Asn Ser Phe Leu Glu Glu Val
        35                  40                  45

Lys Gln Gly Asn Leu Glu Arg Glu Cys Leu Glu Glu Ala Cys Ser Leu
    50                  55                  60

Glu Glu Ala Arg Glu Val Phe Glu Asp Ala Glu Gln Thr Asp Glu Phe
65                  70                  75                  80

Trp Ser Lys Tyr Lys Asp Gly Asp Gln Cys Glu Gly His Pro Cys Leu
                85                  90                  95

Asn Gln Gly His Cys Lys Asp Gly Ile Gly Asp Tyr Thr Cys Thr Cys
            100                 105                 110

Ala Glu Gly Phe Glu Gly Lys Asn Cys Glu Phe Ser Thr Arg Glu Ile
        115                 120                 125

Cys Ser Leu Asp Asn Gly Gly Cys Asp Gln Phe Cys Arg Glu Glu Arg
    130                 135                 140

Ser Glu Val Arg Cys Ser Cys Ala His Gly Tyr Val Leu Gly Asp Cys
145                 150                 155                 160
```

```
Ser Lys Ser Cys Val Ser Thr Lys Arg Phe Pro Cys Gly Lys Phe Thr
                165                 170                 175

Gln Gly Arg Ser Arg Arg Trp Ala Ile His Thr Ser Glu Asp Ala Leu
            180                 185                 190

Asp Ala Ser Glu Leu Glu His Tyr Asp Pro Ala Asp Leu Ser Pro Thr
        195                 200                 205

Glu Ser Ser Leu Asp Leu Leu Gly Leu Asn Arg Thr Glu Pro Ser Ala
    210                 215                 220

Gly Glu Asp Gly Ser Gln Val Val Arg Ile Val Gly Gly Arg Asp Cys
225                 230                 235                 240

Ala Glu Gly Glu Cys Pro Trp Gln Ala Leu Leu Val Asn Glu Glu Asn
                245                 250                 255

Glu Gly Phe Cys Gly Gly Thr Ile Leu Asn Glu Phe Tyr Val Leu Thr
            260                 265                 270

Ala Ala His Cys Leu His Gln Ala Lys Arg Phe Thr Val Arg Val Gly
        275                 280                 285

Asp Arg Asn Thr Glu Gln Glu Glu Gly Asn Glu Met Ala His Glu Val
    290                 295                 300

Glu Met Thr Val Lys His Ser Arg Phe Val Lys Glu Thr Tyr Asp Phe
305                 310                 315                 320

Asp Ile Ala Val Leu Arg Leu Lys Thr Pro Ile Arg Phe Arg Arg Asn
                325                 330                 335

Val Ala Pro Ala Cys Leu Pro Glu Lys Asp Trp Ala Glu Ala Thr Leu
            340                 345                 350

Met Thr Gln Lys Thr Gly Ile Val Ser Gly Phe Gly Arg Thr His Glu
        355                 360                 365

Lys Gly Arg Leu Ser Ser Thr Leu Lys Met Leu Glu Val Pro Tyr Val
    370                 375                 380

Asp Arg Ser Thr Cys Lys Leu Ser Ser Ser Phe Thr Ile Thr Pro Asn
385                 390                 395                 400

Met Phe Cys Ala Gly Tyr Asp Thr Gln Pro Glu Asp Ala Cys Gln Gly
                405                 410                 415

Asp Ser Gly Gly Pro His Val Thr Arg Phe Lys Asp Thr Tyr Phe Val
            420                 425                 430

Thr Gly Ile Val Ser Trp Gly Glu Gly Cys Ala Arg Lys Gly Lys Arg
        435                 440                 445

Gly Val Tyr Thr Lys Val Ser Asn Phe Leu Lys Trp Ile Asp Lys Ile
    450                 455                 460

Met Lys Ala Arg Ala Gly Ala Ala Gly Ser Arg Gly His
465                 470                 475

<210> SEQ ID NO 66
<211> LENGTH: 462
<212> TYPE: PRT
<213> ORGANISM: Homo sapiens

<400> SEQUENCE: 66

Met Trp Gln Leu Thr Ser Leu Leu Phe Val Ala Thr Trp Gly Ile
1               5                   10                  15

Ser Gly Thr Pro Ala Pro Leu Asp Ser Val Phe Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
```

```
            50                  55                  60
Asp Phe Glu Ala Lys Glu Ile Phe Gln Asn Val Asp Asp Thr Leu
 65                  70                  75                  80

Ala Phe Trp Ser Lys His Val Asp Gly Asp Gln Cys Leu Val Leu Pro
                 85                  90                  95

Leu Glu His Pro Cys Ala Ser Leu Cys Cys Gly His Gly Thr Cys Ile
                100                 105                 110

Asp Gly Ile Gly Ser Phe Ser Cys Asp Cys Arg Ser Gly Trp Glu Gly
                115                 120                 125

Arg Phe Cys Gln Arg Glu Val Ser Phe Leu Asn Cys Ser Leu Asp Asn
            130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Gln Trp Lys Arg Met Glu
                180                 185                 190

Lys Lys Arg Ser His Leu Glu Arg Asp Thr Glu Asp Gln Glu Asp Gln
            195                 200                 205

Val Asp Arg Arg Leu Ile Cys Gly Lys Met Thr Arg Arg Gly Asp Ser
            210                 215                 220

Pro Trp Gln Val Val Leu Leu Asp Ser Lys Lys Lys Leu Ala Cys Gly
225                 230                 235                 240

Ala Val Leu Ile His Pro Ser Trp Val Leu Thr Ala Ala His Cys Met
                245                 250                 255

Asp Glu Ser Lys Lys Leu Leu Val Arg Leu Gly Glu Tyr Asp Leu Arg
                260                 265                 270

Arg Trp Glu Lys Trp Glu Leu Asp Leu Asp Ile Lys Glu Val Phe Val
            275                 280                 285

His Pro Asn Tyr Ser Lys Ser Thr Thr Asp Asn Asp Ile Ala Leu Leu
            290                 295                 300

His Leu Ala Gln Pro Ala Thr Leu Ser Gln Thr Ile Val Pro Ile Cys
305                 310                 315                 320

Leu Pro Asp Ser Gly Leu Ala Glu Arg Glu Leu Asn Gln Ala Gly Gln
                325                 330                 335

Glu Thr Leu Val Thr Gly Trp Gly Tyr His Ser Ser Arg Glu Lys Glu
                340                 345                 350

Ala Lys Arg Asn Arg Thr Phe Val Leu Asn Phe Ile Lys Ile Pro Val
            355                 360                 365

Val Pro His Asn Glu Cys Ser Glu Val Met Ser Asn Met Val Ser Glu
            370                 375                 380

Asn Met Leu Cys Ala Gly Ile Leu Gly Asp Arg Gln Asp Ala Cys Glu
385                 390                 395                 400

Gly Asp Ser Gly Gly Pro Met Val Ala Ser Phe His Gly Thr Trp Phe
                405                 410                 415

Leu Val Gly Leu Val Ser Trp Gly Glu Gly Cys Gly Leu Leu His Asn
                420                 425                 430

Tyr Gly Val Tyr Thr Lys Val Ser Arg Tyr Leu Asp Trp Ile His Gly
            435                 440                 445

His Ile Arg Asp Lys Glu Ala Pro Gln Lys Ser Trp Ala Pro
450                 455                 460

<210> SEQ ID NO 67
```

```
<211> LENGTH: 458
<212> TYPE: PRT
<213> ORGANISM: Unknown
<220> FEATURE:
<223> OTHER INFORMATION: Description of Unknown Organism: Unknown animal
      vitamin K-dependent prothrombin sequence

<400> SEQUENCE: 67

Ile Pro Asp Asp Val Gly Tyr Arg Asn Gln Lys Thr Ala Ser Glu Glu
1               5                   10                  15

Gly Val Cys Val Val Ser Lys Cys Gln Asp Gly Pro Asn Thr Leu Pro
            20                  25                  30

Arg Ala Lys Arg Ala Asn Ser Phe Leu Glu Glu Leu Arg Pro Ser Ser
        35                  40                  45

Leu Glu Arg Glu Cys Val Glu Glu Val Cys Asp Leu Glu Glu Ala Lys
    50                  55                  60

Glu Ile Phe Gln Ser Val Asp Asp Thr Leu Ala Phe Trp Tyr Lys Tyr
65                  70                  75                  80

Val Asp Gly Asp Gln Cys Ala Ala Leu Phe Ser Glu His Pro Cys Ser
                85                  90                  95

Ser Gln Cys Cys Gly His Gly Thr Cys Ala Asp Ser Ile Gly Gly Phe
            100                 105                 110

Ser Cys Gln Cys His Gly Gly Trp Glu Gly Ser Phe Cys Gln Tyr Glu
        115                 120                 125

Val Arg Phe Ser Asn Cys Ser Val Asp Asn Gly Gly Cys Ala His Tyr
    130                 135                 140

Cys Leu Glu Glu Glu Ala Gly Arg Ser Cys Ser Cys Ala Pro Gly Tyr
145                 150                 155                 160

Glu Leu Ala Asp Cys His Leu Gln Cys Glu Phe Ala Val Arg Phe Pro
                165                 170                 175

Cys Gly Arg Leu Gly Trp Lys Arg Ile Glu Lys Lys Arg Gly Asn Val
            180                 185                 190

Lys Arg Asp Leu Glu Gln Val Asp Glu Met Asp Glu Val Asp Pro Arg
        195                 200                 205

Leu Ile Asp Gly Lys Leu Thr Arg Arg Gly Asp Ser Pro Trp Gln Val
    210                 215                 220

Ile Leu Leu Asp Ser Lys Lys Lys Leu Ala Cys Gly Ala Val Leu Ile
225                 230                 235                 240

His Val Ser Trp Val Leu Thr Ala Ala His Cys Met Glu Glu Pro Lys
                245                 250                 255

Lys Leu Phe Val Arg Leu Gly Glu Tyr Asp Leu Arg Arg Lys Glu Arg
            260                 265                 270

Trp Glu Leu Asp Leu Asn Ile Gln Glu Val Leu Ile His Pro Asn Tyr
        275                 280                 285

Ser Arg Ser Thr Thr Asp Asn Asp Ile Ala Leu Leu Arg Leu Ala Gln
    290                 295                 300

Pro Ala Thr Leu Ser Gln Thr Ile Val Pro Ile Cys Leu Pro Asp Asn
305                 310                 315                 320

Gly Leu Ala Glu Arg Glu Leu Met Gln Ala Gly Gln Glu Thr Val Val
                325                 330                 335

Thr Gly Trp Gly Tyr His Ser Ser Arg Glu Lys Glu Ala Lys Arg Asn
            340                 345                 350

Arg Thr Phe Ile Leu Asn Phe Ile Thr Val Pro Val Ala Pro Gln Asn
        355                 360                 365

Glu Cys Glu Gln Val Met Ser Asn Ile Ile Ser Glu Asn Met Leu Cys
```

```
                370             375             380
Ala Gly Ile Leu Gly Asp Arg Arg Asp Ala Cys Asp Gly Asp Ser Gly
385                 390                 395                 400

Gly Pro Met Val Ala Ser Phe Arg Gly Thr Trp Phe Leu Val Gly Leu
                405                 410                 415

Val Ser Trp Gly Glu Gly Cys Gly Asp Leu Asn Asn Tyr Gly Val Tyr
            420                 425                 430

Thr Lys Val Ser Arg Tyr Leu Asp Trp Ile His Ser His Leu Glu Glu
        435                 440                 445

Lys Glu Ala Ala Pro Glu Ser Pro Ala Pro
    450                 455

<210> SEQ ID NO 68
<211> LENGTH: 455
<212> TYPE: PRT
<213> ORGANISM: Bos sp.

<400> SEQUENCE: 68

Thr Ser Leu Leu Leu Phe Val Thr Ile Trp Gly Ile Ser Ser Thr Pro
1               5                   10                  15

Ala Pro Pro Asp Ser Val Phe Ser Ser Gln Arg Ala His Gln Val
            20                  25                  30

Leu Arg Ile Arg Lys Arg Ala Asn Ser Phe Leu Glu Glu Leu Arg Pro
        35                  40                  45

Gly Asn Val Glu Arg Glu Cys Ser Glu Glu Val Cys Glu Phe Glu Glu
    50                  55                  60

Ala Arg Glu Ile Phe Gln Asn Thr Glu Asp Thr Met Ala Pro Trp Ser
65                  70                  75                  80

Phe Tyr Ser Asp Gly Asp Gln Cys Glu Asp Arg Pro Ser Gly Ser Pro
                85                  90                  95

Cys Asp Leu Pro Cys Cys Gly Pro Gly Lys Cys Ile Asp Gly Leu Gly
            100                 105                 110

Gly Phe Arg Cys Asp Cys Ala Glu Gly Trp Glu Gly Arg Phe Cys Leu
        115                 120                 125

His Glu Val Arg Phe Ser Asn Cys Ser Ala Glu Asn Gly Gly Cys Ala
    130                 135                 140

His Tyr Cys Met Glu Glu Gly Arg Arg His Cys Ser Cys Ala Pro
145                 150                 155                 160

Gly Tyr Arg Leu Glu Asp Asp His Gln Leu Cys Val Ser Lys Val Thr
                165                 170                 175

Pro Pro Cys Gly Arg Leu Gly Lys Arg Met Glu Lys Lys Arg Lys Thr
            180                 185                 190

Leu Lys Arg Asp Thr Asn Gln Val Asp Gln Lys Asp Gln Leu Asp Pro
        195                 200                 205

Arg Ile Val Asp Gly Gln Glu Ala Gly Trp Gly Glu Ser Pro Trp Gln
    210                 215                 220

Ala Val Leu Leu Asp Ser Lys Lys Lys Leu Val Cys Gly Ala Val Leu
225                 230                 235                 240

Ile His Val Ser Trp Val Leu Thr Val Ala His Cys Leu Asp Ser Arg
                245                 250                 255

Lys Lys Leu Ile Val Arg Leu Gly Glu Tyr Asp Met Arg Arg Trp Glu
            260                 265                 270

Ser Trp Glu Val Asp Leu Asp Ile Lys Glu Val Ile Ile His Pro Asn
        275                 280                 285
```

```
Tyr Thr Lys Ser Thr Ser Asp Asn Asp Ile Ala Leu Leu Arg Leu Ala
            290                 295                 300

Lys Pro Ala Thr Leu Ser Gln Thr Ile Val Pro Ile Cys Leu Pro Asp
305                 310                 315                 320

Ser Gly Leu Ser Glu Arg Lys Leu Thr Gln Val Gly Gln Glu Thr Val
                325                 330                 335

Val Thr Gly Trp Gly Tyr Arg Asp Glu Thr Lys Arg Asn Arg Thr Phe
                340                 345                 350

Val Leu Ser Phe Ile Lys Val Pro Val Val Pro Tyr Asn Ala Cys Val
                355                 360                 365

His Ala Met Glu Asn Lys Ile Ser Glu Asn Met Leu Cys Ala Gly Ile
            370                 375                 380

Leu Gly Asp Pro Arg Asp Ala Cys Glu Gly Asp Ser Gly Gly Pro Met
385                 390                 395                 400

Val Thr Phe Phe Arg Gly Thr Trp Pro Leu Val Gly Leu Val Ser Trp
                405                 410                 415

Gly Glu Gly Cys Gly Arg Leu Tyr Asn Tyr Gly Val Tyr Thr Lys Val
                420                 425                 430

Ser Arg Tyr Leu Asp Trp Ile Tyr Gly His Ile Lys Ala Gln Glu Ala
                435                 440                 445

Pro Leu Glu Ser Gln Val Pro
450                 455

<210> SEQ ID NO 69
<211> LENGTH: 461
<212> TYPE: PRT
<213> ORGANISM: Mus sp.

<400> SEQUENCE: 69

Met Trp Gln Phe Arg Val Pro Leu Leu Leu Met Ser Thr Trp Gly Ile
1               5                   10                  15

Ser Ser Ile Pro Ala His Pro Asp Pro Val Phe Ser Ser Glu His
            20                  25                  30

Ala His Gln Val Leu Arg Val Arg Arg Ala Asn Ser Phe Leu Glu Glu
            35                  40                  45

Met Arg Pro Gly Ser Leu Glu Arg Glu Cys Met Glu Glu Ile Cys Asp
50                  55                  60

Phe Glu Glu Ala Gln Glu Ile Phe Gln Asn Val Glu Asp Thr Leu Ala
65                  70                  75                  80

Phe Trp Ile Lys Tyr Phe Asp Gly Asp Gln Cys Ser Ala Pro Pro Leu
                85                  90                  95

Asp His Gln Cys Asp Ser Pro Cys Cys Gly His Gly Thr Cys Ile Asp
                100                 105                 110

Gly Ile Gly Ser Phe Ser Cys Ser Cys Asp Lys Gly Trp Glu Gly Lys
            115                 120                 125

Phe Cys Gln Gln Glu Leu Arg Phe Gln Asp Cys Arg Val Asn Asn Gly
130                 135                 140

Gly Cys Leu His Tyr Gln Leu Glu Glu Ser Asn Gly Arg Arg Cys Ala
145                 150                 155                 160

Cys Ala Pro Gly Tyr Glu Leu Ala Asp Asp His Met Arg Cys Lys Ser
                165                 170                 175

Thr Val Asn Pro Pro Cys Gly Lys Leu Gly Arg Trp Ile Glu Lys Lys
                180                 185                 190

Arg Lys Ile Leu Glu Arg Asp Thr Asp Leu Glu Asp Glu Leu Glu Pro
            195                 200                 205
```

```
Asp Pro Arg Ile Val Asn Gly Thr Leu Thr Lys Gln Gly Asp Ser Pro
    210             215             220
Trp Gln Ala Ile Leu Leu Asp Ser Lys Lys Lys Leu Ala Cys Gly Gly
225             230             235             240
Val Leu Ile His Thr Ser Trp Val Leu Thr Ala Ala His Cys Val Glu
                245             250             255
Gly Thr Lys Lys Leu Thr Val Arg Leu Gly Glu Tyr Asp Leu Arg Arg
            260             265             270
Arg Asp His Trp Pro Leu Asp Leu Asp Ile Lys Glu Ile Leu Val His
    275             280             285
Pro Asn Tyr Thr Arg Ser Ser Asp Asn Asp Ile Ala Leu Leu Arg
    290             295             300
Leu Ala Gln Pro Ala Thr Leu Ser Lys Thr Ile Val Pro Ile Cys Leu
305             310             315             320
Pro Asn Asn Gly Leu Ala Gln Gln Glu Leu Thr Gln Ala Gly Gln Glu
                325             330             335
Thr Val Val Thr Gly Trp Gly Tyr Gln Ser Asp Arg Ile Lys Asp Gly
                340             345             350
Arg Arg Asn Arg Thr Phe Ile Leu Thr Phe Ile Arg Ile Pro Leu Val
            355             360             365
Ala Arg Asn Glu Cys Val Glu Val Met Lys Asn Val Val Ser Glu Asn
    370             375             380
Met Leu Cys Ala Gly Ile Ile Gly Asn Thr Arg Asp Ala Cys Asp Gly
385             390             395             400
Asp Ser Gly Gly Pro Met Val Val Phe Phe Arg Gly Thr Trp Pro Leu
                405             410             415
Val Gly Leu Val Ser Trp Gly Glu Gly Cys Gly His Thr Asn Asn Tyr
            420             425             430
Gly Ile Tyr Thr Lys Val Gly Ser Tyr Leu Lys Trp Ile His Ser Tyr
        435             440             445
Ile Gly Glu Lys Gly Val Ser Leu Lys Ser Gln Lys Leu
    450             455             460
```